United States Patent [19]
Kato et al.

[11] Patent Number: 5,607,939
[45] Date of Patent: Mar. 4, 1997

[54] CONDENSED HETEROCYCLIC COMPOUNDS, THEIR PRODUCTION AND USE

[75] Inventors: Kaneyoshi Kato, Hyogo; Yoshihiro Sugiura, Nara; Koichi Kato, Ibaraki; Yasuo Nagai, Osaka, all of Japan

[73] Assignee: Takeda Chemical Industries, Ltd., Osaka, Japan

[21] Appl. No.: 428,499

[22] Filed: Apr. 25, 1995

[30] Foreign Application Priority Data

Apr. 28, 1994 [JP] Japan .................... 6-092769
Apr. 28, 1994 [JP] Japan .................... 6-114054

[51] Int. Cl.$^6$ .................. A61K 31/44; C07D 401/06
[52] U.S. Cl. .............. 514/278; 514/399; 514/233.5; 514/414; 514/459; 514/255; 514/320; 514/212; 514/213; 514/444; 514/337; 514/316; 514/323; 514/367; 548/311.4; 548/454; 548/159; 546/201; 546/150; 546/187; 546/281.7; 546/282.7; 546/17; 546/196; 546/272.7; 546/277.1; 546/276.4; 544/364; 544/376; 544/151; 544/368; 540/594; 540/596; 549/406; 549/60
[58] Field of Search .................. 548/311.4, 454, 548/159; 546/201, 150, 187, 269, 17, 196; 544/364, 376, 151, 368; 540/594, 596; 549/406, 60; 514/399, 233.5, 414, 459, 255, 278, 320, 212, 213, 444, 337, 316, 323, 367

[56] References Cited

U.S. PATENT DOCUMENTS 2,759,936 8/1956 Specter .................. 260/247.5
3,553,218 1/1971 Unger et al. .............. 260/286
3,880,885 4/1975 Houlihan et al. ............. 260/343.2
4,247,553 1/1981 McCall .................... 424/250
4,650,884 3/1987 Bogeso .................... 549/467

FOREIGN PATENT DOCUMENTS 1374337 11/1974 United Kingdom.

OTHER PUBLICATIONS

McCall, J. M., 1-(Alkylamino)isochromans: Hypotensives with Preipheral and Central Activities, J. Med. Chem., 25, pp. 75-81 1982.

Primary Examiner—Joseph McKane
Assistant Examiner—Richard S. Myers, Jr.
Attorney, Agent, or Firm—Fitzpatrick, Cella, Harper & Scinto

[57] ABSTRACT

The compound

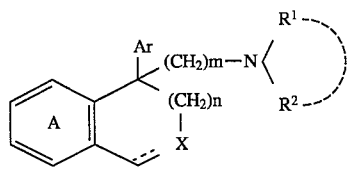

wherein ring A represents a benzene ring; Ar represents an aromatic group; $R^1$ and $R^2$ independently represent hydrogen, acyl or hydrocarbon group or $R^1$ and $R^2$ taken together with the adjacent nitrogen atom represent a nitrogen-containing heterocyclic group; m represents an integer of 1 to 6; n represents an integer of 2 to 3; ----- represents a single bond or a double bond; X stands for —O— or —NR$^3$— in which $R^3$ represents hydrogen, acyl or hydrocarbon group where ----- is a single bond or =N— where ----- is a double bond has excellent GnRH receptor antagonizing activity, calcium antagonizing and monoamine-uptake inhibiting activities and and value as a prophylactic/therapeutic drug for sex hormone-dependent diseases and for central nervous system diseases.

23 Claims, No Drawings

CONDENSED HETEROCYCLIC COMPOUNDS, THEIR PRODUCTION AND USE

BACKGROUND OF THE INVENTION

1. Field of the Invention

This invention relates to a novel condensed heterocyclic compounds which have excellent gonadotropin-releasing hormone (GnRH) receptor antagonizing activity, as well as processes for producing the compounds, pharmaceutical compositions containing the compound, and medical uses for the pharmaceutical compositions.

The compounds of this invention also have calcium-antagonizing and monoamine-uptake inhibiting activities and are therefore useful as a prophylactic/therapeutic drug for acute and chronic central nervous system disorders and CNS-related diseases, such as dysmnesia.

2. Related Prior Art

Gonadotropin-releasing hormone (GnRH) is a deca-peptide consisting of 10 amino acids produced in the hypothalamus. It is known that this hormone regulates secretion of luteinizing hormone (LH) and follicle stimulating hormone (FSH) through receptors which are considered to be present in the anterior lobe of the pituitary gland. GnRH thereby exhibits several physiological activities including induction of ovulation. Since an antagonist or agonist that is specific to such receptors is expected to regulate the hormonal activities of GnRH produced from the hypothalamus and control the secretion of anterior pituitary hormones (including LH or FSH, which inhibits the secretion of estrogen in female or testosteron in male) the prophylactic or therapeutic effect on anterior pituitary hormone-dependent diseases can be expected.

Since the discovery of gonadotropin-releasing hormone in 1971, a large number of its congeners have been synthesized in the expectation of agonistic or antagonistic activity. For example, leuprolerin acetate is a compound which has a higher affinity for GnRH receptors and is less easily metabolized than native GnRH.

Repeated administration of leuprolerin acetate, which is 20 to 50-fold as active as native GnRH, causes the so-called receptor down regulation to decrease the release and production of gonadotropin-releasing hormone in the pituitary gland and, for example, reduce the response of the testis to gonadotropin and accordingly, reduce its testosterone-producing capacity to the castrated level or reduce estrogen-producing capacity in the ovary. It is known that the compound consequently shows an antitumor effect on hormone-dependent cancer, for example cancer of the prostate. In fact, leuprolerin acetate is in broad clinical use as a therapeutic agent for prostatic cancer, breast cancer and hystromyoma, as well as endometriosis, among other diseases.

However, these GnRH agonist are peptides which are poorly absorbed after oral administration and and therefore restricted in dosage form. Moreover, they develop agonistic activity transiently before the onset of efficacy following administration so that the steroidal sex hormone concentration in blood increases, sometimes causing a transitory exacerbation such as ostealgia in some cases.

Accordingly, attempts are being made with the object of developing GnRH antagonists which provide therapeutic efficacy, but which are free of the above-mentioned side effects.

As compounds having such GnRH antagonizing activity, there is a list of known compounds such as cyclic hexapeptide derivatives (U.S. Pat. No. 4,659,691) and bicyclic peptide derivatives (J. Med. Chem., 36, 3265–3273, 1993), all of which have been developed with attention focused on the spatial configuration of GnRH. However, since these compounds are peptides, the perennial problems such as poor oral absorption and poor stability in the patient remain to be solved.

Meanwhile, synthesis of non-peptide compounds having GnRH receptor antagonizing activity has also been undertaken. U.S. Pat. No. 4,678,784 describes benzazepine compounds of the formula

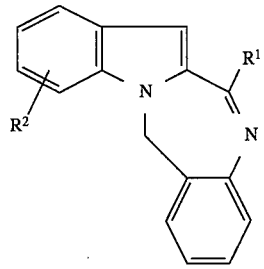

[wherein $R^1$ represents an amino functional group of $-NR^3R^4$, 4-morpholino,

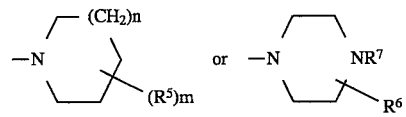

$R^2$ represents hydrogen, alkoxy, alkyl, trifluoromethyl, halogen, nitro, hydroxy or dialkylamino;

$R^4$ and $R^4$ independently represent hydrogen, alkyl, or alkyl substituted by hydroxyl, halogen or alkoxy;

m is equal to 0 or 1;

n is equal to 0, 1 or 2;

$R^5$ represents hydroxyl, alkyl, halogen, carboxy, alkoxycarbonyl, or alkyl substituted by hydroxyl, halogen, alkoxy or phenyl; and $R^6$ represents hydrogen, alkyl, carboxy, alkoxycarbonyl or phenyl;

$R^7$ represents hydrogen, alkyl, alkoxycarbonyl, or alkyl substituted by hydroxyl, halogen, alkoxy, phenoxy or alkoxycarbonyl]. Journal of Medical Chemistry 32, 2036–2038, 1989 describes and mentions that compounds of the formula

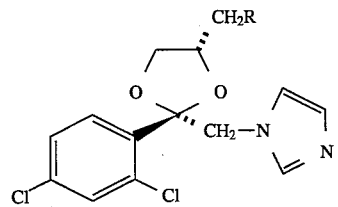

wherein R represents

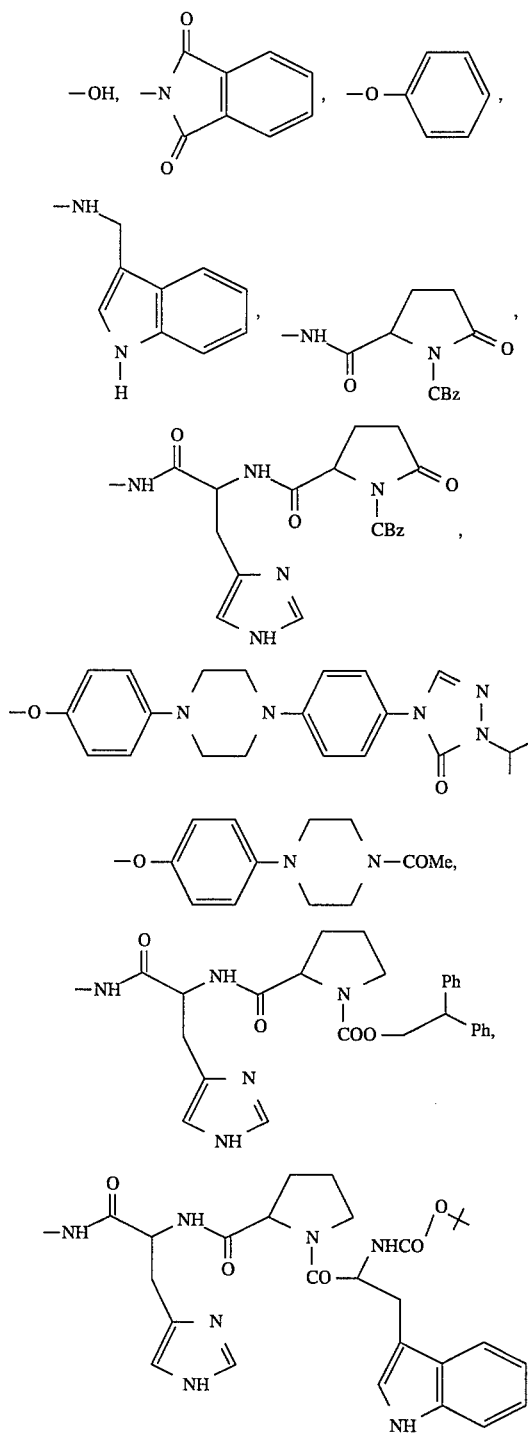

have LHRH (luteinizing hormone-releasing hormone) antagonizing activity.

Meanwhile, it is known that in cerebrovascular disorders or head injury, neuron-excitatory amino acids (among other factors) elevate intracellular $Ca^{2+}$ concentration This elevation of $Ca^{2+}$ concentration causes activation of $Ca^{2+}$-dependent enzymes, which results in the over-excitment and consequent death of neurons, leading to aggravation of symptoms.

For the treatment of these diseases and specifically for controlling an excessive elevation of intracellular $Ca^{2+}$ concentration, a variety of calcium channel blockers represented by dihydropyridines have been employed. However, these non-selective $Ca^{2+}$ channel blockers act peripherally on the heart, blood vessels, etc. as well as the central nervous system. Moreover, some of them, such as flunarizine, have extrapyramidal side effects.

Recently, in dementia accompanied by shedding of neurofilaments, for example in Alzheimer's disease, the role of abnormal intracellular calcium ion concentration in the mechanism of the cytotoxicity of the etiologic factor β-amyloid protein has been pointed out [Mark P. Mattson et al., Trends in NeuroScience, 16, 409]. Against the above background, it is now considered that a CNS-selective calcium ion antagonist would normalize the calcium ion homeostasis in the brain nerve cell and thereby show prophylactic and therapeutic efficacy for dementia.

WO92/06172 describes a piperidine derivative having CNS-selective calcium antagonistic activity.

Meanwhile, U.S. Pat. No. 2,759,936 describes, as an anticonvulsant, a compound of the formula

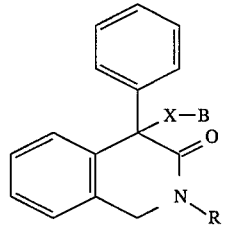

[wherein R represents $C_{1-6}$ alkyl; X represents $C_{2-4}$ alkylene; B represents di (lower) alkyl, piperidino, morpholino, pyrrolidino, N'-alkylpiperazino or pipecolino].

A compound of the formula

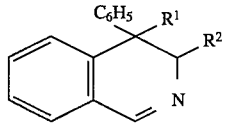

[wherein $R^1$ and $R^2$ independently represent hydrogen or $C_{1-4}$ akyl] is reported (U.S. Pat. No. 3,553,218), a compound of the formula

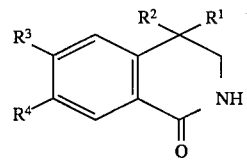

[wherein $R^1$ represents hydrogen, $C_{1-6}$ alkyl or phenyl; $R^2$ represents

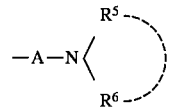

(A represents alkylene; $R^5$ and $R^6$ independently represent alkyl or, taken together with the nitrogen atom, represent a 5- through 7-membered ring); $R^3$ and $R^4$ independently represent $C_{1-4}$ alkoxy] as a cardiovascular drug is reported (U.S. Pat. No. 4,118,494), a compound of the formula

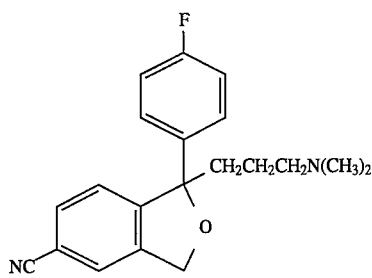

is reported (U.S. Pat. No. 4,650,884), and a compound of the formula

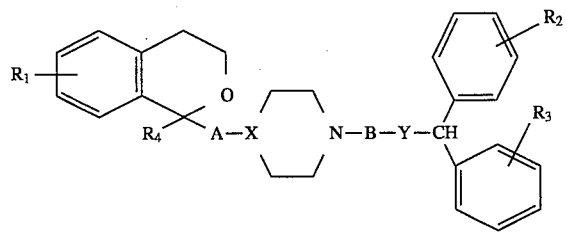

[wherein $R_1$, $R_2$ and $R_3$ independently represent hydrogen, hydroxyl, $C_{1-4}$ alkyl, $C_{1-4}$ alkoxy, halogen, $CF_3$ or methylenedioxy; $R_4$ represents hydrogen or $C_{1-4}$ alkyl; A represents a bond, $C_{1-6}$ alkylene or alkylidene; where Y is a bond, B represents $C_{1-6}$ alkylene or alkylidene; where Y is O, S or $NR^5$, B represents $C_{2-6}$ alkylene; X represents CH or N; $R_5$ represents hydrogen or $C_{1-4}$ alkyl] as a therapeutic drug for angina pectoris and myocardial infarction which has intracellular calcium-antagonizing activity is reported (U.S. Pat. No. 5,238,939).

SUMMARY OF THE INVENTION

This invention has for its object to provide a novel condensed heterocyclic compound (or salt thereof) having excellent gonadotropin-releasing hormone receptor antagonistic activity, calcium-antagonizing and/or monoamine-uptake inhibiting activities.

The inventors of this invention explored compounds having the following nuclear structures and discovered that compounds having both an aromatic group and a nitrogen-terminated alkyl group in the (3+n) position of the above nuclear structure have excellent gonadotropin-releasing hormone receptor antagonistic, calcium-antagonizing and monoamine-uptake inhibiting activities and exhibit minimal toxicity.

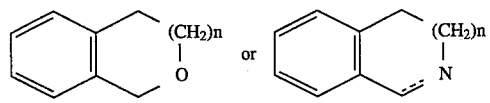

(n represents an integer of 1 to 3.)

This invention has been developed on the basis of the above finding.

DETAILED DESCRIPTION OF THE INVENTION

The present invention generally relates to: a compound of the formula

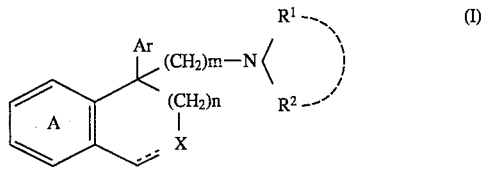

wherein ring A represents a benzene ring which may be substituted,

Ar represents an aromatic group which may be substituted, $R^1$ and $R^2$ independently represent hydrogen atom, acyl group or hydrocarbon group (residue) which may be substituted or $R^1$ and $R^2$ taken together with the adjacent nitrogen atom represent a nitrogen-containing heterocyclic group, m represents an integer of 1 to 6, n represents an integer of 1 to 3, ----- represents a single bond or a double bond, X is —O— or —$NR^3$— ($R^3$ represents hydrogen atom, acyl group or hydrocarbon group which may be substituted) where ----- is a single bond, or X is =N— where ----- is a double bond, or a salt thereof.

As used in this specification, the term "benzene ring which may be substituted" means a benzene ring which may be substituted by, for example, halogen, alkyl which may be halogenated, alkoxy which may be halogenated, alkylthio which may be halogenated, nitro, cyano, sulfo, hydroxy, amino, mono- or di($C_{1-6}$)alkylamino (e.g. methylamino, ethylamino, propylamino, dimethylamino, diethylamino, etc.), carboxy, $C_{1-6}$ alkoxycarbonyl (e.g. methoxycarbonyl, ethoxycarbonyl, propoxycarbonyl, isopropoxycarbonyl, butoxycarbonyl, etc.), $C_{1-7}$ acylamino (e.g. formylamino, acetylamino, propionylamino, butyrylamino, benzoylamino, etc.) and methylenedioxy, among others. However, among the above-mentioned substituent groups, nitro, cyano and sulfo are excluded in the case of the "benzene ring which may be substituted" for the ring A. The substituent group may be present in any substitutable position on the benzene ring and may number 1 to 3. Moreover, where the number of substituents is at least 2, they may be the same or different.

The "aromatic group" of the term "aromatic group which may be substituted" as used throughout this specification includes aromatic hydrocarbon groups and heteroaromatic groups, among others.

The "aromatic hydrocarbon group" in this context is a monocyclic or condensed polycyclic aromatic hydrocarbon group, including $C_{6-14}$ aryl groups such as phenyl, naphthyl, indenyl, anthryl, etc. Phenyl is particularly preferred.

The "heteroaromatic group" in the above context is a 5- or 6-membered monocyclic heteroaromatic group having preferably 1–3 hetero-atoms of 1 or 2 kinds as selected from among nitrogen, oxygen and sulfur in addition to carbon as ring members, which may be fused to aromatic rings, such as a benzene ring, to form a bicyclic or tricyclic heteroaromatic group. Thus, 5- or 6-membered monocyclic heteroaromatic groups having 1–3 hetero-atoms selected from among nitrogen, oxygen and sulfur in addition to carbon as ring members, such as 2-thienyl, 3-thienyl, 2-pyridyl, 4-pyridyl, 2-furyl, 3-furyl, 4-quinolyl, 8-quinolyl, 4-isoquinolyl, pyrazinyl, 2-pyrimidinyl, 3-pyrrolyl, 2-imidazolyl, 3-pyridazinyl, 3-isothiazolyl, 1-indolyl, 2-isoindolyl, etc., and bicyclic heteroaromatic groups formed as one benzene ring is fused to the respective monocyclic groups can be mentioned, among others.

Particularly, 5- or 6-membered heterocyclic groups having 1–3 hetero-atoms selected from among nitrogen, oxygen and sulfur in addition to carbon as ring members (e.g. 2-pyridyl, 4-pyridyl, etc.) are preferred.

The substituent groups that may be possessed by the "aromatic group" are similar to those mentioned for the "benzene ring which may be substituted".

The substituent group may be present in any substitutable position on the heteroaromatic group and may number 1 through 3. When the number of substituents is at least 2, they may be the same or different.

The "hydrocarbon group" of the term "hydrocarbon group which may be substituted" as used throughout this specification means any of the groups listed below under (1) or (2), among others.

(1) acyclic hydrocarbon groups:
a) $C_{1-6}$ alkyl (e.g. methyl, ethyl, propyl, isopropyl, butyl, isobutyl, sec-butyl, tert-butyl, pentyl, hexyl, etc.)
b) $C_{2-6}$ alkenyl (e.g. vinyl, allyl, isopropenyl, butenyl, isobutenyl, sec-butenyl, etc.)
c) $C_{2-6}$ alkinyl (e.g. propargyl, ethinyl, butinyl, 1hexinyl, etc.)

(2) Cyclic hydrocarbon groups:
a) $C_{3-6}$ cycloalkyl (e.g. cyclopropyl, cyclobutyl, cyclopentyl, cyclohexyl, etc.); cyclohexyl may be fused to a benzene ring which may be substituted by $C_{1-4}$ alkyl or $C_{1-4}$ alkoxy
b) $C_{6-14}$ aryl (e.g. phenyl, tolyl, xylyl, 1-naphthyl, 2-naphthyl, biphenyl, 2-indenyl, 2-anthryl, etc.); phenyl is preferred
c) $C_{7-16}$ aralkyl (e.g. benzyl, phenethyl, diphenylmethyl, triphenylmethyl, 1-naphthylmethyl, 2-naphthylmethyl, 2-diphenylethyl, 3-phenylpropyl, 4-phenylbutyl, 5-phenylpentyl, etc.); benzyl is preferred The substituent groups which may be possessed by the "hydrocarbon group which may be substituted" are oxo, thioxo, phenyl, phenylamino, phenyloxy and methylenedioxyphenyloxy group, in addition to similar to those mentioned for the "benzene ring which may be substituted".

The substituent group may be present in any substitutable position on the hydrocarbon group and may number 1 to 3. Where the number of substituents is not less than 2, they may be the same or different.

The term "acyl" as used throughout this specification means, among others, —CO—R, —CONH—R, —SO$_2$—R or —CO—OR wherein R represents a hydrocarbon group which may be substituted.

The "hydrocarbon group which may be substituted" for R can be any of those groups mentioned hereinbefore. For example, formyl, acetyl, propionyl, butyryl, valeryl, acryloyl, propiolyl, benzoyl, nicotinoyl, methanesulfonyl, ethanesulfonyl, benzenesulfonyl and toluenesulfonyl can be mentioned as acyl group.

The term "halogen" is typically used in this specification to mean fluorine, chlorine, bromine or iodine. Fluorine and chlorine are preferred.

Preferably, ring A is a benzene ring which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, hydroxy, amino, mono($C_{1-6}$) alkylamino, di($C_{1-6}$)alkylamino, carboxy, $C_{1-6}$ alkoxycarbonyl and $C_{1-7}$ acylamino; and Ar is preferably (i) a $C_{6-14}$ aryl (most preferably, benzene) or (ii) 5- or 6-membered heteroaromatic group having 1 to 3 hetero-atoms selected from nitrogen, oxygen and sulfur, which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino.

The hydrocarbon group which may be substituted is preferably a $C_{1-6}$ alkyl, $C_{2-6}$ alkenyl, $C_{2-6}$ alkinyl, $C_{3-6}$ cycloalkyl, $C_{6-14}$ aryl or $C_{7-16}$ aralkyl group which may be substituted with 1 to 3 substituents selected from the group consisting of halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino; and the nitrogen-containing heterocyclic group is preferably (i) a 5- or 6-membered nitrogen-containing heteroaromatic group having 1 to 3 hetero-atoms selected from nitrogen, oxygen and sulfur, which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino, (ii)

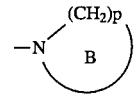

wherein ring B may be substituted by two oxo groups and may be fused to one benzene ring which may be substituted with 1 to 3 substituents selected from the groups consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di ($C_{1-6}$)alkylamino, carboxy, $C_{1-6}$ alkoxycarbonyl and acylamino, p represents an integer of 4 to 7, (iii)

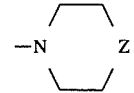

wherein Z represents —O—, >CH—W or >N—W (W represents (a) hydrogen atom or (b) a $C_{6-14}$ aryl or $C_{7-16}$ aralkyl group, which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxy-carbonyl and $C_{1-7}$ acylamino, or (iv)

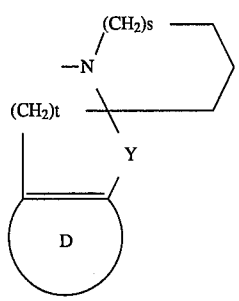

wherein ring D represents (a) a benzene ring or (b) 5- or 6-membered heteroaromatic group having 1 to 3 hetero-atoms selected from nitrogen, oxygen and sulfur, which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$alkylamino, di($C_{1-6}$)alkylamino, carboxy, $C_{1-6}$ alkoxycarbonyl and $C_{1-7}$ acylamino, Y represents —$CH_2$—, —CO— or —CH(OH)—, s and t each represents an integer of 1 to 3.

Ar is also preferably a phenyl group which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino;

Other preferred embodiments are when: $R^1$ represents hydrogen atom and $R^2$ represents a $C_{7-16}$ aralkyl which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxy-carbonyl and $C_{1-7}$ acylamino; or $R^1$ and $R^2$ taken together with the adjacent nitrogen atom form

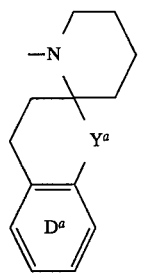

wherein ring $D^a$ represents a benzene ring which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino, $Y^a$ represents —$CH_2$— or —CO—;

Also preferred are those compounds in which:

----- represents a single bond and X represents —O—; or

----- represents a single bond and X represents —$NR^{3a}$— in which $R^{3a}$ represents hydrogen atom or $C_{1-6}$ alkyl group;

Other preferred embodiments are when: ring A is a benzene ring which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, hydroxy, amino, mono($C_{1-6}$)alkylamino, di($C_{1-6}$)alkylamino, carboxy, $C_{1-6}$ alkoxy-carbonyl, $C_{1-7}$ acylamino and methylenedioxy;

the hydrocarbon group which may be substituted is a $C_{1-6}$ alkyl, $C_{2-6}$ alkenyl, $C_{2-6}$ alkinyl, $C_{3-6}$ cycloalkyl, $C_{6-14}$ aryl or $C_{7-16}$ aralkyl group which may be substituted with 1 to 3 substituents selected from the group consisting of halogen, $C_{1-6}$ alkyl which may be halogenated, $C_{1-6}$ alkoxy which may be halogenated, alkylthio which may be halogenated, nitro, cyano, sulfo, hydroxy, amino, mono($C_{1-6}$)alkylamino, di($C_{1-6}$)alkylamino, carboxy, $C_{1-6}$ alkoxy-carbonyl, $C_{1-7}$ acylamino, oxo, thioxo, phenyl, phenylamino, phenyloxy and methylenedioxyphenyloxy; or the nitrogen-containing heterocyclic group is (i) a 5- or 6-membered nitrogen-containing heteroaromatic group having 1 to 3 hetero-atoms selected from nitrogen, oxygen and sulfur, which may be substituted with 1 to 3 substituents selected from the group consisting of halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino, (ii)

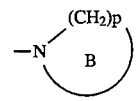

wherein ring B may be substituted by 1 or 2 oxo groups and may be fused to one benzene ring which may be substituted with 1 to 3 substituents selected from the groups consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and acylamino, p represents an integer of 4 to 7, (iii)

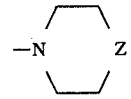

wherein Z represents —O—, >CH—W or >N—W (W represents (a) hydrogen atom, (b) a $C_{6-14}$ aryl or $C_{7-16}$ aralkyl group, which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxy-carbonyl and $C_{1-7}$ acylamino or (c) a heterocyclic group which may be substituted), (iv)

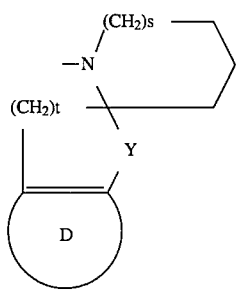

wherein ring D represents (a) a benzene ring or (b) a 5- or 6-membered heteroaromatic group having 1 to 3 heteroatoms selected from nitrogen, oxygen and sulfur, which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino,
Y represents —$CH_2$—, —CO— or —CH(OH)—,
s and t each represents an integer of 1 to 3, or
(v)

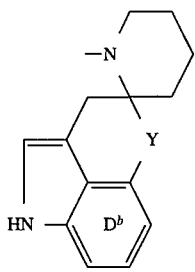

wherein ring $D^b$ represents a benzene ring which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino, Y is —$CH_2$—, —CO— or —CH(OH)—.

These compounds and others according to the formula

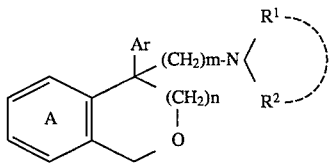

wherein all the symbols are as defined above or a salt thereof, may be produced by reacting a compound of the formula

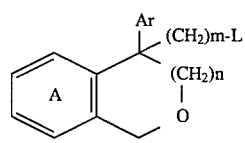

wherein L represents a leaving group and the other symbols are as defined above, or a salt thereof, with a compound of the formula

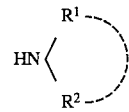

wherein the symbols are as defined above, or a salt thereof.

These compounds and others according to the formula

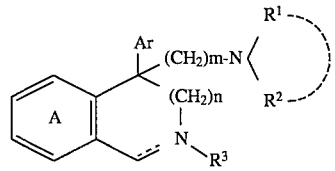

wherein all the symbols are as defined above, or a salt thereof, may be produced by subjecting a compound of the formula

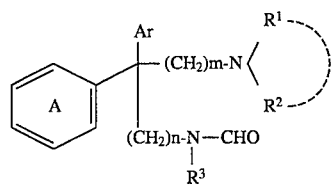

wherein all the symbols are as defined above, or a salt thereof, to cyclization.

The term "alkyl which may be halogenated" as used in this specification means any of $C_{1-6}$ alkyl groups substituted by 1–3 halogen atoms (e.g. fluorine, chlorine, iodine, etc.) (for example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.). Among others, $C_{1-4}$ alkyl groups optionally substituted by 1–3 halogen atoms (e.g. fluorine, chlorine, bromine, etc.) (for example, methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, etc.) are preferable.

The term "alkoxy which may be halogenated" is used in this specification to mean any of $C_{1-6}$ alkoxy groups optionally substituted by 1–3 "halogen atoms" similar to those mentioned above, such as methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc. Among others, $C_{1-4}$ alkoxy groups optionally substituted by 1–3 "halogen atoms" similar to those mentioned above, such as methoxy, difluoromethoxy, trifluoromethoxy, ethoxy, 2,2,2-trifluoroethoxy, propoxy, isopropoxy, butoxy, 4,4,4trifluorobutoxy, isobutoxy, sec-butoxy, etc are preferable.

The term "alkylthio which may be halogenated" is used in this specification to mean any of $C_{1-6}$ alkylthio groups optionally substituted by 1–3 "halogen atoms" similar to those mentioned above, such as methylthio, difluoromethylthio, trifluoromethylthio, ethylthio, propylthio, isopropylthio, butylthio, 4,4,4-trifluorobutylthio, pentylthio, hexylthio, etc., and preferably $C_{1-4}$ alkylthio groups optionally substituted by 1–3 "halogen atoms" similar to those mentioned above, such as methylthio, difluoromethylthio, trifluoromethylthio, ethylthio, propylthio, isopropylthio, butylthio, 4,4,4-trifluorobutylthio and so on.

The phrase "which may be halogenated" as used in this specification is equivalent to "which may be substituted by 1–3 halogen atoms (e.g. fluorine, chlorine, bromine, etc.)".

The "heterocyclic group" of the term "heterocyclic group which may be substituted" as used throughout this specification include a 5- to 11-membered aromatic or non-aromatic heterocyclic group containing 1 to 3 hetero atoms selected from a nitrogen, sulfur and oxygen atom in addition to carbon atoms. Such groups include a 2-thienyl, 3-thienyl, 2-pyridyl, 3-pyridyl, 4-pyridyl, 2-furyl, 3-furyl, 2-quinolyl, 4-quinolyl, 8quinolyl, 3-isoquinolyl, 4-isoquinolyl, pyrazinyl, 2-pyrimidinyl, 3-pyrrolyl, 1-imidazolyl, 2-imidazolyl, 1-pyrazolyl, 2-thiazolyl, 4-thiazolyl, 5-thiazolyl, 3isothiazolyl, 4-isothiazolyl, 3-isoxazolyl, 3-pyridazinyl, 1-pyrrolidinyl, 2-pyrrolidinyl, 3-pyrrolidinyl, 2-pyridon-1-yl, 3-pyridion-1-yl, 1-imidazolidinyl, 2-imidazolidinyl, 3-imidazolidinyl, piperidino, 2-piperidyl, 3-piperidyl, 4-piperidyl, 2-morpholinyl, 3-morpholinyl, morpholino, 1-pipeprazinyl, 2-piperazinyl, 1-isoindolyl, 2-isoindolyl, 1-indolyl, 3-indolyl, phthalimido, 2-benzothiazolyl and 2,3,4,5-tetrahydro-(1H)-3-benzazepinyl group.

The substituent groups which may be possessed by the "heterocyclic group" are similar to those mentioned for the "hydrocarbon group which may be substituted".

The substituent group may be present in any substitutable position on the heterocyclic group and may number 1 to 3. Where the number of substituents is at least 2, they may be the same or different.

The term "nitrogen-containing heterocyclic group" is used throughout this specification to mean any of the following groups, among others.

(i) 5- or 6-membered nitrogen-containing heteroaromatic groups having 1–3 hetero-atoms selected from nitrogen, oxygen and sulfur in addition to carbon as ring members, such as

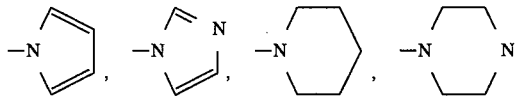

and so on.

(ii)

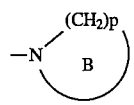

wherein ring B may be substituted by 1 or 2 oxo groups and/or be fused to one benzene ring which may be substituted; p represents an integer of 4 to 7; the "benzene ring which may be substituted" mentioned just above is as defined hereinbefore. Among others, preferred are

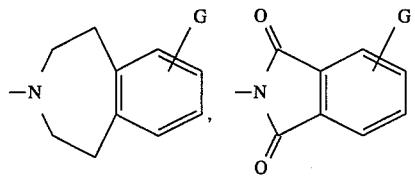

and so on. In the above formulae, G represents halogen (e.g. fluorine, chlorine, etc.), $C_{1-6}$ alkyl (e.g. methyl, ethyl, isopropyl, etc.), or $C_{1-6}$ alkoxy (e.g. methoxy, ethoxy, isopropoxy), etc., for instance.

(iii)

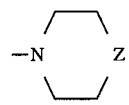

In the above formula, Z represents oxygen, >CH—W or >N—W, wherein W represents (a) hydrogen, (b) a $C_{6-14}$ aryl (e.g. phenyl) or $C_{7-16}$ aralkyl (e.g. benzyl) group which may be substituted or (c) heterocyclic group which may be substituted. The substituent groups which may be possessed by the "$C_{6-14}$ aryl", "$C_{7-16}$ aralkyl" or "heterocyclic group" are similar to those mentioned for the "benzene ring which may be substituted".

Preferred are

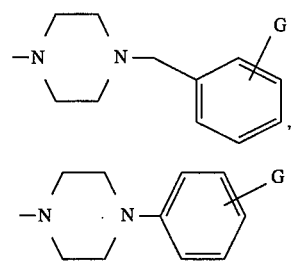

and so on. In the above formulas, G is as defined hereinbefore.

(iv)

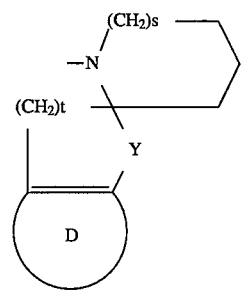

wherein ring D represents an aromatic ring which may be substituted, Y represents —$CH_2$—, —CO— or —CH(OH)—, s and t each represents an integer of 1 to 3.

The "aromatic ring" for the ring D is (a) a benzene ring or (b) 5- or 6-membered heteroaromatic ring having 1 to 3 hetero-atoms selected from nitrogen, oxygen and sulfur in addition to carbon as ring members, such as the following, among others.

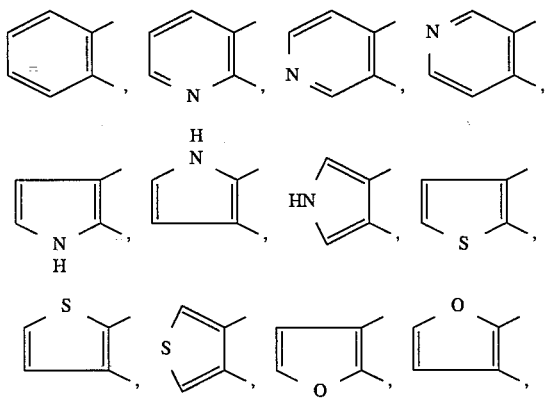

The substituent groups which may be possessed by the "aromatic ring" are similar to those mentioned for the "benzene ring which may be substituted".

Preferably,

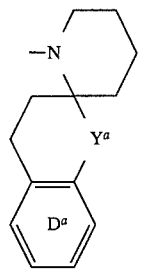

wherein ring $D^a$ represents a benzene ring which may be substituted; $Y^a$ represents —CH$_2$ or —CO—, among others, is used.

A still more preferred example is

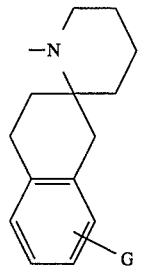

wherein G is as defined hereinbefore.

In the following disclosure in this specification, (i) the halogen may for example be fluorine or chlorine; (ii) $C_{1-6}$ alkyl which may be halogenated may for example be methyl, ethyl, isopropyl or trifluoromethyl; (iii) $C_{1-6}$ alkyl may for example be methyl, ethyl or isopropyl; (iv) $C_{1-6}$ alkoxy which may be halogenated may for example be methoxy, ethoxy, isopropoxy or trifluoromethoxy; (v) $C_{1-6}$ alkoxy may for example be methoxy, ethoxy or isopropoxy; (vi) $C_{1-6}$ alkylthio which may be halogenated may for example be methylthio, ethylthio or isopropylthio; (vii) mono($C_{1-6}$)alkylamino may for example be methylamino or ethylamino; (viii) di($C_{1-6}$)alkylamino may for example be dimethylamino or diethylamino; (ix) $C_{1-6}$ alkoxycarbonyl may for example be methoxycarbonyl, ethoxycarbonyl or isopropoxycarbonyl; and (x) $C_{1-7}$ acylamino may for example be formylamino, acetylamino or propionylamino.

In the above formula, ring A represents a benzene ring which may be substituted.

Preferred is a benzene ring which may be substituted by 1 to 3 substituent groups selected from halogen, $C_{1-6}$ alkyl and $C_{1-6}$ alkoxy, among others. More preferred is an unsubstituted benzene ring.

In the above formula, Ar represents an aromatic group which may be substituted.

Preferred is a phenyl group which may be substituted by 1 to 3 substituents selected from halogen atom, $C_{1-6}$ alkyl which may be substituted, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino.

Still more preferred is a phenyl group which may be substituted by one halogen atom. Specially, an unsubstituted phenyl group is preferred.

Referring, further, to the above formula, $R^1$ and $R^2$ independently represent hydrogen atom, acyl group or a hydrocarbon group which may be substituted; or $R^1$ and $R^2$ taken together with the adjacent nitrogen atom form a nitrogen-containing heterocyclic group.

The preferred combination of $R^1$ and $R^2$, where they do not form a ring, is as follows: $R^1$ is hydrogen and $R^2$ is $C_{7-16}$ aralkyl (e.g. benzyl, phenethyl, etc.) which may be substituted by 1 to 3 substituent groups selected from among halogen, $C_{1-6}$ alkoxy which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and acylamino.

The still more preferred combination is that $R^1$ is hydrogen and $R^2$ is $C_{7-16}$ aralkyl (e.g. benzyl, phenethyl, etc.) which may be substituted by one substituent group selected from halogen, $C_{1-6}$ alkyl, $C_{1-6}$ alkoxy and $C_{1-6}$ alkoxycarbonyl.

The preferred examples of the ring which may be formed by $R^1$ and $R^2$ taken together with the adjacent nitrogen atom are as follows.

(1)

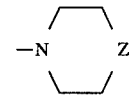

wherein Z represents oxygen, >CH—W or >N—W in which W represents (a) hydrogen or (b) a $C_{6-14}$ aryl (e.g. phenyl) or $C_{7-16}$ aralkyl (e.g. benzyl) group which may be substituted by 1 to 3 substituent groups selected from halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino, or (2)

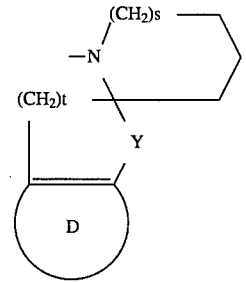

wherein ring D represents (a) a benzene ring or (b) 5- or 6-membered heteroaromatic ring which may be substituted by 1 to 3 hetero-atoms selected from nitrogen, oxygen and sulfur in addition to carbon as ring members (e.g. thiophene, pyridine, etc.) which may be substituted by 1 to 3 substituent groups selected from halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino, Y represents —CH₂—, —CO— or —CH(OH)—, s and t each represents an integer of 1 to 3.

the more preferred examples are (1)

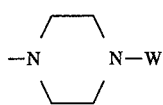

wherein W represents a $C_{6-14}$ aryl (e.g. phenyl) or $C_{7-16}$ aralkyl (e.g. benzyl) group which may be substituted by 1 to 3 substituent groups selected from halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono ($C_{1-6}$)alkylamino, di($C_{1-6}$)alkylamino, carboxy, $C_{1-6}$ alkoxycarbonyl and $C_{1-7}$ acylamino, and (2)

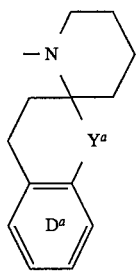

wherein ring $D^a$ represents a benzene ring which may be substituted by 1 to 3 substituent groups selected from among halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$) -alkylamino, di($C_{1-6}$)alkylamino, carboxy, $C_{1-6}$ alkoxycarbonyl and $C_{1-7}$ acylamino, $Y^a$ represents —CH₂— or —CO—.

In the above formulae, m represents an integer of to 6 and is preferably is 3.

Further in the above formulae, n represents an integer of 1 to 3 and is preferable is 1.

In the above formulae, ----- represents a single bond or a double bond.

Where X in the above formulae stands for —O— or —NR³— wherein R³ is hydrogen, acyl or hydrocarbon group 3 which may be substituted where ----- is a single bond, and X stands for =N— where ----- is a double bond.

The "acyl" and "hydrocarbon group which may be substituted" for R³ are both as defined hereinbefore. R³ is preferably hydrogen or a $C_{1-6}$ alkyl group.

Preferably, in the above formula, ----- represents a single bond and X represents —O—.

It is also preferable that, in the above formulae, ----- represents a single bond and X represents —NR³ᵃ— wherein R³ᵃ is hydrogen or $C_{1-6}$ alkyl.

The preferred compounds of this invention are:
(1) compounds of the following formula

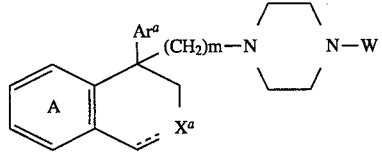

wherein ring A represents a benzene ring which may be substituted by 1 to 3 substituent groups selected from halogen, $C_{1-6}$ alkyl which may be halogenated, $C_{1-6}$ alkoxy which may be halogenated, $C_{1-6}$ alkylthio which may be halogenated, hydroxy, amino, mono($C_{1-6}$)alkylamino, di($C_{1-6}$) alkylamino, carboxy, $C_{1-6}$ alkoxycarbonyl and $C_{1-7}$ acylamino, $Ar^a$ represents phenyl which may be substituted by 1 to 3 substituent groups selected from halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino, W represents a $C_{6-14}$ aryl (e.g. phenyl) or $C_{7-16}$ aralkyl (e.g. benzyl) group which may be substituted by 1 to 3 substituent groups selected from halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino, m represents an integer of 1 to 6, ----- represents a single bond, $X^a$ stands for —O— or —NR³ᵃ— wherein R³ᵃ is hydrogen or $C_{1-6}$ alkyl, or a salt thereof.

(2) Compounds of the formula

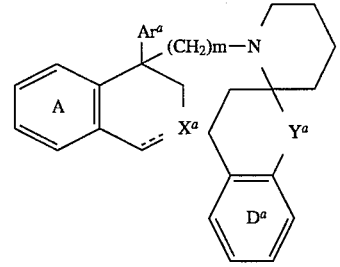

wherein ring A represents a benzene ring which may be substituted by 1 to 3 substituent groups selected from halogen, $C_{1-6}$ alkyl which may be halogenated, $C_{1-6}$ alkoxy which may be halogenated, $C_{1-6}$ alkylthio which may be halogenated, hydroxy, amino, mono($C_{1-6}$)alkylamino, di($C_{1-6}$) alkylamino, carboxy, $C_{1-6}$ alkoxycarbonyl and $C_{1-7}$ acylamino, $Ar^a$ represents phenyl which may be substituted by 1 to 3 substituent groups selected from halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino, ring $D^a$ represents a benzene ring which may be substituted by 1 to 3 substituent groups selected from halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino, $Y^a$ represents —CH₂— or —CO—, m represents an integer of 1 to 6, ----- represents a single bond, $X^a$ stands for —O— or —NR³ᵃ— wherein R³ᵃ is hydrogen or $C_{1-6}$ alkyl, or a salt thereof.

The following is a partial listing of preferred species of the compound of this invention. These compounds have excellent GnRH receptor antagonizing activity.

N,N-Diphenyl-(3-[3-(4-phenylisochroman-4-yl)propyl]amino)propionamide hydrochloride;

N-(2-Phenoxyethyl)-3-[3-(4-phenylisochroman-4-yl)propylaminomethyl]benzamide hydrochloride;

(3) 3,4-Dihydro-6,7-dimethoxy-1'-[3-(4-phenylisochroman-4-yl)propyl]spiro[naphthalene(1(1H),2'-piperidine] hydrochloride;
(4) Methyl 3-[3-(4-phenylisochroman-4-yl)propylaminomethyl]benzoate hydrochloride;
(5) 4-[3-(3-Methylbenzylamino)propyl]-4-phenylisochroman hydrochloride;
(6) 3,4-Dihydro-1'-[3-(4-phenylisochroman-4yl)propyl]spiro[benzo[b]thiophen-5(4H)-4-one,2'-piperidine]hydrochloride;
(7) 3,4-Dihydro-6-methoxy-1'-[3-(4-phenylisochroman-4yl)propyl]spiro[naphthalen-2(1H)-1-one,2'-piperidine]hydrochloride;
(8) 3,4-Dihydro-1'-[3-(4-phenylisochroman-4-yl)propyl]spiro[naphthalen-2(1H)-1-one,2'-piperidine]hydrochloride;
(9) 3,4-Dihydro-6,7-dimethoxy-1'-[3-(4-[fluorophenyl]-isochroman-4-yl)propyl]spiro[naphthalene-2(1H),2'-piperidine]hydrochloride;
(10) 4-[3-(1,2,3,4-Tetrahydronaphthalen-1-yl)aminopropyl]-4-phenylisochroman hydrochloride;
(11) 3,4-Dihydro-1'-[3-(4-[phenylisochroman-4yl)propyl]spiro[naphthalene-2(1H),2'-piperidine] hydrochloride
(12) 4-(3-phenethylaminopropyl)-4-phenylisochroman hydrochloride;
(13) 3,4-Dihydro-6-methoxy-1'-[3-(4-phenylisochroman-4-yl)propyl]spiro[naphthalene-2(1H),2'-piperidine]hydrochloride; and
(14) 3,4-Dihydro-6,7-dimethoxy-1'-[4-(4-phenylisochroman-4-yl)butyl]spiro[naphthalene-2(1H),2'-piperidine] hydrochloride.

Furthermore, the following is a partial listing of the preferred compounds, which have excellent calcium antagonizing or monoamine-uptake inhibiting activities of this, invention.
(1) 3,4-Dihydro-1'-[3-(4-phenylisochroman-4-yl)propyl]spiro[naphthalene-2(1H),2'-piperidine] hydrochloride,
(2) 3,4-Dihydro-1'-[2-(4-phenylisochroman-4-yl)ethyl]spiro[naphthalene-2(1H),2'-piperidine] hydrochloride,
(3) 4-[2-(4-Benzylpiperazin-1-yl)ethyl]-4-phenylisochroman dihydrochloride,
(4) 4-{3-[4-(p-Fluorophenyl)piperazin-1-yl]propyl}-4-phenylisochroman dihydrochloride,
(5) 4-[3-Benzylamino)propyl]-4-phenylisochroman hydrochloride,
(6) 3,4-Dihydro-6-methoxy-1'-[3-(4-phenylisochroman4-yl)propyl]spiro[naphthalene-2(1H),2'-piperidine] hydrochloride,
(7) 4-[3-(4-phenylpiperidino)propyl]-4-phenylisochroman hydrochloride,
(8) 4-[3-(β-phenethylamino)propyl]-4-phenylisochroman hydrochloride,
(9) 4-[3-(o-Fluorobenzylamino)propyl]-4-phenylisochroman hydrochloride,
(10) 4-[3-(o-Chlorobenzylamino)propyl]-4phenylisochroman hydrochloride,
(11) 4-[3-(3,4-Dimethoxyphenethylamino)propyl]-4-phenylisochroman hydrochloride,
(12) 4-[3-(2-Picolylamino)propyl]-4-phenylisochroman dihydrochloride,
(13) 4-[3-(1-Hexamethyleneimino)propyl]-4-phenylisochroman hydrochloride,
(14) 4-(p-Chlorophenyl)-3,4-dihydro-4-[3-(4-phenylpiperazin-1-yl)propyl]isoquinoline trihydrochloride,
(15) 3,4-Dihydro-4-phenyl-4-[3-(4-phenylpiperazin-1-yl)propyl]isoquinoline dihydrochloride,
(16) 4-[3-(N-Benzyl-N-methyl)aminopropyl]-3,4-dihydro-4-phenylisoquinoline dihydrochloride,
(17) 4-{3-[4-(p-Fluorophenyl)piperazin-1-yl]propyl}-1,2,3,4-tetrahydro-4-phenyl-isoquinoline dihydrochloride,
(18) 4-[3-(N-Benzyl-N-methyl)aminopropyl]-4-phenyl-1,2,3,4-tetrahydroisoquinoline dihydrochloride,
(19) 1,2,3,4-Tetrahydro-4-phenyl-4-[3-(4-phenylpiperazin-1-yl)propyl]-1,2,3,4tetrahydroisoquinoline trihydrochloride,
(20) 1,2,3,4-Tetrahydro-2-methyl-4-phenyl-4-[3-(4-phenylpiperazin-1-yl)propyl]isoquinoline trihydrochloride,
(21) 1,2,3,4-Tetrahydro-4-{2-[4-(p-fluorophenyl)piperidino]ethyl}-2-(3-methoxyphenylaminocarbonyl)-4-phenylisoquinoline,
(22) 4-(p-Chlorophenyl)-2-methyl-4-[3-(4-phenylpiperidino)propyl]-1,2,3,4-tetrahydroisoquinoline dihydrochloride, and
(23) 4-[3-(N-Benzyl-N-methylamino)propyl]-4-phenyl-2-phenylcarbamoyl-1,2,3,4-tetrahydroisoquinoline hydrochloride.

The preferred salts of compound (I) of this invention include medicinally acceptable acid addition salts. Among such salts are salts with inorganic acids, such as hydrochloride, hydrobromide, hydroiodide, sulfate, phosphate, etc., and salts with organic acids, such as acetate, oxalate, succinate, ascorbate, maleate, lactate, citrate, tartrate, methanesulfonate, benzoate and so on.

Among species of the compound of this invention are optically active compounds and, of course, the respective isomers available on optical resolution fall within the scope of this invention.

Such optical isomers can be obtained by the per se known technology, e.g. by using an optically active synthetic intermediate or subjecting the final racemic compound to optical resolution in the conventional manner, The technology that can be used for the optical resolution includes a method which comprises preparing a salt with an optically active acid and separating the salt by fractional recrystallization; a method which comprises subjecting the racemic compound or salt to chromatography using a optically active column (chiral column), for example ENANTIO-OVM (Toso), and eluting the desired isomer with a solvent or solvents selected from among water, various buffer solutions (e.g. phosphate buffer), and organic solvents such as alcoholic solvents (e.g. methanol, ethanol, etc.), nitrile solvents (e.g. acetonitrile), hexane, ethyl ether, etc.; and a method which comprises causing the racemic mixture to condense with an optically active organic acid, for example MPTA [α-methoxy-α-(trifluoromethyl)phenylacetic acid] or menthoxyacetic acid by a conventional technique such as the acid chloride process to provide a mixture of diastereomers of the amide, fractionating it by a fractional purification technique such as fractional recrystallization or silica gel chromatography, and subjecting it to acid or basic hydrolysis.

While the compound (I) or salt of this invention can be produced by various alternative processes, the processes described hereinafter can be mentioned as typical examples.

The compound (I) of this invention, where it is a free compound, can be converted to a salt by a conventional technique and, where it is a salt, can be converted to the free compound by a conventional technique. The compound (I) or salt thus produced can be isolated and purified by known procedures such as solvent extraction, pH adjustment, redistribution, crystallization, recrystallization and chromatography. Where the compound (I) or salt is optically active, the isomers can be fractionally isolated by the optical resolution techniques described hereinbefore.

The "leaving group" for L is a functional group which is easily displaced by chemical reaction, thus including but being not limited to halogen, methanesulfonyloxy, p-toluenesulfonyloxy, benzenesulfonyloxy and trifluoromethanesulfonyloxy.

The specific solvents that can be used for the above reactions are as follows.

The "ether solvent" includes tetrahydrofuran, ethyl ether, dioxane, isopropyl ether, 1,2-dimethoxyethane and so on;

The "halogenated hydrocarbon solvent" includes dichloromethane, 1,2-dichloroethane, chloroform, carbon tetrachloride and so on.

The "aromatic hydrocarbon solvent" includes benzene, toluene, xylene and so on.

The "alcoholic solvent" includes methanol, ethanol, isopropyl alcohol, tert-butanol, ethylene glycol, sec-butanol and so on.

<Production Process 1> Synthesis of an Isochroman-form Derivative

The compound (I) wherein X is an oxygen atom can be synthesized by the following process.

[Step 1] Synthesis of diol derivative (5) (cf. the flow chart of the production process 1 hereinafter)

A substituted phenylacetonitrile derivative (1) is reacted with an acrylic ester (e.g. methyl acrylate or ethyl acrylate) or

L—(CH$_2$)$_{m-1}$—CO$_2$—J wherein L represents a leaving group; J represents lower (C$_{1-6}$) alkyl, such as methyl or ethyl, in an inert solvent or mixed solvent, e.g. an ether solvent, N,N-dimethylformamide (DMF), dimethyl sulfoxide (DMSO), acetonitrile, an alcoholic solvent and/or an aromatic hydrocarbon solvent in the presence of a base at −20° C. to 120° C. for 5 minutes to 18 hours to provide an ester derivative (2).

The base that can be used includes strong bases such as sodium hydroxide, potassium t-butoxide, lithium diisopropylamide, etc., inorganic bases such as alkali metal or alkaline earth metal hydroxides, carbonates or bicarbonates, e.g. sodium hydroxide, potassium carbonate, etc., and organic bases such as triethylamine, DBU (1,8-diazabicyclo [5,4,0]-7-undecene) and so on.

Particularly in the reaction with an acrylic ester, the objective derivative can be produced by conducting the reaction with 1 to 5 equivalents of the acrylic ester in an alcohol, e.g. ethanol, in the presence of a catalyst amount to 5 equivalents of DBU under heating at 40° C. to 100° C. and stirring for 1 to 3 hours.

Where a bromoacetic ester is used, the objective derivative can be produced by conducting the reaction in an ether solvent, e.g. tetrahydrofuran (THF) in the presence of 1 to 3 equivalents of a strong base, e.g. sodium hydride, at 0° C. to 20° C. for 5 minutes to 20 hours.

The ester derivative (2) can be converted to the diol compound by a combination of reduction and acid hydrolysis. Thus, using not less than 3 equivalents of a metal hydride (e.g. lithium aluminum hydride, diisobutylaluminum hydride, diborane, etc.) in a solvent, such as an ether solvent (e.g. THF, ethyl ether, etc.) or an aromatic hydrocarbon solvent (e.g. toluene), the ester residue is reduced to hydroxymethyl and, at the same time, the cyano group is reduced to iminoalcohol (3). When lithium aluminum hydride, for instance, is employed, the reaction temperature is preferably 0° C. to 20° C. and the reaction time 0.5 to 2 hours.

The resulting iminoalcohol (3) is subjected, without purification, to acid hydrolysis and further to reduction, whereby it is converted to the diol (5). The acid hydrolysis of iminoalcohol (3) can be accomplished by heating and stirring the imminoalcohol in a solvent mixture of water and either an inorganic acid, e.g. hydrochloric acid, sulfuric acid or the like, or an organic acid such as acetic acid, trifluoroacetic acid or the like at 20° C. to 100° C. for 30 minutes to 25 hours. Preferably, (3) is treated in 2N-hydrochloric acid under heating at 50° C. and stirring for 5 to 24 hours.

The reduction reaction mentioned above can be the ordinary reduction reaction using a metal hydride which is preferably lithium aluminum hydride or sodium borohydride. In the case of lithium aluminum hydride, the reaction is carried out in an ether solvent at 0° C. to 30° C. for 30 minutes to 2 hours.

On the other hand, the diol compound can also be obtained with ease by reducing the γ-butyrolactone compound (6) with, for example, a metal hydride. This reduction can be accomplished by the technique described in detail by Richard C. Larock's Comprehensive Organic Transformation.

Taking α,α-diphenyl-γ-lactone (m=2) as an example, the corresponding diol compound (5) can be obtained in good yield by treating the lactone with 2 to 10 equivalents of lithium aluminum hydride in an ether solvent (e.g. THF, ethyl ether) at −20° C. to 50° C. for 0.5 to 5 hours.

[Step 2] Construction of the Isochroman Nucleus

Cyclization of the diol (5) can be achieved by using formalin or a formaldehyde polymer, e.g. paraformaldehyde, in the presence of an organic acid, e.g. trifluoroacetic acid or methanesulfonic acid, or an inorganic acid, e.g. sulfuric acid, optionally in an inert solvent such as a halogenated hydrocarbon solvent (e.g. dichloromethane, dichloroethane, etc.) and conducting the reaction at 10° C. to 100° C. for 10 minutes to 18 hours. The formaldehyde polymer may be used in excess and is preferably used in a proportion of 1 to 10 equivalents.

[Step 3] Introduction of

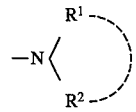

The hydroxyl group of isochroman derivative (7) can be easily converted to a leaving group [Compound (8)]. The preferred leaving group is tosyloxy or halogen, e.g. bromine, iodine or the like. This conversion reaction can be carried out by the per se known technique (e.g. the techniques described in Comprehensive Organic Transformation referred to above). For example, the conversion to tosyloxy can be achieved by reacting (7) with p-toluenesulfonyl chloride (1 to 2 equivalents) in the presence of an organic base (1 to 5 equivalents), e.g. triethylamine, in a halogenated hydrocarbon solvent (e.g. dichloroethane, dichloromethane, etc.) at 0° C. to 30° C. The iodo-compound can be obtained by reacting the tosyl compound with sodium iodide (1 to 5 equivalents) in an inert solvent. Preferably the reaction temperature is 10° C. to 60° C. and the reaction time is 10 minutes to 5 hours. The particularly preferred inert solvent is acetone, methyl ethyl ketone or the like.

The objective compound of this invention can be synthesized by using the corresponding amine

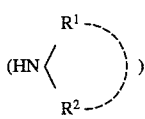

and conducting the reaction in the absence or presence of an inert solvent (e.g. acetonitrile, DMF, acetone or an alcoholic solvent) at 10° C. to 100° C. for 1 to 24 hours. The preferred proportion of HN-$R^1R^2$ is 1 to 3 equivalents and this reaction can be conducted smoothly in the presence of an inorganic base, e.g. potassium carbonate, or an organic amine, e.g. triethylamine. While the type and amount of the base may vary with different amines, the base is preferably used in a proportion of 2 to 4 equivalents.

Production Process 1

[Step 4] Synthesis of Aminoalcohol (10)

The aminoalcohol (10) can be obtained by subjecting the cyano ester (2) obtained in the course of Step 1 to direct reduction or the iminoalcohol (3) to reduction reaction.

In the process for direct reduction of cyano ester (2), the cyano ester derivative (2) is treated with not less than 4 equivalents of a metal hydride (e.g. lithium aluminum hydride, diisobutylaluminum hydride, diborane, sodium borohydride, etc.), optionally in the presence of aluminum chloride, cobalt chloride or the like, in an ether solvent (e.g. THF, ethyl ether, etc.) or an aromatic hydrocarbon solvent (e.g. toluene). When lithium aluminum hydride (4 to 10 equivalents) is used, the reaction temperature is preferably 20° C. to 80° C. and the reaction time is preferably 0.5 to 12 hours.

The same reaction conditions can be applied to the reduction of iminoalcohol (10).

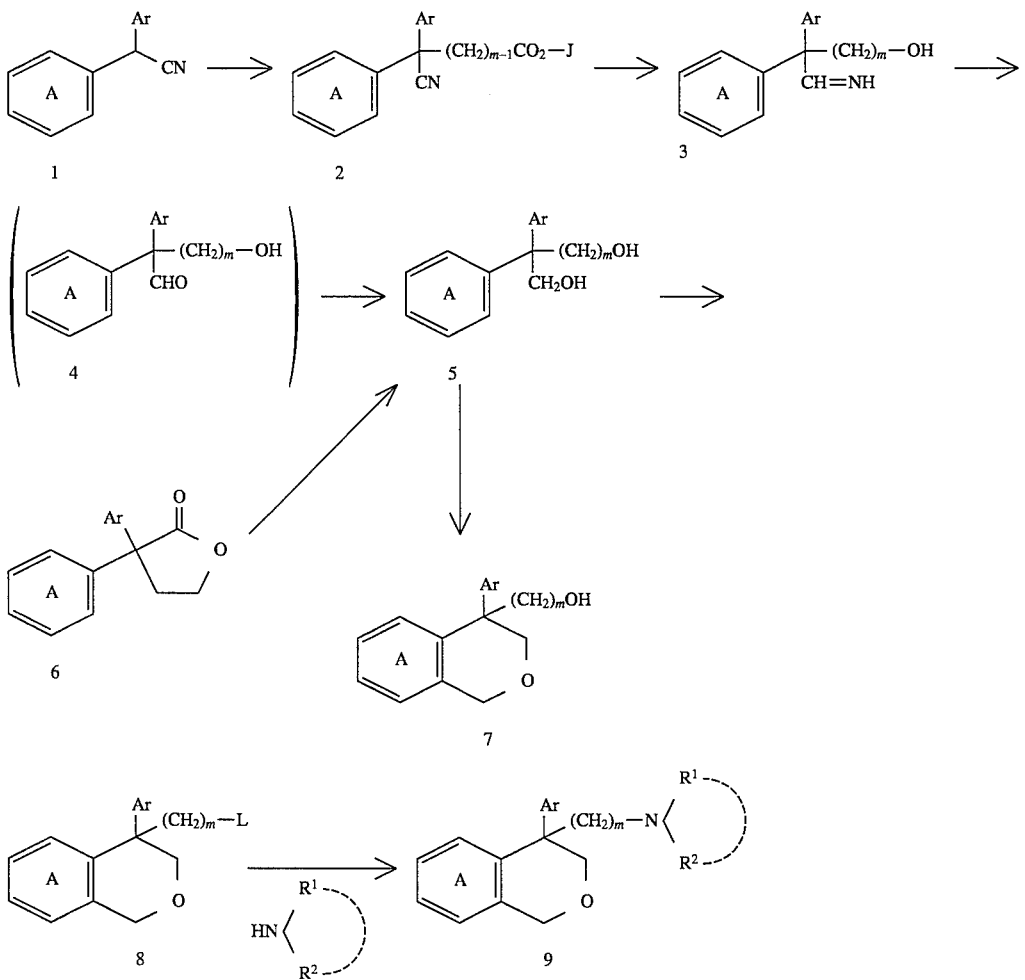

<Production process 2> Synthesis of an
Isoquinoline-form Derivative

The compound in which X represents —$NR^3$— or a nitrogen atom can be synthesized by the following process.

[Step 5] Formylation of the Amino Group and Introduction of

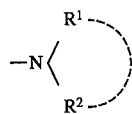

The amino group of the aminoalcohol (10) is selectively formylated by treating (10) with a formic acid-lower fatty acid anhydride system and subsequent basification to obtain compound (11). This formylation reaction proceeds easily as the starting compound (10) is dissolved in an excess (3 to 10 equivalents) of formic acid and 1 to 1.5 equivalents of a fatty acid anhydride and stirred at 0° C. to 30° C. for 1 to 24 hours. In the subsequent basification step, the product is dissolved in an alcoholic solvent and stirred together with, for example, an alkali metal or alkaline earth metal hydroxide (1 to 5 equivalents) at 0° C. to 40° C. for 0 minutes to 5 hours. This procedure gives the formamide (11).

The conversion of hydroxyll to a leaving group and the introduction of

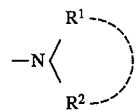

can be carried out as described in Step 3.

[Step 6] Formation of the Insoquinolene Ring

Formation of the isoquinoline ring can be accompolished by acid catalysis reaction. While a variety of acid catalysts can be used, polyphosphoric acid is particularly preferred.

Thus, the formamide (13) and an excess (5 to 100 equivalents) of polyphosphoric acid are heated together at 100° C. to 200° C. with stirriing for 1 to 5 hours, whereby the dihydroisoquinoline compound (14) is obtained.

The conversion to the tetrahydroisoquinoline compound (15) can be achieved by the per se known reduction reaction (e.g. the process using a metal hydride or the catalytic reduction using a metal catalyst).

The reduction reaction using a metal hydride cab be achieved by stirring the starting compound together with lithium aluminum hydride, sodium borohydride, diborane, lithium borohydride or the like (1~10 equivalents) in an alcoholic solvent or an ether solvent at −20° C. to 40° C. for 5 minutes to 5 hours.

Where a catalytic reduction process using a metal catalyst is adopted, the reduction can be conducted using Raney nickel, platinum oxide, palladium metal, palladium-on-carbon or the like in an alconolic solvent or an ether solvent at 10° C. to 100° C. and a hydrogen pressure of not less than 1 atmosphere for 1 to 18 hours. The preferred hydrogen pressure is 1 to 10 atmospheres.

[Step 7]

Introduction of substituent group $R^3$ to the ring nitrogen atom of tetrahydroisoquinoline derivative (15) can be achieved by the per se known methods.

The introduction of an alkyl group, for instance, can be achieved by using an alkyl halide or by reductive alkylation using an alkylaldehyde.

Taking reductive alkylation as an example, the reaction can be accomplished by using an excess (1 to 10 equivalents) of formalin or an alkylaldehyde (1 to 10 equivalents) in an alcoholic solvent in the presence of Raney nickel, platinum oxide, palladium metal, palladium-on-carbon or the like at 10° C. to 100° C. and a hydrogen pressure of not less than 1 atmosphere for 1 to 18 hours. The preferred range of hydrogen pressure is 1 to 10 atmospheres.

Referring to the reaction with an alkyl halide, the alkyl compound can be synthesized using an alkali metal or alkaline earth metal hydroxide, carbonate or bicarbonate (e.g. potassium carbonate, sodium carbonate, sodium hydroxide, potassium hydroxide, etc.) or a strong base (e.g. sodium hydride, lithium hydride, etc.) in acetonitrile, DMF and/or an ether solvent at a temperature of 10° to 100° C. for 1 to 100 hours.

In the case of acylation or carbamoylation, the reaction with the corresponding isocyanate or acyl chloride is conducted in a halogenated hydrocarbon solvent (e.g. dichloromethane, dichloroethane, chloroform, etc.) at a reaction temperature of −20° C. to 50° C. for 5 minutes to 24 hours. This reaction may be conducted in the presence of an organic base, e.g. triethylamine, or an inorganic base, e.g. an alkali metal or alkaline earth metal hydroxide, carbonate or bicarbonate (e.g. potassium carbonate, sodium carbonate, sodium hydroxide, potassium hydroxide, etc.) (a catalyst amount to 10 equivalents).

For the functional transformation or modification of

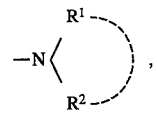

various per se known reactions such as oxidation, reduction, alkylation and acylation can be carried out in combination to provide other derivatives.

<Production process 2>

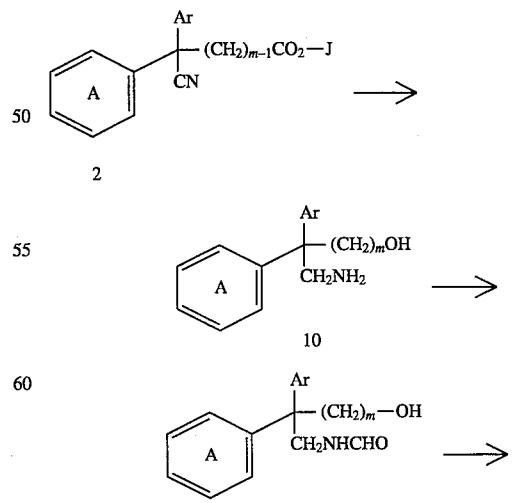

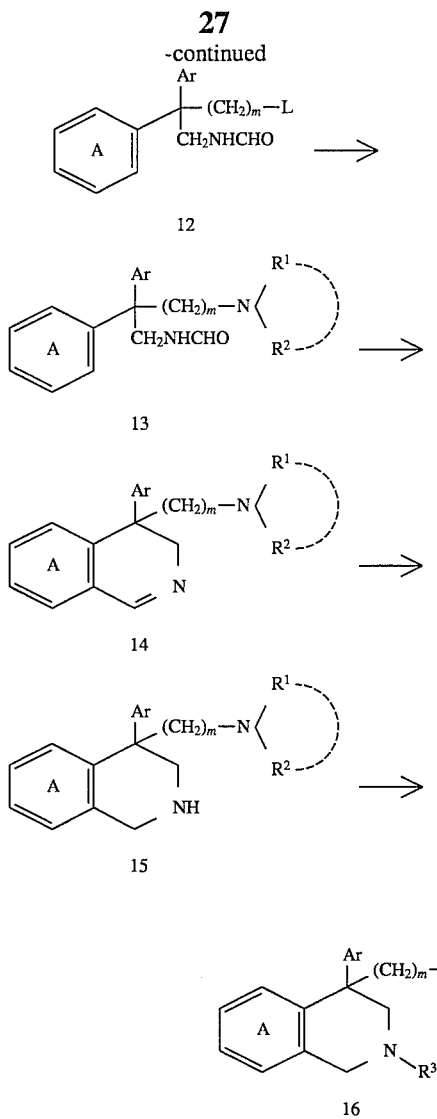

The various starting compounds and salts for the objective compound (I) of this invention can be respectively isolated and purified by known procedures such as solvent extraction, pH adjustment, redistribution, salting-out, crystallization, recrystallization and chromatography but each reaction mixture containing the corresponding compound or salt may be directly submitted to the next reaction step.

In the respective reactions according to the invention and the respective reactions for synthesizing the starting or intermediate compounds, where any of such compounds has an amino, carboxyl and/or hydroxy group, such groups may be previously protected with an appropriate protective group that is commonly used in peptide or other chemistry and the objective compound can be ultimately obtained by removing the protective group as required.

The protective group that can be used for protection of the amino group includes but is not limited to $C_{1-6}$ alkyl-carbonyl (e.g. formyl, acetyl, ethylcarbonyl, etc.), $C_{1-6}$ alkyloxycabonyl (e.g. methoxycarbonyl, ethoxycarbonyl, etc.), benzoyl, $C_{7-10}$ arakyl-carbonyl (e.g. benzylcarbonyl etc.), trityl, phthaloyl and, N,N-dimethylaminomethylene. These groups may respectively have 1–3 substituents, e.g. halogen (e.g. fluorine, chlorine, bromine, iodine), and nitro.

The protective group that can be used for protection of the carboxyl function includes but is not limited to $C_{1-6}$ alkyl (e.g. methyl, ethyl, n-propyl, isopropyl, butyl, tert-butyl, etc.), phenyl, trityl and silyl. These groups may respectively have 1–3 substituent groups such as halogen (e.g. fluorine, chlorine, bromine and iodine), $C_{1-6}$ alkyl-carbonyl (e.g. formyl, acetyl, ethylcarbonyl, butylcarbonyl, etc.) and nitro.

The protective group that can be used for protection of the hydroxy function includes but is not limited to $C_{1-6}$ alkyl (e.g. methyl, ethyl, n-propyl, isopropyl, butyl, tert-butyl, etc.), phenyl, $C_{7-10}$ aralkyl (e.g. benzyl), $C_{1-6}$ alkyl-carbonyl (e.g. formyl, acetyl, ethylcarbonyl, etc.), benzoyl, $C_{7-10}$ aralkylcarbonyl (e.g. benzylcarbonyl etc.), tetrahydropyranyl, tetrahydrofuranyl and silyl. These groups may respectively have 1–3 substituent groups such as halogen (e.g. fluorine, chlorine, bromine and iodine), $C_{1-6}$ alkyl (e.g. methyl, ethyl, n-propyl, etc.), phenyl, $C_{7-10}$ aralkyl (e.g. benzyl) and nitro.

While these protective groups can be removed by various methods known per se or analogous therewith, the procedures using an acid, a base, ultraviolet light, hydrazine, phenylhydrazine, sodium N-methyldithiocarbamate, tetrabutylammonium fluoride and palladium acetate, respectively, can be selectively utilized.

The compound (I) or its pharmaceutically acceptable salt of this invention, on administration to man and other mammalian animals (e.g. mouse, rat, rabbit, dog, bovine, swine, etc.), inhibits secretion of gonadotropin to modulate blood steroid hormone levels, thanks to its GnRH receptor antagonizing activity, so that it can be safely used for the ovulation inhibitor, prevention agent for implantation of the ovum or the prophylactic and therapeutic agent for various diseases such as amenorrhea, prostatic cancer, prostatic hypertrophy, endometriosis, hysteromyoma, breast cancer, acne, precocious puberty, premenstrual syndrome, polycystic ovary syndrome, pituitary tumor and hyperandrogenism in humans.

The compound (I) or its pharmaceutically acceptable salt of this invention can be safely used for a contaceptive for female or male, an ovulation-inducing agent for female, an estrus regulator in animals, an improvement of quality of the edible meats, a growth promotor in animals or an oviposition promotor in fish.

The compound (I) or its pharmaceutically acceptable salt of this invention can be effectively used together with a sterolidal or non-stroidal antiandrogen agent.

The compound (I) and pharmaceutically acceptable salt of this invention have activity to antagonize monoamines uptake by synapses and an excessive calcium ion influx into neurons in man and other mammalian animals (e.g. mouse, rat, rabbit, dog, cattle, swine, etc.) and can be used safely in the prevention and treatment of various diseases inclusive of emotional disturbances such as depression, anxiety, alcohol dependence, appetite disorder, panic attack, obsession syndrome, etc., neurodegenerative diseases such as Parkinson's disease, Alzheimer's disease, etc., epilepsy, convulsion, and cerebrovascular disorders such as cerebral apoplexy, cerebral infarction, etc. particularly in humans.

The compound (I) or salt of this invention features a low toxic potential and a low risk of side effect. The oral acute toxicity ($LD_{50}$) of the compound in rats is not less than 100 mg/kg.

The compound (I) or salt of this invention can be safely administered orally or otherwise in its neat form or in the form of a pharmaceutical composition which can be prepared by the per se known pharmaceutical technology using medicinally acceptable carriers, for example tablets (inclusive of dragees, film-coated tablets, etc.), powders, granules, capsules (inclusive of soft capsules), elixirs, injections, suppositories, controlled-release tablets and other drug delivery systems. The dosage depends on the subject, route of administration, type of disease and other factors. However, taking the oral treatment of cerebral apoplexy as an example, the recommended daily dosage for an average adult (b. w. 60 kg) is 0.1 to 500 mg, preferably 10 to 100 mg, which dosage can be administered in a single dose or in a few divided doses daily.

The pharmaceutically acceptable carrier that can be used includes those organic and inorganic carriers which are commonly used in the pharmaceutical field, including excipients, lubricants, binders, disintegrators, etc. for solid compositions and solvents, solubilizers, suspending agents, isotonizing agents, buffers, local anesthetics, etc. for liquid compositions. Where necessary, various additives such as preservatives, antioxidants, coloring agents, sweeteners, etc. can also be employed. The preferred excipient includes lactose, sucrose, D-mannitol, starch, crystalline cellulose, light silicic anhydride, etc. The preferred lubricant includes magnesium stearate, calcium stearate, talc and colloidal silica, among others. The preferred binder includes crystalline cellulose, sucrose, D-mannitol, dextrin, hydroxypropylcellulose, hydroxypropylmethylcellulose and polyvinylpyrrolidone, among others. The preferred disintegrator includes starch, carboxymethylcellulose, carboxymethylcellulose calcium, croscarmellose sodium, carboxymethylstarch sodium and so on. The preferred solvent includes water for injection, alcohols, propylene glycol, macrogols, sesame oil and corn oil, among others. The preferred solubilizer includes but is not limited to polyethylene glycol, propylene glycol, D-mannitol, benzyl benzoate, ethanol, trisaminomethane, cholesterol, triethanolamine, sodium carbonate and sodium citrate. The preferred suspending agent includes various surfactants such as stearyltriethanolamine, sodium lauryl sulfate, laurylaminopropionic acid, lecithin, benzalkonium chloride, benzethonium chloride, glyceryl monostearate, etc. and various hydrophilic macromolecular substances such as polyvinyl alcohol, polyvinylpyrrolidone, carboxymethylcellulose sodium, methylcellulose, hydroxymethylcellulose, hydroxyethylcellulose, hydroxypropylcellulose and so on. The preferred isotonizing agent includes but is not limited to sodium chloride, glycerin and D-mannitol. The preferred buffer includes phosphate, acetate, carbonate and citrate buffer solutions, among others. The preferred local anesthetic includes benzyl alcohol, among others. The preferred preservative includes but is not limited to p-hydroxybenzoic acid esters, chlorobutanol, benzyl alcohol, phenethyl alcohol, dehydroacetic acid, sorbic acid and so on. The preferred antioxidant includes sulfites, ascorbic acid and so on.

The compound (I) or salt of this invention, thanks to its GnRH receptor antagonizing activity, inhibits secretion of gonadotropin in mammals to control blood steroidal sex hormone levels and, particularly in man, can display efficacy in the prophylaxis and therapy of various diseases.

Typical examples of its application are inhibition of ovulation or of implantation of the ovum in mammalian animals and the prevention and treatment of amenorrhea, prostatic cancer, prostatic hypertrophy, endometriosis, breast cancer, acne, premature puberty, premenstrual syndrome, polycystic ovary syndrome and hyperandrogenism.

In addition, the compound (I) or salt of this invention is useful for the improvement of meat quality.

The GnRH receptor antagonist composition of this invention, when used in combination with a GnRH receptor agonist in mammalian animals, particularly female animals, enables the endogenic gonadotropin level to be controlled and maintained at the proper level and can provide an effective therapeutic modality for induction of ovulation.

The objective compound (I) and salt of this invention have also activity to antagonize the synaptic uptake of monoamines such as norepinephrine (NE) and serotonine (5-HT) and the excessive influx of calcium ion and, therefore, can be safely used in the prevention and treatment of various diseases inclusive of emotional disturbances such as depression, anxiety, alcohol dependence, appetite disorder, panic stroke, obsession syndrome, etc., neurodegenerative diseases such as Parkinson's disease, Alzheimer's disease, etc., epilepsy, convulsion, and cerebrovascular disorders such as cerebral apoplexy, cerebral infarction, etc. and brain damage due to a traffic accident particularly in humans.

The following reference examples, examples and experimental examples are intended to describe this invention in further detail. It should be understood that these examples are merely illustrative and by no means limitative of the invention and that many changes and modifications can be made without departing from the spirit and scope of the invention.

The term "room temperature" as used in the following reference examples and examples means the range of 0°–30° C. The meanings of the various symbols used are as follows.

s: singlet d: doublet t: triplet q: quartet m: multiplet br: broad

J: coupling constant

Hz: Herz $CDCl_3$: deuterochloroform

THF: tetrahydrofuran

DMF: N,N-dimethylformamide

DMSO: dimethyl sulfoxide $^1$H-NMR: proton nuclear magnetic resonance spectrum (NMR spectra was measured by the free form.)

REFERENCE EXAMPLE 1-1

2-(p-Fluorophenyl)-2-phenylacetonitrile

A solution of p-fluoromandelonitrile (45 g) in benzene (90 g) was added portionwiste to sulfuric acid (85 ml) with constant stirring at 5°–10° C. After completion of portionwise addition, the mixture was further stirred for 30 minutes. The reaction mixture was then diluted with water (500 ml) and extracted with ethyl acetate (300 ml×2). The extract was washed with water, dried over anhydrous sodium sulfate and concentrated to provide a colorless oil (59.5 g).

Using the corresponding mandelonitrile derivative and chlorobenzene, the following compounds 1–2 and 1–3 were respectively synthesized in otherwise the same manner as Reference Example 1–1.

Compound 1–2

2-(p-Chlorophenyl)-2-phenylacetonitrile

Compound 1–3

Bis(p-chlorophenyl)acetonitrile

The structural formulas, physical properties and NMR spectra of the above compounds are shown in Table 1.

TABLE 1

Ar–CH(CN)–C₆H₃(R⁰)–

| Reference Example | R⁰ | Ar | $^1H$–NMR ($\delta_{ppm}$, $CDCl_3$) |
|---|---|---|---|
| 1-1 | H | C₆H₄-F | 5.13(1H, s), 7.00–7.50(9H, m) |
| 1-2 | H | C₆H₄-Cl | 5.11(1H, s), 7.23–7.42(9H, m) |
| 1-3 | p-Cl | C₆H₄-Cl | 5.10(1H, s), 7.20–4.20(8H, m) |

REFERENCE EXAMPLE 2-1

Ethyl 3-cyano-3,3-diphenylpropionate

To a solution of diphenylacetonitrile (1 g) in tetrahydrofuran (10 ml) was added 60% sodium hydride (0.25 g) portionwise under ice-cooling and stirring. After completion of portionwise addition, the mixture was further stirred for 15 minutes. Then, ethyl bromoacetate (0.69 ml) was added dropwise and the mixture was further stirred for 30 minutes. The reaction mixture was then diluted with water and the organic layer was extracted with ethyl acetate. The extract was washed with water, dried over anhydrous sodium sulfate and concentrated to dryness. The residue was purified by silica gel chromatography (hexane/ethyl acetate) to provide the title compound (1.2 g) as colorless powder.

REFERENCE EXAMPLE 2-2

Ethyl 4-cyano-4,4-diphenylbutyrate

To an ethanolic solution (100 ml) of diphenylacetonitrile (28 g) were added DBU (6 ml) and ethyl acrylate (30 ml) and the mixture was heated and stirred at 80° C. for 16 hours. After cooling, 200 ml of 2N-hydrochloric acid was added to the reaction mixture, which was then extracted with isopropyl ether. The organic layer was washed with water, dried (anhydrous magnesium sulfate) and concentrated under reduced pressure. The resulting crude crystals were recrystallized from hexane/isopropyl ether to provide ethyl 4-cyano-4,4-diphenylbutyrate (34 g).

In the same manner as above, the reference compounds 2-3~6 were synthesized.

Compound 2-3
Ethyl 4-cyano-4-(p-fluorophenyl]-4-phenylbutyrate
Compound 2-4
Ethyl 4-cyano-4-(p-chlorophenyl)-4-phenylbutyrate
Compound 2-5
Ethyl 4-cyano-4,4-bis(p-chorophenyl)butyrate
Compound 2-6
Ethyl 5-cyano-5,5-diphenylpentanoate The structural formulas, physical properties and NMR spectra of these compounds are shown in Table 2.

TABLE 2

R⁰–C₆H₃–C(Ar)(CN)–(CH₂)ₘ₋₁–CO₂C₂H₅

| Reference Example | R⁰ | Ar | m | $^1H$–NMR ($\delta_{ppm}$, $CDCl_3$) |
|---|---|---|---|---|
| 2-1 | H | C₆H₅ | 2 | 1.11(3H, t), 3.42(2H, s), 4.07(2H, q), 7.26–7.43(10H, m) |
| 2-2 | H | C₆H₅ | 3 | 1.23(3H, t), 2.40–2.51(2H, m), 2.71–2.82(2H, m), 4.11(2H, q), 7.26–7.43(10H, m) |
| 2-3 | H | C₆H₄-F | 3 | 1.23(3H, t), 2.43(2H, t), 2.73(2H, t), 4.10(2H, q), 7.00–7.40 (9H, m) |
| 2-4 | H | C₆H₄-Cl | 3 | 1,23(3H, t), 2.38–2.48(2H, m), 2.78–2.78(2H, m), 4.10(2H, q), 7.29–7.40(9H, m) |

TABLE 2-continued $$R^0-\underset{}{\underset{}{\bigcirc}}-\underset{CN}{\overset{Ar}{\underset{|}{C}}}(CH_2)_{m-1}-CO_2C_2H_5$$

| Reference Example | $R^0$ | Ar | m | $^1H$-NMR ($\delta_{ppm}$, CDCl$_3$) |
|---|---|---|---|---|
| 2-5 | p-Cl | –C$_6$H$_4$–Cl | 3 | 1.23(3H, t), 2.41(2H, m), 2.70(2H, m), 4.10(2H, q), 7.20–7.40 (8H, m) |
| 2-6 | H | C$_6$H$_5$ | 4 | 1.24(3H, t), 1.69–1.86(2H, m), 2.38(2H, t), 2.38–2.48(2H, m), 4.12(2H, q), 7.23–7.43(10H, m) |

REFERENCE EXAMPLE 3-1

2,2-Diphenyl-1,4-butanediol

In anhydrous THF (80 ml) was dissolved α,α-diphenyl-γ-butyrolactone (7 g) followed by addition of lithium aluminum hydride (1 g) with ice-cooling, and the mixture was stirred under the same conditions for 3 hours. Then, under ice-cooling, a saturated aqueous solution of Rochelle salt was added dropwise to precipitate the aluminum and other inorganic matter. The supernatant was taken by decantation, dried and concentrated under reduced pressure. The residue was recrystallized from isopropyl ether to provide 2,2-diphenyl-1,4-butanediol (7 g).

REFERENCE EXAMPLE 3-2

2-Diphenyl-1,5-pentanediol

In THF (120 ml) was dissolved ethyl 4-cyano-4,4diphenylbutyrate (24 g) and the solution was added portionwise to a suspension of lithium aluminum hydride (4.2 g) in THF (200 ml) with ice-cooling. The mixture was stirred under ice-cooling for 2 hours, at the end of which time 2N-hydrochloric acid (200 ml) was added and the mixture was heated and stirred at 60° C. for 2 hours. Then, ethyl acetate (400 ml) was added to the reaction mixture and the organic layer was separated, stirred and concentrated under reduced pressure. The residue was dissolved in THF (200 ml) followed by addition of lithium aluminum hydride (4 g) with ice-cooling. The mixture was stirred under the same conditions for 2 hours, after which a saturated aqueous solution of Rochelle salt was added to the reaction mixture under ice-cooling to precipitate the aluminum and other inorganic matter. The supernatant was taken by decantation, dried and concentrated under reduced pressure. The residue was recrystallized from isopropyl ether/ethyl acetate to provide 2-diphenyl-1,5-pentanediol (20.5 g).

In the same manner as Reference Example 3-2, the following compounds 3-3~6 were synthesized.

Compound 3-3
2-(p-Fluorophenyl)-2-phenyl-1,5-pentanediol

Compound 3-4
2-(p-Chlorophenyl)-2-phenyl-1,5-pentanediol

Compound 3-5
2,2-Bis(p-chlorophenyl)-1,5-pentanediol

Compound 3-6
2,2-Diphenyl-1,6-hexanediol

The structural formulas, physical properties and NMR spectra of the above compounds are shown in Table 3.

TABLE 3

$$R^0-\underset{}{\underset{}{\bigcirc}}-\underset{(CH_2)_m-OH}{\overset{Ar}{\underset{|}{C}}}\overset{OH}{}$$

| Reference Example | $R^0$ | Ar | m | $^1H$-NMR ($\delta_{ppm}$, CDCl$_3$) |
|---|---|---|---|---|
| 3-1 | H | C$_6$H$_5$ | 2 | 2.54(2H, t), 3.61(2H, t), 4.21(2H, s), 7.16–7.45(10H, m) |
| 3-2 | H | C$_6$H$_5$ | 3 | 1.28–1.42(2H, m), 2.19–2.30(2H, m), 3.59(2H, t), 4.17(2H, s), 7.15–7.37 (10H, m) |

TABLE 3-continued $$R^0-\underset{}{\underset{}{\bigcirc}}-\underset{(CH_2)_m-OH}{\overset{Ar}{\underset{|}{C}}-OH}$$

| Reference Example | $R^0$ | Ar | m | $^1H-NMR$ ($\delta_{ppm}$, $CDCl_3$) |
|---|---|---|---|---|
| 3-3 | H | —⟨○⟩—F | 3 | 1.32(2H, m), 2.22(2H, m), 3.59(2H, t), 4.13(2H, s), 6.90–7.40(9H, m) |
| 3-4 | H | —⟨○⟩—Cl | 3 | 1.20–1.40(2H, m), 1.95(2H, br s), 2.22(2H, m), 3.58(2H, t), 4.12(2H, s), 7.00–7.40(9H, m) |
| 3-5 | p-Cl | —⟨○⟩—Cl | 3 | 1.20–1.40(2H, m), 2.20(2H, m), 3.60(2H, t), 4.10(2H, s), 7.00–7.30(9H, m) |
| 3-6 | H | —⟨○⟩ | 4 | 1.03–1.21(2H, m), 1.42–1.61(2H, m), 1.52(1H, t), 1.63(1H, br s), 2.12–2.22 (2H, m), 3.54(2H, br t), 4.15(2H, d), 7.12–7.35(10H, m) |

REFERENCE EXAMPLE 4-1

4-(2-Hydroxyethyl)-4-phenylisochroman

In trifluoroacetic acid (50 ml) was dissolved 2,2-diphenyl-1,4-butanediol (5 g) followed by addition of paraformaldehyde (1.7 g) and the mixture was heated and stirred at 50° C. for 2 hours. The reaction mixture was then concentrated under reduced pressure and the residue was dissolved in ethyl acetate, washed with saturated aqueous sodium hydrogen carbonate solution and concentrated under reduced pressure. The residue was dissolved in ethanol (100 ml) followed by addition of sodium hydroxide (4 g) and water (50 ml) and the mixture was stirred at room temperature for 1 hour. After concentration under reduced pressure, the residue was dissolved in ethyl acetate, washed with water, dried and concentrated under reduced pressure. The residue was purified by silica gel column chromatography using isopropyl ether/ethyl acetate as the eluent to provide 4-(2-hydroxyethyl)-4-phenylisochroman (4.5 g).

In the same manner as Reference Example 4-1, the following Reference Example Compounds 4-2~6 were synthesized.

Compound 4-2
4-(3-Hydroxypropyl)-4-phenylisochroman
Compound 4-3
4-(p-Fluorophenyl)-4-(3-hydroxypropyl)isochroman
Compound 4-4
4-(p-Chlorophenyl)-4-(3-hydroxypropyl)isochroman
Compound 4-5
7-Chloro-4-(p-chlorophenyl)-4-(3-hydroxypropyl)isochroman
Compound 4-6
4-(4-Hydroxybutyl)-4-phenylisochroman The 'structural formulas, physical properties and NMR spectra of the respective compounds are shown in Table 4.

TABLE 4

| Reference Example | R⁰ | Ar | m | Melting Point (°C.) | $^1$H—NMR ($\delta_{ppm}$, CDCl$_3$) |
|---|---|---|---|---|---|
| 4-1 | H |  | 2 | Syrup | 2.26–2.39(1H, m), 2.68(1H, ddd), 3.38(1H, ddd), 3.52–3.67(1H, m), 3.85(1H, dd), 4.08(1H, d), 4.91(2H, s), 6.86(1H, dd), 7.04–7.38 (9H, m) |
| 4-2 | H | 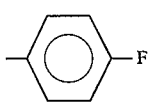 | 3 | Syrup | |
| 4-3 | H | 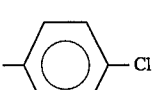—F | 3 | Syrup | 1.40–1.70(2H, m), 2.23(2H, m), 3.63(2H, t), 3.89(2H, s), 4.87(2H, s), 6.90–7.30(8H, m). |
| 4-4 | H | 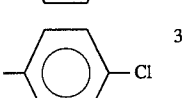—Cl | 3 | Syrup | 1.40–1.70(2H, m), 2.23(2H, m), 3.63(2H, t), 3.89(2H, s), 4.86(2H, s), 6.90–7.30(8H, m). |
| 4-5 | 7-Cl | —Cl | 3 | Syrup | 1.40–1.70(2H, m), 2.22(2H, m), 3.59(2H, t), 3.86(2H, s), 4.82(2H, s), 6.88(1H, d), 7.00–7.30(6H, m). |
| 4-6 | H |  | 4 | Syrup | 1.23–1.48(3H, m), 1.49–1.65(2H, m), 2.07–2.36(2H, m), 3.58(2H, br t), 3.91, 4.87(2H each, s), 6.94–7.34(9H, m) |

REFERENCE EXAMPLE 5-1

4-(2-Iodoethyl)-4-phenylisochroman

In dichloromethane (20 ml) was dissolved 4-(2-hydroxyethyl)-4-phenylisochroman (1 g), followed by addition of tosyl chloride (0.85 g) and triethylamine (1.5 ml) with ice-cooling. The mixture was stirred at room temperature for 2 hours, after which 2N-hydrochloric acid was added and the mixture was extracted with isopropyl ether. The organic layer was washed with water, dried and concentrated under reduced pressure. The residue was dissolved in acetone (50 ml) and after addition of sodium iodide (2 g) the solution was heated and stirred at 50° C. for 24 hours. After cooling, the reaction mixture was diluted with water and extracted with isopropyl ether and the organic layer was washed with water, dried and concentrated under reduced pressure. The residue was applied to a silica gel column and eluted with isopropyl ether to provide 4-(2-iodoethyl)-4-phenylisochroman as oil.

In the same manner as Reference Example 5-1, the following Reference Example Compounds 5-2~6 were synthesized.

Compound 5-2

4-(3-Iodopropyl)-4-phenylisochroman

Compound 5-3

4-(p-Fluorophenyl)-4-(3-iodopropyl)isochroman

Compound 5-4

4-(p-Chlorophenyl)-4-(3-iodopropyl)isochroman

Compound 5-5

7-Chloro-4-(p-chlorophenyl)-4-(3iodopropyl)isochroman

Compound 5-6

4-(4-Iodobutyl)-4-phenylisochroman

The structural formulas, physical properties and NMR spectra of the respective compounds are shown in Table 5.

TABLE 5

Structure: R⁰—[isochroman with Ar, (CH₂)ₘ—L substituents at position with O]

| Reference Example | R⁰ | Ar | L | m | Melting Point (°C.) | ¹H—NMR ($\delta_{ppm}$, CDCl₃) |
|---|---|---|---|---|---|---|
| 5-1 | H | phenyl | I | 2 | Syrup | 2.76–3.08(3H, m), 3.20–3.39(1H, m), 3.89(2H, q), 4.87(2H, s), 6.90(1H, d), 7.01–7.38(8H, m) |
| 5-2 | H | phenyl | I | 3 | 39–40 | 1.50–2.00(2H, m), 2.29(2H, m), 3.16(2H, dt), 3.90(2H, s), 4.88(2H, s), 6.90–7.30(9H, m) |
| 5-3 | H | 4-F-phenyl | I | 3 | Syrup | 1.60–1.90(2H, m), 2.28(2H, m), 3.16(2H, dt), 3.87(2H, s), 4.86(2H, s), 6.90–7.30(8H, m). |
| 5-4 | H | 4-Cl-phenyl | I | 3 | Syrup | 1.60–2.00(2H, m), 2.10–2.40(2H, m), 3.16(2H, t), 3.87(2H, s), 4.87(2H, s), 6.90–7.40(8H, m) |
| 5-5 | 7-Cl | 4-Cl-phenyl | I | 3 | Syrup | 1.60–1.90(2H, m), 2.29(2H, m), 3.52(2H, t), 3.84(2H, s), 4.82(2H, s), 6.85(1H, d), 7.00–7.30(6H, m) |
| 5-6 | H | phenyl | I | 4 | Syrup | 1.25–1.66(2H, m), 1.77–1.92(2H, m), 2.05–2.33(2H, m), 3.15(2H, t), 3.91, 4.88(2H each, s), 6.93–7.34(9H, m) |

REFERENCE EXAMPLE 6-1

1-Benzoyl-2-(2-phenylethyl)-2-piperidinecarbonitrile

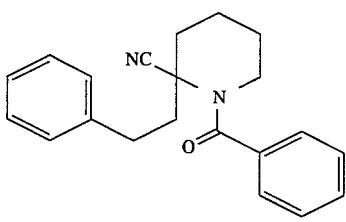

To 200 ml of tetrahydrofuran containing 140 mmol lithium diisopropylamide was added 15 g of solid 1-benzoyl-2-piperidinecarbonitrile at −78° C. The mixture was stirred for 30 minutes, after which 100 ml of tetrahydrofuran containing 33.2 g of phenethyl iodide was added dropwise at −78° C. After completion of dropwise addition, the temperature of the reaction mixture was gradually increased to 0° C. Then, water was added and the organic layer was separated. The aqueous layer was further extracted with ethyl acetate. The pooled organic layer was dried over anhydrous magnesium sulfate and filtered and the solvent was then distilled off. The residue was purified by silica gel column chromatography using ethyl acetate-hexane (1:2) as the eluent. The solution containing the desired compound was distilled under reduced pressure and the resulting solid was recrystallized from ethyl acetate-hexane to provide 17.3 g of colorless crystals.

m.p. 65°–67° C.

¹N-NMR (ppm. CDCl₃) 1.52–2.00 (4H, m), 2.19 (2H, t, J=6Hz), 2.37–2.98 (4H, m), 3.29–3.57 (2H, m), 7.13–7.56 (10H, m)

Elemental analysis for $C_{21}H_{22}N_2O$ Calcd. C 79.21; H 6.96; N 8.80; Found C 79.13; H 6.89; N 8.64

In the same manner as Reference Example 6-1, the following compounds were synthesized.

REFERENCE EXAMPLE 6-2

1-Benzoyl-2-[2-(3-methoxyphenyl)ethyl]-2-piperidinecarbonitrile

REFERENCE EXAMPLE 6-3

1-Benzoyl-2-[2-(3,4-dimethoxyphenyl)ethyl]-2-piperidinecarbonitrile

REFERENCE EXAMPLE 6-4

1-Benzoyl-2-[2-thienylethyl]-2-piperidinecarbonitrile

The structural formulas, physical properties and NMR spectra of the respective compounds are shown in Table 6.

TABLE 6

| Reference Example | Structural Formula | Melting Point (°C.) | NMR (δ_ppm, CDCl₃) | Elemental Analysis [Found/(Calculated)] C H N |
|---|---|---|---|---|
| 6-2 | (structure: 3-methoxyphenethyl piperidine with NO and N-benzoyl) | 82–84 | 1.55–1.98(4H, m), 2.19(2H, t, J=6Hz), 2.36–2.96(4H, m), 3.27–3.57(2H, m), 3.79 (3H, s), 6.71–6.85(3H, m), 7.14–7.25(1H, m), 7.36–7.56(5H, m) | $C_{22}H_{24}N_2O_2$ 75.58 6.98 7.92 (75.83 6.94 8.04) |
| 6-3 | (structure: 3,4-dimethoxyphenethyl piperidine with NO and N-benzoyl) | Oil | 1.54–1.99(4H, m), 2.19(2H, t, J=6Hz), 2.34–2.94(4H, m), 3.27–3.56(2H, m), 3.85 (3H, s), 3.87(3H, s), 6.72–6.83(3H, m), 7.37–7.58(5H, m) | $C_{23}H_{26}N_2O_3$ 73.21 7.16 7.35 (72.99 6.92 7.40) |
| 6-4 | (structure: thienylethyl piperidine with CN and N-benzoyl) | Oil | 1.50–1.97(4H, m), 2.17(2H, t, J=6Hz), 2.45–2.80(2H, m), 2.92–3.22(2H, m), 3.29–3.58(2H, m), 6.83–6.87(1H, m), 6.92(1H, dd, J=4.5Hz), 7.13(1H, dd, J=2, 5=Hz), 7.37–7.58(5H, m) | $C_{19}H_{29}N_2OS$ 70.25 6.07 8.43 (70.34 6.21 8.63) |

REFERENCE EXAMPLE 6-5

3,4-Dihydrospiro[naphthalene-2(1H), 2'-piperidin]-1-one hydrochloride

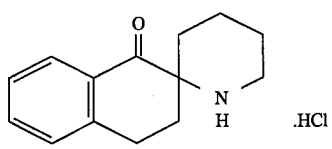

In 250 ml of 1,2-dichloroethane was dissolved 7.64 g of 1-benzoyl-2-(2-phenylethyl)-2piperidinecarbonitrile. Then, 8.0 g of aluminum chloride was added and the mixture was refluxed for 6 hours. The reaction mixture was cooled and poured cautiously into 10% aqueous sodium hydroxide solution. Then, methylene chloride and water were added for extraction. The methylene chloride layer was dried over anhydrous sodium sulfate and filtered and the solvent was distilled off. To the residue were added 100 ml of methanol and 100 ml of 20% aqueous sodium hydroxide solution and the mixture was refluxed for 12 hours. After the reaction mixture was allowed to cool, the methanol was distilled off and methylene chloride and water were added for extraction. The methylene chloride layer was dried over anhydrous sodium sulfate and filtered and the solvent was then distilled off. The residue was purified by alumina column chromatography using an ethyl acetate-hexane solvent system and the eluate containing the desired compound was distilled under reduced pressure. The residue was treated with 6.0 ml of 4N-methanolic HCl to provide a solid. This solid was recrytallized from methylene chloride to provide 3.0 g of colorless crystals.

m.p. 222°–223° C.

$^1$H-NMR (ppm, CDCl₃) 1.37–1.85 (5H, m), 1.92–2.14 (3H, m), 2.44 (1H, dt, J=7Hz, 5Hz), 2.76–3.16 (4H, m), 7.20–7.52 (3H, m), 8.29 (1H, dd, J=8Hz, 1Hz)

Elemental analysis for $C_{14}H_{18}ClNO \cdot H_2O$ Calcd. C 62.33; H 7.47; N 5.19; Found C 62.39; H 7.27; N 5.42

In the same manner as Reference Example 6-5, the following compounds were synthesized.

REFERENCE EXAMPLE 6-6

3,4-Dihydro-6-methoxyspiro[naphthalene-2(1H),2'-piperidin]-1-one hydrochloride

REFERENCE EXAMPLE 6-7

3,4-Dihydro-8-methoxyspiro[naphthalene-2(1H),2'-piperidin]-1-one hydrochloride

REFERENCE EXAMPLE 6-8

3,4-Dihydro-6,7-dimethoxyspiro[naphthalene-2(1H), 2'-piperidin]-1-one hydrochloride

REFERENCE EXAMPLE 6-9

6,7-Dihydrospiro[benzo(b)thiophene-5(4H),2'-piperidin]-4-one hydrochloride

The structural formulas, physical properties and NMR spectra of the respective compounds are shown in Table 7.

TABLE 7

| Reference Example | Structural Formula | Melting Point (°C.) | NMR (δ_ppm, CDCl_3) | Elemental Analysis [Found/(Calculated)] C | H | N |
|---|---|---|---|---|---|---|
| 6-6 | (structure) | 249 (decomposed) | 1.31–1.88(6H, m), 1.89–2.10(1H, m), 2.16(1H, br s), 2.34–2.50(1H, m), 2.74–3.14(4H, m), 3.84(3H, s), 6.66(1H, d, J=3Hz), 6.82(1H, dd, J=9Hz, 3Hz), 7.99(1H, d, J=9Hz) | $C_{15}H_2OClNO_2$ 64.04 (63.94 | 7.20 7.15 | 5.03 4.97) |
| 6-7 | (structure) | 255–259 (decomposed) | 1.42–2.21(6H, m), 2.74–2.85(2H, m), 3.05–3.19(2H, m), 3.36–3.55(1H, m), 3.76–4.00(1H, m), 3.88(3H, s), 6.81 (2H, t, J=8Hz), 7.42(1H, t, J=8Hz), 9.06(1H, br s) | $C_{15}H_{20}ClNO_2 \cdot 1/4H_2O$ 63.02 (62.93 | 7.08 7.22 | 4.91 4.89) |
| 6-8 | (structure) | 245–248 (decomposed) | 1.33–1.85(5H, m), 1.93–2.10(1H, m), 2.35(1H, br s), 2.42(1H, t, J=5Hz), 2.50(1H, t, J=5Hz), 2.76–3.35(4H, m), 3.92(3H, s), 3.93(3H, s), 6.64(1H, s), 7.50(1H, s) | $C_{15}H_{22}ClNO_3 \cdot 1/4H_2O$ 61.01 (60.75 | 7.10 7.17 | 4.51 4.43) |
| 6-9 | (structure) | >280 | 1.34–1.90(7H, m), 2.02–2.18(1H, m), 2.46–2.60(1H, m), 2.75–3.21(4H, m), 7.09(1H, d, J=5Hz), 7.37(1H, d, J=5Hz) | $C_{12}H_{15}NOSCl$ 55.78 (55.91 | 6.26 6.26 | 5.37 5.43) |

REFERENCE EXAMPLE 6-10

3,4-Dihydrospiro[naphthalene-2(1H),2'-piperidin]-1-ol

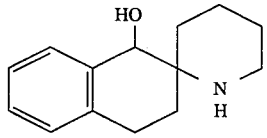

In 20 ml of methanol was dissolved 0.80 g of 3,4-dihydrospiro[naphthalene-2(1H),2'-piperidin]-1-one. Then, 0.15 g of sodium borohydride was added portionwise. The mixture was stirred for 30 minutes, after which it was diluted with water and extracted with methylene chloride. The methylene chloride layer was dried over anhydrous sodium sulfate and filtered and the solvent was then distilled off. The solid residue was recrystallized from methylene chloride-ether to provide 0.25 g of white crystals.

m.p. 125°–127° C.

$^1$H-NMR (ppm, CDCl_3) 1.32–1.98 (8H, m), 2.28 (1H, q, J=7Hz), 2.74–2.94 (4H, m), 4.37 (1H, s), 7.07–7.28 (4H, m), 7.40–7.52 (1H, m)

Elemental analysis for $C_{14}H_{19}NO$

Calcd. C 77.38; H 8.81; N 6.45; Found C 77.16; H 8.84; N 7.01

In the same manner as Reference Example 6-10, the following compounds were synthesized.

REFERENCE EXAMPLE 6-11

3,4-Dihydro-6-methoxyspiro[naphthalene-2(1H),2'-piperidin)-1-ol

REFERENCE EXAMPLE 6-12

3,4-Dihydro-6,7-dimethoxyspiro[naphthalene-2(1H),2'-piperidin)-1-ol hydrochloride

REFERENCE EXAMPLE 6-13

6,7-Dihydrospiro[benzo[b]thiophene-5(4H),2'-piperidin)-4-ol hydrochloride

The structural formulas, physical properties and NMR spectra of the respective compounds are shown in Table 8.

TABLE 8

| Reference Example | Structural Formula | Melting Point (°C.) | NMR (δ_ppm, CDCl₃) | Elemental Analysis [Found/(Calculated)] C H N |
|---|---|---|---|---|
| 6-11 | | 132–134 | 1.33–1.87(9H, m), 2.06–2.22(1H, m), 2.74–2.89(4H, m), 3.78(3H, s), 4.31 (1H, s), 6.64(1H, d, J=3Hz), 6.67(1H, dd, J=9Hz, 3Hz), 7.33(1H, d, J=9Hz) | $C_{15}H_{21}NO_2$ 72.85 8.62 5.66 (72.84 8.56 5.66) |
| 6-12 | | 213–216 (decomposed) | 1.36–1.80(8H, m), 2.03–2.24(2H, m), 2.73(2H, t, J=7Hz), 2.80–2.90(2H, m), 3.84(3H, s), 3.86(3H, s), 4.28(1H, s), 6.59(1H, s), 6.95(1H, s) | $C_{16}H_{24}ClNO_3 \cdot 1/5H_2O$ 60.76 7.69 4.49 (60.54 7.75 4.41) |
| 6-13 | | 215–221 (decomposed) | 1.30–1.90(8H, m), 2.08–2.40(2H, m), 2.75–2.90(4H, m), 4.38(1H, s), 7.00 (1H, d), 7.12(1H, d) | $C_{12}H_{15}NOSCl$ 55.15 6.92 5.34 (55.48 6.98 5.39) |

REFERENCE EXAMPLE 6-14

3,4-Dihydrospiro[naphthalene-2(1H),2'-piperidine]hydrochloride

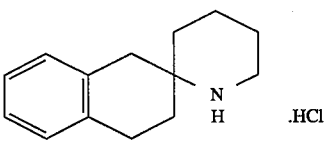

(1) To 200 ml of a methylene chloride solution containing 3.36 g of 3,4-dihydrospiro[naphthalene-2(1H),2'-piperidin]-1-one was added 2.6 g of potassium carbonate. Then, 50 ml of a methylene chloride solution containing 3.4 ml of trifluoroacetic anhydride was added dropwise at 0° C. and the mixture was stirred for 3 hours. The reaction mixture was diluted with water and extracted with methylene chloride. The methylene chloride layer was dried over anhydrous magnesium sulfate and filtered and the solvent was then distilled off. The residue was purified by silica gel column chromatography using ethyl acetate/hexane (1:2) as the eluent and the eluate containing the desired compound was distilled under reduced pressure. The solid residue was recrystallized from ethyl acetate-hexane to provide 4.86 g of 1'-trifluoroacetyl-3,4-dihydrospiro[naphthalene-2(1H),2'-piperidin]-1-one as colorless needles.

m.p. 97–100° C.

¹H-NMR (ppm, CDCl₃) 1.60–2.25 (7H, m), 2.67–3.16 (3H, m), 3.35–3.53 (1H, m), 3.82–3.98 (1H, m), 7.16–7.52 (3H, m), 8.20 (1H, dd, J=8 Hz, 1.2 Hz)

Elemental analysis for $C_{16}H_{16}F_3NO_2$ Calcd. C 61.73; H 5.18; N 4.50; Found C 61.47; H 5.20; N 4.40.

(2) In 30 ml of acetic acid was dissolved 4.44 g of 1'-trifluoroacetyl-3,4-dihydrospiro[naphthalene-2(1H),2'-piperidin]-1-one and using 0.76 g of 10% palladium-on-carbon as the catalyst, catalytic reduction was carried out at 4 kg/cm² and 80° C. The reaction mixture was then poured in water, made basic with 10% aqueous sodium hydroxide solution and extracted with methylene chloride. The methylene chloride layer was dried over anhydrous sodium sulfate and filtered and the solvent was then distilled off. The residue was treated with 3.6 ml of 4N-methanolic HCl to give a solid. This solid was recrystallized from methylene chloride-ether to provide 2.51 g of white crystals.

m.p. 200°–202° C. ¹H-NMR (ppm, CDCl₃) 1.43–1.80 (8H, m), 1.84–2.02 (1H, m), 2.77 (2H, s), 2.84 (4H, t, J=5Hz), 7.10 (4H, s)

Elemental analysis for $C_{14}H_{20}ClN \cdot 1/4H_2O$ Calcd. C 69.40; H 8.53; N 5.78; Found C 69.62; H 8.38; N 5.64

REFERENCE EXAMPLE 6-15

3,4-Dihydro-6-methoxyspiro[naphthalene-2(1H),2'-piperidine]hydrochloride

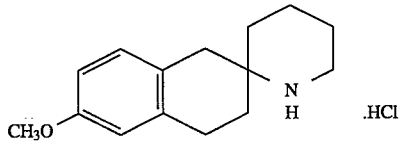

In 30 ml of trifluoroacetic acid was dissolved 6.57 g of 3,4-dihydro-6-methoxyspiro[naphthalene-2(1H),2'-piperidin]-1-one followed by addition of 8.5 ml of triethylsilane and the mixture was stirred for 1 hour. This reaction mixture was poured portionwise in water and after addition of 1N-hydrochloric acid, washed with hexane. The aqueous layer was made basic with 1N-aqueous sodium hydroxide solution and extracted with methylene chloride. The methylene chloride layer was dried over anhydrous sodium sulfate and filtered and the solvent was then distilled off. The residue was treated with 7.0 ml of 4N-methanolic HCl to give a solid. This solid was recrystallized from methanol-ether to provide 5.09 g of white crystals.

m.p. 201°–203° C.

¹H-NMR (ppm, CDCl₃) 1.31–2.00 (9H, m), 2.71 (2H, s), 2.74–2.88 (4H, m), 3.77 (3H, m), 6.62–6.73 (2H, m), 6.98 (1H, m)

Elemental analysis for C$_{15}$H$_{22}$ClNO.⅓H$_2$O Calcd. C 66.38; H 8.32; N 5.16; Found C 66.65; H 8.46; N 5.03

In the same manner as Reference Example 6-15, the following compounds were synthesized.

REFERENCE EXAMPLE 6-16

3,4-Dihydro-6,7-dimethoxyspiro[naphthalene-2(1H), 2'-piperidine] hydrochloride

REFERENCE EXAMPLE 6-17

3,4-Dihydro-8-methoxyspiro[naphthalene-2(1H),2'-piperidine]hydrochloride

REFERENCE EXAMPLE 6-18

6,7-Dihydrospiro[benzo[b]thiophene-5(4H),2'-piperidine]hydrochloride

The structural formulas, physical properties and NMR spectra of the respective compounds are shown in Table 9.

was added lithium aluminum hydride (0.44 g) portionwise with ice-cooling and stirring. After completion of dropwise addition, the mixture was heated and stirred at 60° C. for 3 hours. The reaction mixture was then cooled with ice again, and water (1 ml), 15% aqueous sodium hydroxide solution (3 ml) and water (1 ml) were added in the order mentioned. The resulting precipitate was filtered off and the filtrate was extracted using ethyl acetate and saturated aqueous sodium hydrogen carbonate solution. The organic layer was separated, washed with water, dried over anhydrous sodium sulfate, and concentrated to dryness. The residue was washed with ethyl acetate to provide the title compound (0.82 g) as colorless powder.

Reference Example Compounds 7-2~4 were synthesized from reference compound 2-2, 2-4 and 2-5 respectively in the same manner as Reference Example 7-1.

Compound 7-2
5-Amino-4,4-diphenylpentanol

Compound 7-3
5-Amino-4-(p-chlorophenyl)-4-phenylpentanol

TABLE 9

| Reference Example | Structural Formula | Melting Point (°C.) | NMR (δ$_{ppm}$, CDCl$_3$) | Elemental Analysis [Found/(Calculated)] C H N |
|---|---|---|---|---|
| 6-16 | (CH$_3$O, CH$_3$O substituted structure).HCl | 205–208 | 1.39–2.00(9H, m), 2.63–2.88(6H, m), 3.83 (6H, s), 6.55(1H, s), 6.59(1H, s) | C$_{16}$H$_{24}$ClNO$_2$  64.20  8.13  4.66 (64.53  8.12  4.70) |
| 6-17 | (CH$_3$O substituted structure).HCl | 239–241 | 1.40–1.74(8H, m), 1.81–1.98(1H, m), 2.53–2.96(6H, m), 3.81(3H, s), 6.66(1H, d, J=8Hz), 6.73(1H, d, J=8Hz), 7.09(1H, d, J=8Hz) | C$_{15}$H$_{22}$ClNO  67.28  8.15  5.16 (67.28  8.28  5.23) |
| 6-18 | (thiophene fused structure).HCl | 212–220 | 1.40–1.85(8H, m), 1.92–2.05(1H, m), 2.52–2.90(6H, m), 6.72(1H, d), 7.08(1H, d) | C$_{12}$H$_{18}$NSCl  58.96  7.09  5.38 (59.12  7.44  5.75) |

REFERENCE EXAMPLE 7-1

4-Amino-3,3-diphenylbutanol

To a solution of ethyl 3-cyano-3,3-diphenylpropionate (reference compound 2-1) (1.2 g) in tetrahydrofuran (30 ml)

Compound 7-4
5-Amino-4,4-bis(p-chlorophenyl)pentanol

The structural formulas, physical properties and NMR spectra of the respective compounds are shown in Table 10.

TABLE 10

| Reference Example | R⁰ | Ar | m | Melting Point (°C.) | $^1$H—NMR ($\delta_{ppm}$, CDCl$_3$) |
|---|---|---|---|---|---|
| 7-1 | H | phenyl | 2 | 131–133 | 2.32(2H, t), 3.15(2H, t), 3.23(2H, s), 7.10–7.33(10H, m) |
| 7-2 | H | phenyl | 3 | Syrup | |
| 7-3 | H | 4-Cl-phenyl | 3 | Syrup | 1.17–1.33(2H, m), 1.55(2H, br), 2.14–2.24(2H, m), 3.31(2H, s), 3.56(2H, t), 7.07–7.38(9H, m) |
| 7-4 | p-Cl | 4-Cl-phenyl | 3 | Syrup | 1.10–1.30(2H, m), 1.55(2H, br), 2.14–2.24(2H, m), 3.29(2H, s), 3.55(2H, t), 7.00–7.30(8H, m) |

REFERENCE EXAMPLE 8-1

4-Formylamino-3,3-diphenylbutanol

In formic acid (100 ml) was dissolved 4-amino-3,3-diphenylbutanol (reference compound 7-1) (17.1 g) followed by addition of acetic anhydride (16 ml) and the mixture was stirred at room temperature for 7 hours. The reaction mixture was concentrated to dryness and the residue was distributed between chloroform and water. The aqueous layer was made basic with aqueous ammonia and extracted with chloroform. The extract was dried over anhydrous sodium sulfate and concentrated to dryness. The residue was dissolved in ethanol (50 ml) and the solution was stirred with 1N-sodium hydroxide solution (60 ml) at room temperature for 15 minutes. To this reaction mixture was added water and the resulting crystals were recovered by filtration. The crystals were washed serially with water and ethyl acetate to provide the title compound (16 g) as colorless powder.

The following Reference Example Compounds 8-2~4 were synthesized in the same manner as Reference Example 8-1.

Compound 8-2
5-Formylamino-4,4-diphenylpentanol

Compound 8-3
4-(p-Chlorophenyl)-5-formylamino-4-phenylpentanol

Compound 8-4
4,4-Bis(p-chlorophenyl)-5-formylaminopentanol

The structural formulas, physical properties and NMR spectra of the respective compounds are shown in Table 11.

TABLE 11

| Reference Example | R⁰ | Ar | m | Melting Point (°C.) | $^1$H—NMR ($\delta_{ppm}$, CDCl$_3$) |
|---|---|---|---|---|---|
| 8-1 | H | phenyl | 2 | 133–135 | 2.28(2H, t), 3.17(2H, q), 3.90(2H, d), 4.37(1H, t), 7.11–7.34 (10H, m), 7.48(1H, br t), 7.88(1H, d) |

TABLE 11-continued

| Reference Example | R⁰ | Ar | m | Melting Point (°C.) | ¹H—NMR (δ_ppm, CDCl₃) |
|---|---|---|---|---|---|
| 8-2 | H | (phenyl) | 3 | 151–152 | 1.32(2H, m), 2.16(2H, m), 3.55(2H, t), 4.05(2H, d), 5.10–5.30 7.10–7.40(10H, m), 8.08(1H, d). |
| 8-3 | H | (p-Cl-phenyl) | 3 | 159–161 | 1.00–1.23(2H, m), 2.03(2H, t), 3.30(2H, q), 3.88(2H, dd), 4.33 (1H, t), 7.10–7.37(9H, m), 7.48(1H, br t), 7.87(1H, d) |
| 8-4 | p-Cl | (p-Cl-phenyl) | 3 | 175–178 | 1.00–1.20(2H, m), 2.04(2H, t), 3.30(2H, q), 3.86(2H, d), 4.34 (1H, t), 7.10–7.40(8H, m), 7.55(1H, br t), 7.88(1H, d) |

REFERENCE EXAMPLE 9-1

4-Formylamino-3,3-diphenylbutyl tosylate

To a suspension of 4-formylamino-3,3-diphenylbutanol (21.5 g) in methylene chloride (250 ml) were added triethylamine (22 ml), 4-dimethylaminopyridine (catalyst amount) and tosyl chloride (15.3 g) and the mixture was stirred at room temperature for 16 hours. The reaction mixture was concentrated to dryness and dissolved in water-ethyl acetate. The ethyl acetate layer was washed with 1N-hydrochloric acid, further washed with water, dried over anhydrous sodium sulfate, and concentrated to dryness. The residue was purified by silica gel column chromatography (n-hexane: ethyl acetate 4:1~1:1) to provide the title compound (32 g) as colorless syrup.

Reference Example compound 9-4 was synthesized in the same manner as Reference Example 9-1.

Compound 9-4

4,4-Bis(p-chlorophenyl)-5-(formylamino)pentyl tosylate

REFERENCE EXAMPLE 9-2

5-Formylamino-1-iodo-4,4-diphenylpentane

To a solution of 5-formylamino-4,4-diphenylpentanol (38.3 g) in methylene chloride (600 ml) were added p-toluenesulfonyl chloride (29.2 g), triethylamine (15 g) and a catalyst amount of 4,4-dimethylaminopyridine and the mixture was stirred at room temperature for 4 hours. The reaction mixture was then concentrated to dryness and sodium iodide (46.6 g) and acetone (600 ml) were added to the residue. The mixture was heated and stirred at 50° C. for 2 hours, after which it was concentrated to dryness. The residue was extracted with ethyl acetate and water. The organic layer was separated and washed with aqueous sodium thiosulfate solution. It was dried over anhydrous sodium sulfate and concentrated to dryness and the residue was purified by silica gel column chromatography to provide the title compound (46.5 g) as yellow syrup.

Reference Example Compound 9-3 was synthesized in the same manner as Reference Example 9-2.

Compound 9-3

4-(p-Chlorophenyl)-5-formylamino-1-iodo-4-phenylpentane

The structural formulas, physical properties and NMR spectra of the respective compounds are shown in Table 12.

TABLE 12

| Reference Example | R° | Ar | L | m | Melting Point (°C.) | $^1$H—NMR ($\delta_{ppm}$, CDCl$_3$) |
|---|---|---|---|---|---|---|
| 9-1 | H | 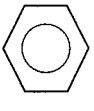 | OTs | 2 | Syrup | 2.45(3H, s), 2.52(2H, t), 3.87(2H, t), 3.96(2H, d), 5.00–5.20 (1H, br), 7.00–7.40(12H, m), 7.67(2H, d), 8.08(1H, d). |
| 9-2 | H | 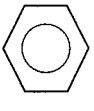 | I | 3 | Syrup | 1.49–1.65(2H, m), 2.12–2.25(2H, m), 3.10(2H, t), 4.04(2H, d), 5.07(1H, br t), 7.11–7.40(10H, m), 8.11(1H, d) |
| 9-3 | H | 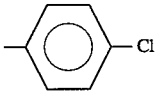 | I | 3 | Syrup | 1.46–1.63(2H, m), 2.10–2.22(2H, m), 3.10(2H, t), 4.01(2H, d), 5.08(1H, br t), 7.06–7.39(9H, m), 8.10(1H, d) |
| 9-4 | p-Cl | 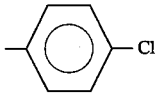 | OTs | 3 | Syrup | 2.45(3H, s), 3.90–4.00(4H, m), 5.00–5.20(1H, Br, 7.00–7.40 (10H, m), 7.72(2H, m), 8.08(1H, d). |

REFERENCE EXAMPLE 10-1

1-[4-(p-Fluorophenyl)piperazin-1-yl]-4-formylamino-3,3-diphenylbutane dihydrochloride A mixture of 4-formylamino-3,3-diphenylbutyl tosylate (7 g) and 1-(p-fluorophenyl)piperazine (5.2 g) was heated in acetonitrile (50 ml) at 60° C. with stirring for 4 hours. The reaction mixture was then concentrated to dryness and dissolved in water-ethyl acetate. The ethyl acetate layer was washed with water, dried over anhydrous sodium sulfate and concentrated to dryness. The residue was purified by silica gel column chromatography (ethyl acetate) and treated with hydrochloric acid to provide the title compound (7 g) as white crystals.

Reference Example Compounds 10-2, 10-4~8 and 10-10~12 were respectively synthesized in the same manner as Reference Example 10-1.

Compound 10-2
5-Formylamino-1-morpholino-4,4-diphenylpentane hydrochloride

Compound 10-4
5-Formylamino-1-[2,3,4,5-tetrahydro-1(H)-3-benzazepin-3-yl]-4,4-diphenylpentane hydrochloride Compound 10-5
5-Formylamino-1-dimethylamino-4,4-diphenylpentane Compound 10-6
1-(N-Benzyl-N-methylamino)-5-formylamino-4,4-diphenylpentane hydrochloride Compound 10-7
5-Formylamino-4,4-diphenyl-1-(4-phenylpiperazin-1yl) pentane Compound 10-8
1-[4-(p-Fluorophenyl)piperazin-1-yl]-5-formylamino-4,4-diphenylpentane dihydrochloride Compound 10-10
4-(p-Chlorophenyl)-5-formylamino-4-phenyl-1-(4 -phenylpiperazin-1-yl)pentane dihydrochloride Compound 10-11
4-(p-Chlorophenyl)-5-formylamino-4-phenyl-1-(4phenylpiperidino)pentane hydrochloride Compound 10-12
4,4-Bis(p-chlorophenyl)-1-[4-(p-fluorophenyl)-piperazin-1-yl]-5-(formylamino)pentane dihydrochloride

REFERENCE EXAMPLE 10-3

N-(5-Formylamino-4,4-diphenylpentyl)phthalimide

A mixture of 5-formylamino-1-iodo-4,4-diphenylpentane (7 g) and potassium phthalimide (3.63 g) was stirred in DMF (40 ml) at room temperature for 3 hours. The reaction mixture was poured in ice-water and the syrup which separated out was extracted with ethyl acetate. The extract was washed with water, dried over anhydrous sodium sulfate and concentrated to dryness. The residue was washed with isopropyl ether to provide the title compound (5.2 g) as colorless powder.

Reference Example Compound 10-9 was synthesized in the same manner as Reference Example 10-3.

Compound 10-9
N-[4-(p-Chlorophenyl)-5-formylamino-4-phenylpentyl]phthalimide

The structural formulas, physical properties and NMR spectra of the above compounds are shown in Tables 13 and 14.

TABLE 13

![structure: Ar-C(CH2)m-R' with NCHO/H branch, ·xHCl, R0 on Ar phenyl]

| Reference Example | R' | R⁰ | Ar | m | x | Melting Point (°C.) | NMR (δ_ppm, CDCl₃) |
|---|---|---|---|---|---|---|---|
| 10-1 | 4-(4-fluorophenyl)piperazin-1-yl | H | phenyl | 2 | 2 | 145–148 | 2.10–2.40(4H, m), 2.52(4H, t), 3.08(4H, t), 4.05(2H, d), 5.60–5.80(1H, br s), 6.80–7.00(4H, m), 7.10–7.40(10H, m), 8.12(1H, d). |
| 10-2 | morpholin-4-yl | H | phenyl | 3 | 1 | Noncrystalline powder | 1.26(2H, m), 2.00–2.30(6H, m), 3.64(4H, t), 4.04(2H, d), 5.00–5.20(1H, br), 7.10–7.40(9H, m), 8.09(1H, d). |
| 10-3 | phthalimido | H | phenyl | 3 | — | 171–172 | 1.40–1.58(2H, m), 2.05–2.20(2H, m), 3.61(2H, t), 4.00(2H, d), 5.00(1H, br t), 7.05–7.32(10H, m), 7.64–7.76(2H, m), 7.75–7.85(2H, m), 8.02(1H, d) |
| 10-4 | 2,3,4,5-tetrahydro-1H-2-benzazepin-2-yl | H | phenyl | 3 | 1 | 123–126 | 1.29(2H, m), 2.09(2H, m), 2.38(4H, t), 2.49(4H, m) 2.84(4H, m), 4.05 (2H, d), 5.10(1H, br s), 7.00–7.40 (14H, m), 8.09(1H, d). |
| 10-5 | —N(CH₃)₂ | H | phenyl | 3 | — | 98–99 | 1.12–1.31(2H, m), 2.04–2.22(4H, m), 2.09(6H, s), 4.05 (2H, d), 5.16(1H, br s), 7.13–7.37(10H, m), 8.09(1H, d) |
| 10-6 | —N(CH₂Ph)(CH₃) | H | phenyl | 3 | 1 | 97–105 | 1.20–1.36(2H, m), 2.04(3H, s), 2.02–2.15(2H, m), 2.28(2H, t), 3.36(2H, s), 4.04(2H, d), 5.11(1H, br t), 7.10–7.37(15H, m), 8.06(1H, d) |

TABLE 13-continued
| Reference Example | R' | R⁰ | Ar | m | x | Melting Point (°C.) | NMR (δ_ppm, CDCl₃) |
|---|---|---|---|---|---|---|---|
| 10-7 | 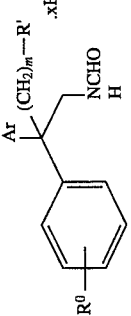 | H |  | 3 | — | Syrup | 1.20–1.39(2H, m), 2.04–2.20(2H, m), 2.30(2H, t), 2.45 (4H, t), 3.13(4H, t), 4.06(2H, d), 5.09(1H, br t), 6.79–6.92(3H, m), 7.12–7.37(12H, m), 8.09(1H, d) |
| 10-8 |  | H |  | 3 | 2 | Noncrystal-line powder | 1.20–1.40(2H, m), 2.10–2.40(4H, m), 2.45(4H, t), 3.05 (4H, t), 4.06(2H, d), 5.10(1H, br s), 6.80–7.00(4H, m), 7.10–7.40(10H, m), 8.10(1H, d). |

TABLE 14

| Reference Example | R' | R° | Ar | m | x | Melting Point (°C.) | NMR ($\delta_{ppm}$, CDCl$_3$) |
|---|---|---|---|---|---|---|---|
| 10-9 | phthalimide group (N-linked) | H | 4-Cl-phenyl | 3 | — | Noncrystalline powder | 1.37–1.60(2H, m), 2.03–2.19(2H, m), 3.61(2H, t), 3.97 (2H, q), 5.00(1H, br s), 6.99–7.33(9H, m), 7.65–7.83 (4H, m), 8.02(1H, s) |
| 10-10 | 4-phenylpiperazin-1-yl | H | 4-Cl-phenyl | 3 | 2 | 133–138 | 1.20–1.36(2H, m), 2.03–2.15(2H, m), 2.31(2H, t), 2.46 (4H, t), 3.14(4H, t), 4.03(2H, d), 5.10(1H, br t), 6.80–6.93(3H, m), 7.06–7.38(11H, m), 8.10(1H, d) |
| 10-11 | 4-phenylpiperidin-1-yl | H | 4-Cl-phenyl | 3 | 1 | 118–123 | 1.20–1.39(2H, m), 1.40–2.19(8H, m), 2.29(2H, t), 2.32–2.53(1H, m), 2.89(2H, d), 4.03(2H, dd), 5.21 (1H, br t), 7.06–7.37(14H, m), 8.19(1H, d) |
| 10-12 | 4-(4-fluorophenyl)piperazin-1-yl | p-Cl | 4-Cl-phenyl | 3 | 2 | Noncrystalline powder | 1.20–1.40(2H, m), 2.10–2.40(4H, m), 2.46(4H, m), 3.06 (4H, t), 4.00(2H, d), 5.10(1H, br s), 6.80–7.30(12H, m) 8.10(1H, d). |

REFERENCE EXAMPLE 11-1

4-Bromo-3,4-dihydro-5-oxo-1-[2,4,6-(triisopropyl) benzenesulfonyl]-5H-benz[cd]indole To a solution of 3,4-dihydro-5-oxo-1-[2,4,6-(triisopropyl) benzenesulfonyl]-5H-benz[cd]indole (11 g; 75% purity) in THF (80 ml) was slowly added phenyltrimethylammonium tribromide [7.15 g in THF (25 ml)] at −45° C. The mixture was stirred from −45° C. to room temperature for one hour and filtrated off. The solution was concentrated and the residue was washed with ether to give the titled compound as pale a yellow powder (8.9 g).

Reference Example Compound 11-2 was synthesized as a same manner with Reference Example 11-1.

Compound 11-2

4-Bromo-3,4-dihydro-6-methoxy-5-oxo-1-(p-toluenesulfonyl)-5H-benz[cd]indole

REFERENCE EXAMPLE 11-3

4-Azido-3,4-dihydro-5-oxo-1-[2,4,6-(triisopropyl) benzenesulfonyl]-5H-benz[cd]indole To a solution of 4-bromo-3,4-dihydro-5-oxo-1-[2,4,6-(triisopropyl)benzenesulfonyl]-5H-benz[cd]indole [11.9 g in DMF (200 ml)] was added acetic acid (3.3 ml) followed by aqueous sodium azide [3.3 g in water (22 ml)] at −25° C. The mixture was warmed to −10° C. and stirred at −10° C. for 30 min and poured into the ice-water. The precipitate was filtrated, washed with water, and dried to give the titled compound as a yellow powder (10.3 g).

Reference Example compound 11-4 was synthesized as same manner with Reference Example 11-3.

Compound 11-4
4-Azido-3,4-dihydro-6-methoxy-5-oxo-1-(p-toluenesulfonyl)-5H-benz[cd]indole

REFERENCE EXAMPLE 11-5

4-Acetylamino-3,4-dihydro-5-oxo-1-[2,4,6-(triisopropyl)benzenesulfonyl]-5H-benz[cd]indole The mixture of 4-Azido-3,4-dihydro-5-oxo-1-[2,4,6-(triisopropyl)benzenesulfonyl]-5H-benz[cd]indole (10.3 g) and acetic anhydride (4.4 g) in THF (150 ml) was hydrogenated over 10% Pd-carbon (3 g) at room temperature for four hours. The catalyst was filtered and the filtrate was concentrated. The residue was recrystalized from hexane/isopropyl ether to give the titled compound as a pale yellow powder (9.3 g).

Reference Example Compound 11-6 was synthesized as same manner with Reference example 11-5.

Compound 11-6

4-Acetylamino-3,4-dihydro-6-methoxy-5-oxo-1-(p-toluenesulfonyl)-5H-benz[cd]indole

REFERENCE EXAMPLE 11-7

1-[2,4,6-(Triisopropyl)benzenesulfonyl]spiro{benz[cd]indole-4(3H,5H),2'-(1'-acetylpiperidine}-5-one Sodium hydride (0.6g, 60% purity) was washed with hexane and suspended in DMF (20 ml). 1,4-Dibromobutane was added followed by 4-acetylamino-3,4-dihydro-5-oxo-1-[2,4,6-(triisopropyl)benzenesulfonyl]-5H-benz[cd]indole [3.1 g in DMSO (10 ml)] at −13° C. under the nitrogen stream. The mixture was stirred at −13° C. for 5 minutes and at 0° C. for 20 min. and then poured into the mixture of ice and 1N hydrogen chloride. The separated oil was extracted with ethyl acetate and the organic layer was washed with water, concentrated. The residue was purified by silica gel chromatography and recrystalized from hexane/isopropyl ether to give the titled compound as a yellow powder (2.3 g).

Reference Example Compound 11-8 was synthesized as same manner with Reference Example 11-7.

Compound 11-8
6-Methoxy-1-[p-toluenesulfonyl]spiro{benz[cd]indole-4(3H,5H), 2'-(1'-acetylpiperidine)}-5-one

REFERENCE EXAMPLE 11-9

1-[2,4,6(Triisopropyl)benzenesulfonyl]spiro{benz[cd]indole-4(3H,5H), 2'-piperidine}-5-one The mixture of 1-[2,4,6-(triisopropyl)benzenesulfonyl] spiro{benz[cd]indole-4(3H,5H), 2'-(1'-acetylpiperidine}-5-one (1.9 g), conc. hydrogen chloride (8 ml), and ethanol (30 ml) was refluxed for 39 hours. The mixture was concentrated and treated with ethyl acetate and saturated aqueous sodium hydrogen sulfate. The organic phase was separated, washed with water, and concentrated. The residue was purified by silica gel chromatography and recrystalized from hexane to give the titled compound as a pale yellow powder (1.4 g).

Reference Example compound 11-10 was synthesized as same manner with Reference Example 11-9.

Compound 11-10
6-Methoxy-1-[p-toluenesulfonyl]spiro{benz[cd]indole-4(3H,5H), 2'-piperidine}-5-one

REFERENCE EXAMPLE 11-11

Spiro{1H-benz[cd]indole-4(3H,5H), 2'-piperidine}-5-one

1-[2,4,6-(Triisopropyl)benzenesulfonyl]spiro{benz[cd] indole-4(3H,5H), 2'-piperidine}-5-one (3.3 g) was refluxed with 1N-aqueous sodium hydroxide (25 ml) and methanol (120 ml) for 24 hours. The mixture was concentrated and the residue was washed with water to give the titled compound as a yellow powder (1.5 g).

Reference Example compound 11-12 was synthesized as same manner with Reference Example 11-9.

Compound 11-12
6-Methoxyspiro{1H-benz[cd]indole-4(3H,5H),2'-piperidine}-5-one

REFERENCE EXAMPLE 11-13

5-Hydroxyl-6-methoxy-1-(p-toluenesulfonyl)spiro{benz[cd]indole-4(3H,5H),2'-piperidine}

To a solution of 6-methoxy-1-[p-toluenesulfonyl] spiro{benz[cd]indole-4(3H,5H),2'-piperidine}-5-one (0.73 g) in THF (15 ml) was added lithium aluminum hydride (0.14 g) as a portion wise manner at 0° C. The mixture was refluxed for 24 hours. The mixture was cooled and treated with water. The precipitate was filtered off and the filtrate was extracted with ethyl acetate. The extract was washed with water and concentrated. The residue was purified by silica gel chromatography and recrystalized from isopropyl ether/ethyl acetate to give the titled compound (0.59 g) as a pale yellow powder.

REFERENCE EXAMPLE 11-14

6-Methoxy-1-(p-toluenesulfonyl)spiro{benz[cd]indole-4(3H,5H),2'-piperidine}

To a solution of 5-hydroxyl-6-methoxy-1-(p-toluenesulfonyl)spiro{benz[cd]indole-4(3H,5H),2'-piperidine}in trifluoroacetic acid (20 ml) was added triethylsilane (6.5 ml) and the mixture was stirred at room temperature for 20 hours. The mixture was concentrated and the residue was treated with ethyl acetate and water. The aqueous phase was basified with aqueous ammonia and extracted with ethyl acetate. The combined extract was washed with water and concentrated. The residue was purified by silica gel chromatography to give the titled compound (0.55 g) as a pale brown powder.

REFERENCE EXAMPLE 11-15

6-Methoxyspiro{1H-benz[cd]indole-4(3H,5H),2'-piperidine}

The mixture of 6-methoxy-1-(p-toluenesulfonyl)spiro{benz[cd]indole-4(3H,5H),2'-piperidine}(0.55 g), methanol (15 ml), and 1N-aqueous sodium hydroxide (3 ml) was refluxed for 90 min. The mixture was concentrated and the residue was treated with ethyl acetate and water. The organic phase was washed with water and concentrated. The residue was purified by silica gel chromatography and recrystalized from acetone/isopropyl ether to give the titled compound (0.19 g) as a white powder.

The structural formulas, yield and NMR spectra of the above compounds are shown in Tables 15, 16 and 17.

TABLE 15

| Reference Example | Structural Formula | Yield(%) | NMR ($\delta_{ppm}$, CDCl$_3$) |
|---|---|---|---|
| 11-1 | | 92 | 1.09, 1.12, 1.25(each 6H, d), 2.82–3.03(1H, m), 3.57(1H, dd), 3.84(1H, ddd), 4.07–4.28(2H, m), 4.83, (1H, dd), 7.20(2H, s), 7.39(1H, s), 7.39(1H, t), 7.71, 7.79(each, 1H, d) |
| 11-2 | | 100 | 2.36, 3.97(each, 3H, s), 3.46(1H, dd), 4.72(1H, dd), 7.01, 8.09(each, 1H, d), 7.25, 7.75(each 2H, d), 7.45(1H, d) |
| 11-3 | | 94 | 1.10(12H, d), 1.25(6H, d), 2.82–3.03(1H, m), 3.15(1H, ddd), 3.48(1H, dd), 4.07–4.26(2H, m), 4.47(1H, dd), 7.20(2H, s), 7.30(1H, s), 7.39(1H, t), 7.73, 7.76(each 1H, d) |

TABLE 15-continued

| Reference Example | Structural Formula | Yield(%) | NMR ($\delta_{ppm}$, CDCl$_3$) |
|---|---|---|---|
| 11-4 | | 100 | 2.37, 3.98(each 3H, s), 3.01(1H, ddd), 3.33(1H, dd), 4.35 (1H, dd), 7.00, 8.08(each 1H, d), 7.25, 7.74(each 2H, d), 7.37 (1H, s) |
| 11-5 | | 88 | 1.08, 1.13, 1.26(each 6H, d), 2.12(3H, s), 2.82–3.03(1H, m), 2.82(1H, dd), 3.96(1H, dd), 4.07–4.28(2H, m), 4.79–4.92 (1H, m), 6.72(1H, br d), 7.21(2H, s), 7.23(1H, d), 7.38 (1H, t), 7.70, 7.78(each 1H, d) |
| 11-6 | | 79 | 2.09, 2.37, 3.96(each 3H, s), 2.74(1H, ddd), 3.85(1H, dd), 4.72(1H, ddd), 6.78(1H, br d), 6.97, 8.07(each 1H, d), 7.25, 7.74(each 2H, d), 7.33(1H, d) |

TABLE 16

| Reference Example | Structural Formula | Yield(%) | NMR ($\delta_{ppm}$, CDCl$_3$) |
|---|---|---|---|
| 11-7 | | 67 | 1.08, 1.11, 1.25(each 6H, d), 1.52–1.90(6H, m), 2.14(3H, s), 2.81–3.02(1H, m), 3.20–3.58(3H, m), 3.75–3.89(1H, m), 4.08–4.29(2H, m), 7.18(2H, s), 7.23(1H, d), 7.33(1H, t), 7.60, 7.81(each 1H, d) |

TABLE 16-continued

| Reference Example | Structural Formula | Yield(%) | NMR ($\delta_{ppm}$, CDCl$_3$) |
|---|---|---|---|
| 11-8 | | 74 | 1.54–1.84(6H, m), 2.09, 2.37, 3.94(each 3H, s), 3.13(1H, d), 3.31–3.58(2H, m), 3.65–3.80(1H, m), 6.96, 8.01(each 1H, d), 7.23. 7.71(each 2H, d), 7.26(1H, s) |
| 11-9 | | 100 | 1.08, 1.11, 1.25(each 6H, d), 1.40–1.90(6H, m), 2.80–3.11 (4H, m), 3.53 (1H, d), 4.09–4.29(2H, m), 7.19(2H, s), 7.28 (1H, d), 7.36(1H, t), 7.66, 7.70(each 1H, d) |
| 11-10 | | 93 | 1.35–1.83(6H, m), 2.36, 3.96(each 3H, s), 2.73–2.90(1H, m), 2.91, 3.35(each 1H, d), 2.91–3.30(1H, m), 6.98, 8.01(each 1H, d), 7.24, 7.74(each 2H, d), 7.34(1H, s) |
| 11-11 | | 95 | 1.29–1.57(4H, m), 1.55–1.70(2H, m), 1.69–1.88(2H, m), 2.93, 3.44(each 1H, d), 7.23(1H, t), 7.29(1H, s), 7.38, 7.58 (each 1H, d), 11.06(1H, br s) |
| 11-12 | | 94 | 1.23–1.65(6H, m), 2.60–2.77(1H, m), 2.84, 3.30(each 1H, d), 2.79–2.91(1H, m), 3.82(3H, s), 6.90, 7.51(each 1H, d), 7.24 (1H, s) |

TABLE 16-continued

| Reference Example | Structural Formula | Yield(%) | NMR ($\delta_{ppm}$, CDCl$_3$) |
|---|---|---|---|
| 11-13 | (structure: MeO, OH substituted isochroman-piperidine spiro with Me-C$_6$H$_4$-SO$_2$-N=CH-NH) | 80 | 1.38–1.95(6H, m), 2.34, 3.82(each 3H, s), 2.63(2H, t), 2.73, 2.92(each 1H, d), 4.96(1H, s), 6.90, 7.77(each 1H, d), 7.20, 7.73(each 2H, d), 7.22(1H, s) |

TABLE 17

| Reference Example | Structural Formula | Yield(%) | NMR ($\delta_{ppm}$, CDCl$_3$) |
|---|---|---|---|
| 11-14 | (structure: OMe substituted, Me-C$_6$H$_4$-SO$_2$-N=CH-NH) | 82 | 1.42–1.73(6H, m), 2.33, 3.83(each 3H, s), 2.61(2H, d), 2.65–2.74(2H, m), 2.84, 3.13(each 1H, d), 6.88, 7.65(each 1H, d), 7.18, 7.72(each 2H, d), 7.17(1H, s) |
| 11-15 | (structure: OMe substituted, HN=) | 53 | 1.30–1.58(6H, m), 2.60–2.83(6H, m), 3.75(3H, s), 6.78, 7.04 (each 1H, d), 6.94(1H, s) |

EXAMPLE I-1

4-Phenyl-4-[2-(1-imidazolyl)ethyl]isochroman hydrochloride

A mixture of synthesized 4-(2-iodoethyl)-4-phenylisochroman (0.6 g) and imidazole (0.56 g) was heated in acetonitrile (15 ml) in the presence of potassium carbonate (0.34 g) at 60° C. with stirring for 4 days. The reaction mixture was then poured in ice-water and the syrup separating out was extracted with ether. The extract was washed with water, dried over anhydrous sodium sulfate and concentrated to dryness. The residue was purified by silica gel column chromatography (ethyl acetate-methanol=15:1) and treated with 4NHCl/methanol to provide the title compound (0.32 g) as non-crystalline powder.

EXAMPLE I-3

4-Phenyl-4-[2-(phthalimido)ethyl]isochroman

A mixture of synthesized 4-(2-iodoethyl)-4-phenylisochroman (0.5 g) and potassium phthalimide (0.51 g) was heated in DMF (10 ml) at 60° C. with stirring for 14 hours. The reaction mixture was then poured in ice-water and the syrup separating out was extracted with ethyl acetate. The extract was washed with water, dried over anhydrous sodium sulfate and concentrated to dryness. The residue was purified by silica gel column chromatography and recrystallized from ethyl acetate-hexane to provide the title compound (0.12 g) as colorless needless.

The following compounds I-2 and I-4~70 were synthesized in the same manner as Example I-1 and I-3. Compounds of Examples I-1 through I-70

EXAMPLE I-2

4-[2-(Morpholino)ethyl]-4-phenylisochroman hydrochloride

EXAMPLE I-4

4-[2-(Benzylamino)ethyl]-4-phenylisochroman hydrochloride

EXAMPLE I-5

4-[2-(m-Methoxybenzylamino)ethyl]-4-phenylisochroman hydrochloride

EXAMPLE I-6

4-[2-(4-Phenylpiperazin-1-yl)ethyl]-4-phenylisochroman dihydrochloride

EXAMPLE I-7

4-{2-[4-(p-Fluorophenyl)piperazin-1-yl]ethyl}-4phenylisochroman hydrochloride

EXAMPLE I-8

4-{2-[4-(m-Chlorophenyl)piperazin-1-yl]ethyl}-4phenylisochroman hydrochloride

EXAMPLE I-9

4-{2-[4-(2-Pyridyl)piperazin-1-yl]ethyl}-4-phenylisochroman dihydrochloride

EXAMPLE I-10

4-[2-(4-Benzylpiperazin-1-yl)ethyl]-4-phenylisochroman dihydrochloride

EXAMPLE I-11

4-[2-(4-Phenylpiperidino)ethyl]-4-phenylisochroman hydrochloride

EXAMPLE I-12

3,4-Dihydro-1'-[2-(4-phenylisochroman-4-yl)ethyl]spiro[naphthalene-2(1H),2'-piperidine] hydrochloride

EXAMPLE I-13

3,4-Dihydro-6,7-dimethoxy-1'-[2-(4-phenylisochroman-4-yl)ethyl]spiro[naphthalene-2(1H),2'-piperidine]hydrochloride

EXAMPLE I-14

4-[3-(1-Imidazolyl)propyl]-4-phenylisochroman hydrochloride

EXAMPLE I-15

4-[3-(1-Hexamethyleneimino)propyl]-4-phenylisochroman hydrochloride

EXAMPLE I-16

4-[3-(1,2,4,5-Tetrahydro-3H-benzazepin-3-yl)propyl]-4-phenylisochroman hydrochloride

EXAMPLE I-17

4-(3-Anilinopropyl)-4-phenylisochroman hydrochloride

EXAMPLE I-18

4-[3-(Benzylamino)propyl]-4-phenylisochroman hydrochloride

EXAMPLE I-19

4-[3-(o-Fluorobenzylamino)propyl]-4phenylisochroman hydrochloride

EXAMPLE I-20

4-[3-(o-Chlorobenzylamino)propyl]-4phenylisochroman hydrochloride

EXAMPLE I-21

4-[3-(N-Methylbenzylamino)propyl]-4phenylisochroman hydrochloride

EXAMPLE I-22

4-{3-[(2-Thienylmethyl)amino]propyl}-4-phenylisochroman hydrochloride

EXAMPLE I-23

4-[3-(2-picolylamino)propyl]-4-phenylisochroman dihydrochloride

EXAMPLE I-24

4-[3-(β-Phenethylamino)propyl]-4-phenylisochroman hydrochloride

EXAMPLE I-25

4-[3-(3,4-Dimethoxyphenethylamino)propyl]-4phenylisochroman hydrochloride

EXAMPLE I-26

4-{3-[2-(2-Pyridyl)ethylamino]propyl}-4-phenylisochroman dihydrochloride

EXAMPLE I-27

4-{3-[2-(Morpholino)ethylamino]propyl}-4-phenyl-isochroman dihydrochloride

EXAMPLE I-28

4-[3-(2-Indanylamino)propyl]-4-phenylisochroman hydrochloride

EXAMPLE I-29

4-[3-(4-Phenylpiperazin-1-yl)propyl]-4-phenylisochroman dihydrochloride

EXAMPLE I-30

4-{3-[4-(p-Fluorophenyl)piperazin-1-yl]propyl}-4phenylisochroman dihydrochloride

EXAMPLE I-31

4-{3-[4-(2-Benzothiazolyl)piperazin-1-yl]propyl}-4-phenylisochroman dihydrochloride

EXAMPLE I-32

4-{3-[4-(3-Benzoisothiazolyl)piperazin-1yl]propyl}-4-phenylisochroman hydrochloride

EXAMPLE I-33

4-[3-(4-Phenylpiperidino)propyl]-4-phenylisochroman hydrochloride

EXAMPLE I-34

4-{3-[4-(Piperidino)piperidino]propyl}-4-phenylisochroman dihydrochloride

EXAMPLE I-35

3,4-Dihydro-1'-[3-(4-phenylisochroman-4-yl)propyl]spiro[naphthalene-2(1H),2'-piperidine]hydrochloride

EXAMPLE I-36

3,4-Dihydro-6-methoxy-1'-[3-(4-phenylisochroman-4-yl)propyl]spiro[naphthalene-2(1H),2'-piperidine]hydrochloride

EXAMPLE I-37

3,4-Dihydro-6,7-dimethoxy-1'-[3-(4-phenylisochroman-4-yl)propyl]spiro[naphthalene-2(1H),2'-piperidine]hydrochloride

EXAMPLE I-38

4-[3-(Benzylamino)propyl]-4-(p-fluorophenyl)isochroman hydrochloride

EXAMPLE I-39

4-{3-[4-(p-Fluorophenyl)piperazin-1-yl]propyl}-4-(p-fluorophenyl)isochroman dihydrochloride

EXAMPLE I-40

4-[3-(Benzylamino)propyl]-4-(p-chlorophenyl)isochroman hydrochloride

EXAMPLE I-41

4-{3-[4-(p-Fluorophenyl)piperazin-1-yl]propyl}-4-(p-chlorophenyl)isochroman dihydrochloride

EXAMPLE I-42

4-{3-[4-(2-Benzothiazolyl)piperazin-1-yl]propyl)-4-(p-chlorophenyl)isochroman trihydrochloride

EXAMPLE I-43

4-[3-(Benzylamino)propyl]-7-chloro-4-(p-chlorophenyl)isochroman hydrochloride

EXAMPLE I-44

4-{3-[4-(p-Fluorophenyl)piperazin-1-yl]propyl}-7-chloro-4-(p-chlorophenyl)isochroman dihydrochloride

EXAMPLE I-45

Methyl α-[3-(4-phenylisochroman-4-yl)propylamino]-m-toluate hydrochloride

EXAMPLE I-46

4-[3-(m-Methylbenzylamino)propyl]-4-phenylisochroman hydrochloride

EXAMPLE I-47

6,7-Dihydro-1'-[3-(4-phenylisochroman-4-yl)propyl]spiro[4-oxobenzo(b)thiophene-5(4H),2'-piperidine] hydrochloride

EXAMPLE I-48

3,4-Dihydro-6-methoxy-1'-[3-(4-phenylisochroman-4-yl)propyl]spiro[1-oxonaphthalene-2-(1H),2'-piperidine]hydrochloride

EXAMPLE I-49

3,4-Dihydro-1'-[3-(4-phenylisochroman-4-yl)propyl]spiro[1-oxonaphthalene-2(1H),2'-piperidine]hydrochloride

EXAMPLE I-50

3,4-Dihydro-6,7-dimethoxy-1'-{3-[4-(p-fluorophenyl)isochroman-4-yl]propyl}spiro[naphthalene-2(1H),2'-piperidine] hydrochloride

EXAMPLE I-51

4-Phenyl-4-{3-[1-(1,2,3,4-tetrahydronaphthylamino)]propyl]isochroman hydrochloride

EXAMPLE I-52

3,4-Dihydro-6,7-dimethoxy-1'-[4-(4-phenylisochroman-4-yl)butyl]spiro[naphthalene-2(1H),2'-piperidine]hydrochloride

EXAMPLE I-53

6,7-Dihydro-1'-[3-(4-phenylisochroman-4-yl)propyl]spiro[benzo[b]thiophene-5(4H),2'-piperidine hydrochloride

EXAMPLE I-54

4-{3-[N-Methyl-N-2-(3,4methylenedioxyphenyloxy)ethyl)amino]propyl}-4phenylisochroman hydrochloride

EXAMPLE I-55

4-{3-[(2-Biphenylmethyl)amino]propyl}-4-phenylisochroman hydrochloride

EXAMPLE I-56

4-{3-[3,4-Dimethoxyphenyl)ureido]propyl}-4-phenylisochroman

EXAMPLE I-57

1'-[3-(4-Phenylisochroman-4-yl)propyl]spiro{1H-benz[cd]indole-4(3H,5H), 2'-piperidine}-5-one hydrochloride

EXAMPLE I-58

6-Methoxy-1'-[3-(4-phenylisochroman-4-yl)propyl]spiro{1H-benz[cd]indole-4(3H,5H), 2'-piperidine}-5-one hydrochloride

EXAMPLE I-59

6-Methoxy-1'-[3-(4-phenylisochroman-4-yl)propyl]spiro{1H-benz[cd]indole-4(3H,5H), 2'-piperizin}hydrochloride

EXAMPLE I-60

4-[3-(6,7-dimethoxy-1,2,3,4-tetrahydroisoquinolin-2-ylpropyl]-4-phenylisochroman hydrochloride

EXAMPLE I-61

4-{3-[4-(2-Oxoindolin-3-yl)piperidino]propyl}-4-phenylisochroman

EXAMPLE I-62

4-[3-(Benzylamino)propyl]-4-(2-pyridyl)isochroman hydrochloride

EXAMPLE I-63

4-[3-(Isoindolin-2-yl)propyl]-4-phenylisochroman hydrochloride

EXAMPLE I-64

4-[3-Benzylamino)propyl]-4-(benzothiazolyl)isochroman hydrochloride

EXAMPLE I-65

3,4-dihydro-1'-[3-(6,7-dimethoxy-4-phenylisochroman-4-yl)propyl]spiro[naphthalene-2(1H),2'-piperidine]hydrochloride

EXAMPLE I-66

4-{3-[(2-naphthylmethyl)amino]propyl}-4-phenylisochroman hydrochloride

EXAMPLE I-67

4-Phenyl-4-{3-[3-(3,4,5-trimethoxyphenyl)propionylamino]propyl}isochroman

EXAMPLE I-68

4-[3-(8,9-dimethoxy-6,6-dimethyl-3-benzazocin-3-yl)propyl]-4-phenylisochroman hydrochloride

EXAMPLE I-69

4-[3-(N-Acetyl-benzylamino)propyl]-4-(benzothiazolyl)isochroman

EXAMPLE I-70

4-{3-[2-(1,2,3,4-tetrahydro-7-methoxynaphthyl)amino]propyl}-4-phenylisochroman hydrochloride The structural formulas, physical properties and NMR spectra of the respective compounds are shown in Tables 18, 19, 20, 21, 22, 23, 24, 25, 26, 27 and 28.

TABLE 18

[Structure: Ar-C(CH₂)ₘ-R' with a fused ring containing CH₂-O-CH₂ and phenyl bearing R⁰ · xHCl]

| Example | Ar | R⁰ | R' | m | x | Melting Point (°C.) | NMR (δ_ppm, CDCl₃) | Elemental Analysis [Found/(Calculated)] C H N |
|---|---|---|---|---|---|---|---|---|
| I-1 | phenyl | H | -N(imidazole) | 2 | 1 | Noncrystalline powder | 2.58(1H, ddd), 2.82(1H, ddd), 3.73 (1H, ddd), 3.89(1H, d), 4.00(1H, d), 4.22(1H, ddd), 4.91(2H, s), 6.70–7.40(12H, m). | C₂₀H₂₀N₂O·HCl·2/5H₂O 69.19 6.37 8.38 (69.01 6.37 8.38) |
| I-2 | phenyl | H | -N(morpholine) | 2 | 1 | 187–190 | 2.19–2.55(8H, m), 3.69(4H, t), 3.92 (2H, s), 4.86(2H, s), 6.93–7.07(2H, m), 7.10–7.34(7H, m) | C₂₁H₂₅NO₂·HCl·3/10H₂O 69.07 7.51 3.79 (69.05 7.34 3.83) |
| I-3 | phenyl | H | -N(phthalimide) | 2 | — | 162–164 | 2.45–2.70(2H, m), 3.57–3.91(2H, m), 4.00(2H, q), 4.90(2H, s), 7.00–7.11 (2H, m), 7.12–7.39(6H, m), 7.63–7.90 (5H, m) | C₂₅H₂₁NO₃ 77.72 5.42 3.87 (78.31 5.52 3.65) |
| I-4 | phenyl | H | -NHCH₂(phenyl) | 2 | 1 | 182–185 | 1.41(1H, br s), 2.29–2.82(4H, m), 3.70(2H, s), 3.91(2H, q), 4.84(2H, s), 6.92–7.34(14H, m) | C₂₄H₂₅NO·HCl 75.82 6.97 3.62 (75.87 6.90 3.69) |
| I-5 | phenyl | H | -NHCH₂(3-OCH₃-phenyl) | 2 | 1 | 165–167 | 1.42(1H, br s), 2.29–2.81(4H, m), 3.69(2H, s), 3.78(3H, s), 3.91(2H, q), 4.85(2H, s), 6.74–7.30(13H, m) | C₂₅H₂₇NO₂·HCl·1/5H₂O 72.44 6.94 3.53 (72.61 6.92 3.39) |

TABLE 18-continued
| Example | R' | R⁰ | Ar | m | x | Melting Point (°C.) | NMR (δ$_{ppm}$, CDCl$_3$) | Elemental Analysis [Found/(Calculated)] C H N |
|---|---|---|---|---|---|---|---|---|
| I-6 | 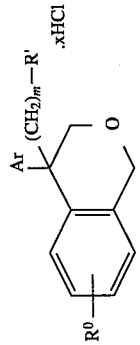 | H | 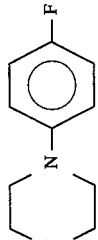 | 2 | 2 | 238–240 | 2.23–2.61(8H, m), 3.19(4H, t), 3.94 (2H, s), 4.87(2H, s), 6.79–7.08(5H, m), 7.09–7.30(9H, m) | C$_{27}$H$_{30}$N$_2$O.2HCl 68.53 6.98 5.81 (68.78 6.84 5.94) |
| I-7 |  | H |  | 2 | 1 | 234–237 | 2.25–2.63(8H, m), 3.11(4H, t), 3.95 (2H, s), 4.88(2H, s), 6.82–7.26 (13H, m) | C$_{27}$H$_{30}$FN$_2$O.HCl.7/5H$_2$O 67.94 6.60 5.85 (67.81 6.91 5.86) |

TABLE 19

| Example | R' | R° | Ar | m | x | Melting Point (°C.) | NMR (δ$_{ppm}$, CDCl$_3$) | Elemental Analysis [Found/Calculated] C H N |
|---|---|---|---|---|---|---|---|---|
| I-8 | -N(piperazine)-N=C$_6$H$_4$-Cl (3-Cl) | H | phenyl | 2 | 1 | 221–224 | 2.23–2.52(4H, m), 2.55(4H, t), 3.18 (4H, t), 3.94(2H, s), 4.87(2H, s), 6.71–6.89(3H, m), 6.95–7.36(10H, m) | C$_{27}$H$_{29}$ClN$_2$O.HCl 68.97 6.47 5.86 (69.08 6.44 5.97) |
| I-9 | -N(piperazine)-N=pyridyl | H | phenyl | 2 | 2 | 195–198 | 2.22–2.60(8H, m), 3.53(4H, t), 3.94 (2H, s), 4.87(2H, s), 6.59(1H, d), 6.62(1H, m), 6.95–7.07(2H, m), 7.08–7.34(7H, m), 7.40–7.50(1H, m), 8.15–8.19(1H, m) | C$_{26}$H$_{29}$N$_3$O.2HCl.1/2H$_2$O 65.12 6.88 8.95 (64.86 6.70 8.73) |
| I-10 | -N(piperazine)-NCH$_2$-phenyl | H | phenyl | 2 | 2 | 230–232 | 2.18–2.58(12H, m), 3.49(2H, s), 3.93 (2H, s), 4.85(2H, s), 6.93–7.31(14H, m), | C$_{28}$H$_{32}$N$_2$O.2HCl 69.04 7.20 5.92 (69.27 7.06 5.77) |
| I-11 | -N(piperidine)-phenyl | H | phenyl | 2 | 1 | 222–226 | 1.71–2.09(6H, m), 2.21–2.60(5H, m), 2.99–3.10(2H, m), 3.95(2H, s), 4.87 (2H, s), 6.97–7.09(2H, m), 7.10–7.35 (12H, m) | C$_{28}$H$_{31}$NO.HCl.1/5H$_2$O 76.82 7.37 3.25 (76.85 7.46 3.20) |
| I-12 | spiro tetrahydronaphthalene-piperidine | H | phenyl | 2 | 1 | Noncrystal-line powder | 1.40–1.80(10H, m), 2.10–2.80(10H, m) 3.91(2H, s), 4.87(2H, s), 6.90–7.30 (13H, m). | C$_{31}$H$_{35}$NO.HCl.2H$_2$O 72.81 7.62 2.38 (72.99 7.90 2.75) |
| I-13 | spiro dimethoxy-tetrahydronaphthalene-piperidine | H | phenyl | 2 | 1 | Noncrystal-line powder | 1.35–1.82(8H, m), 2.10–2.72(10H, m), 3.80(3H, s), 3.82(3H, s), 3.92(2H, s), 4.82(2H, s), 6.48(1H, d), 6.54 (1H, d), 6.91–7.30(9H, m) | C$_{33}$H$_{39}$NO$_3$.HCl.5/2H$_2$O 68.44 7.83 2.42 (68.36 7.21 2.51) |

TABLE 19-continued

| Example | R' | R° | Ar | m | x | Melting Point (°C.) | NMR (δ$_{ppm}$, CDCl$_3$) | Elemental Analysis [Found/Calculated] C H N |
|---|---|---|---|---|---|---|---|---|
| I-14 | -N⟨N⟩ | H | ⟨phenyl⟩ | 3 | 1 | Noncrystal- line powder | 1.60–2.30(4H, m), 3.85(2H, s), 3.89 (2H, t), 4.87(2H, s), 6.85(2H, m), 7.00–7.30(9H, m), 7.43(1H, s). | C$_{21}$H$_{22}$N$_2$O.HCl.5/4H$_2$O 67.11 6.66 7.46 (66.83 6.81 7.42) |

TABLE 20

| Example | R' | R° | Ar | m | x | Melting Point (°C.) | NMR (δ_ppm, CDCl_3) | Elemental Analysis [Found/(Calculated)] C H N |
|---|---|---|---|---|---|---|---|---|
| 1-15 | azepan-1-yl | H | phenyl | 3 | 1 | Noncrystalline powder | 1.40–1.70(10H, m), 2.17(2H, dt), 2.44(2H, t), 2.53(4H, br s), 3.92 (2H, d), 4.87(2H, s), 6.90–7.30 (9H, m) | $C_{24}H_{31}NO \cdot HCl \cdot 2H_2O$ 68.09 8.08 3.30 (68.31 8.60 3.32) |
| 1-16 | 2,3,4,5-tetrahydro-1H-benzo[c]azepin-2-yl | H | phenyl | 3 | 1 | Noncrystalline powder | 1.40–1.60(2H, m), 2.20(2H, dt), 2.46 (2H, t), 2.56(4H, dd), 2.89(4H, dd), 3.92(2H, s), 4.88(2H, s), 6.90– | $C_{28}H_{31}NO \cdot HCl \cdot 3/4H_2O$ 75.33 7.45 3.13 (75.14 7.55 3.13) |
| 1-17 | —NH-phenyl | H | phenyl | 3 | 1 | Noncrystalline powder | 1.50–1.80(2H, m), 2.29(2H, m), 3.10(2H, t), 3.92(2H, s), 4.88 (2H, s), 6.50–7.30(14H, m). | $C_{24}H_{25}NO \cdot HCl \cdot H_2O$ 72.18 7.09 3.22 (72.44 7.09 3.52) |
| 1-18 | —NHCH_2-phenyl | H | phenyl | 3 | 1 | Noncrystalline powder | 1.40–1.60(2H, m), 2.22(2H, dt), 2.63 (2H, t), 3.74(2H, s), 3.91(2H, s), 4.87(2H, s), 6.90–7.30(14H, m). | $C_{25}H_{27}NO \cdot HCl \cdot 1/4H_2O$ 75.54 7.21 3.31 (75.35 7.21 3.52) |
| 1-19 | —NHCH_2-(2-fluorophenyl) | H | phenyl | 3 | 1 | Noncrystalline powder | 1.39–1.62(2H, m), 2.09–2.37(2H, m), 2.62(2H, t), 3.79(2H, s), 3.90(2H, s), 4.86(2H, s), 6.93–7.33(13H, m) | $C_{25}H_{26}FNO \cdot HCl$ 72.59 6.77 3.50 (72.89 6.61 3.40) |
| 1-20 | —NHCH_2-(2-chlorophenyl) | H | phenyl | 3 | 1 | Noncrystalline powder | 1.40–1.60(2H, m), 2.23(2H, dt), 2.62 (2H, t), 3.83(2H, s), 3.91(2H, s), 4.87(2H, s), 6.90–7.40(14H, m). | $C_{25}H_{26}ClNO \cdot HCl \cdot 1/4H_2O$ 69.40 6.30 3.16 (69.36 6.30 3.16) |

TABLE 20-continued

| Example | R' | R° | Ar | m | x | Melting Point (°C.) | NMR ($\delta_{ppm}$, CDCl$_3$) | Elemental Analysis [Found/(Calculated)] C H N |
|---|---|---|---|---|---|---|---|---|
| I-21 | −NCH$_2$−Ph / CH$_3$ | H | Ph | 3 | 1 | Noncrystalline powder | 1.40–1.60(2H, m), 2.12(3H, s), 2.20 (2H, dt), 2.36(2H, t), 3.42(2H, s), 3.91(2H, s), 4.86(2H, s), 6.90–7.30 (14H, m). | C$_{26}$H$_{29}$NO.HCl.H$_2$O 73.37 7.50 3.24 (73.31 7.57 3.29) |
| I-22 | −NHCH$_2$−(thiophene) | H | Ph | 3 | 1 | Noncrystalline powder | 1.40–1.60(2H, m), 2.23(2H, dt), 2.66 (2H, t), 3.91(2H, s), 3.94(2H, s), 4.87(2H, s), 6.80–7.30(12H, m). | C$_{23}$H$_{25}$NOS.HCl.3/5H$_2$O 67.13 6.59 3.15 (67.24 6.67 3.41) |

TABLE 21

| Example | R' | R⁰ | Ar | m | x | Melting Point (°C.) |
|---|---|---|---|---|---|---|
| I-23 | −NHCH₂−(pyridyl) 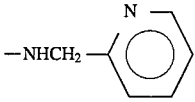 | H |  phenyl | 3 | 2 | Noncrystalline powder |
| I-24 | −NH(CH₂)₂−(phenyl) 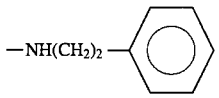 | H |  phenyl | 3 | 1 | Noncrystalline powder |
| I-25 | −NH(CH₂)₂−(phenyl)−OCH₃ with OCH₃ 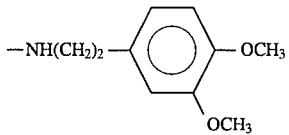 | H |  phenyl | 3 | 1 | Noncrystalline powder |
| I-26 | −NH(CH₂)₂−(pyridyl) 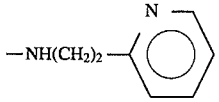 | H |  phenyl | 3 | 2 | Noncrystalline powder |
| I-27 | −NH(CH₂)₂−N(morpholino)O 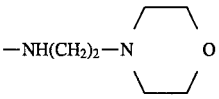 | H |  phenyl | 3 | 2 | Noncrystalline powder |
| I-28 | −NH−(indanyl) 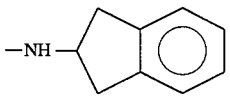 | H |  phenyl | 3 | 1 | Noncrystalline powder |

| Example | NMR (δ$_{ppm}$, CDCl₃) | Elemental Analysis [Found/(Calculated)] | | |
|---|---|---|---|---|
| | | C | H | N |
| I-23 | 1.55(2H, m), 1.24(2H, dt), 2.67(2H, t), 3.87(2H, s), 3.91(2H, s), 4.86 (2H, s), 6.90–7.30(11H, m), 7.63(1H, dt), 8.54(1H, m). | $C_{24}H_{26}N_2O\cdot 2HCl\cdot \tfrac{1}{2}H_2O$ 65.59 (65.45 | 6.37 6.63 | 6.52 6.36) |
| I-24 | 1.35–1.63(2H, m), 2.04–2.32(2H, m), 2.61(2H, t), 2.72–2.90(4H, m), 3.89 (2H, q), 4.86(2H, s), 6.92–7.35(14H, m) | $C_{26}H_{29}NO\cdot HCl\cdot \tfrac{1}{2}H_2O$ 75.03 (74.89 | 7.55 7.49 | 3.56 3.36) |
| I-25 | 1.40–1.60(2H, m), 2.18(2H, dt), 2.63(2H, t), 2.70–2.90(4H, m), 3.85 (s, 6H), 3.90(2H, s), 4.89(2H, s) 6.70–7.30(12H, m). | $C_{28}H_{33}NO_3\cdot HCl\cdot H_2O$ 69.43 (69.19 | 7.39 7.47 | 2.98 2.88) |
| I-26 | 1.49(2H, m), 2.19(2H, dt), 2.64 (2H, t), 2.97(4H, t), 3.90(2H, s), 4.86(2H, s), 6.90–7.30(11H, m), 7.59(1H, dt), 8.51(1H dt). | $C_{25}H_{28}N_2O\cdot 2HCl\cdot \tfrac{3}{2}H_2O$ 61.88 (62.16 | 6.73 6.58 | 5.98 6.30) |
| I-27 | 1.40–1.60(2H, m), 2.21(2H, dt), 2.44 (6H, m), 2.63(4H, m), 3.68(4H, t), 3.91(2H, s), 4.87(2H, s), 6.90–7.30 (2H, m). | $C_{24}H_{32}N_2O_2\cdot 2HCl\cdot \tfrac{1}{2}H_2O$ 61.94 (62.33 | 7.90 7.63 | 6.24 6.06) |
| I-28 | 1.40–1.60(2H, m), 2.22(2H, dt), 2.60–2.80(4H, m), 3.23(2H, dd), 3.58(1H, m), 3.91(2H, s), 4.86(2H, s), 6.90–7.30(13H, m). | $C_{27}H_{29}NO\cdot HCl\cdot \tfrac{1}{2}H_2O$ 75.28 (75.59 | 7.46 7.28 | 3.10 3.26) |

TABLE 22

| Example | R' | R⁰ | Ar | m | n | Melting Point (°C.) |
|---------|----|----|----|----|----|---------------------|
| I-29 | —N(piperazinyl)-phenyl | H | phenyl | 3 | 2 | 119–121 |
| I-30 | —N(piperazinyl)-(4-F-phenyl) | H | phenyl | 3 | 2 | 122–124 |
| I-31 | —N(piperazinyl)-benzothiazol-2-yl | H | phenyl | 3 | 2 | 152–154 |
| I-32 | —N(piperazinyl)-(benzisothiazol-3-yl) | H | phenyl | 3 | 1 | 222–227 |
| I-33 | —N(piperidinyl)-phenyl | H | phenyl | 3 | 1 | Noncrystalline powder |
| I-34 | —N(piperidinyl)-piperidinyl | H | phenyl | 3 | 2 | 265–267 |
| I-35 | spiro[piperidine-tetrahydronaphthalene] | H | phenyl | 3 | 1 | Noncrystalline powder |

| Example | NMR (δ_ppm, CDCl₃) | Elemental Analysis [Found/(Calculated)] C N H |
|---------|---------------------|-----|
| I-29 | 1.40–1.60(2H, m), 2.23(2H, m), 2.39(2H, t), 2.54(4H, t), 3.18(4H, t), 3.93(2H, s), 4.88(2H, s), 6.80–7.30(14H, m). | $C_{28}H_{32}N_2O \cdot 2HCl$<br>69.27  7.06  5.77<br>(69.27  7.05  5.96) |
| I-30 | 1.40–1.60(2H, m), 2.23(2H, m), 2.39(2H, t), 2.53(4H, dd), 3.09(4H, t), 3.92(2H, s), 4.88(2H, s), 6.80–7.30(13H, m). | $C_{28}H_{31}FN_2O \cdot 2HCl \cdot \frac{1}{2}H_2O$<br>65.74  6.51  5.67<br>(65.62  6.69  5.47) |
| I-31 | 1.40–1.70(2H, m), 2.22(2H, dt), 2.39(2H, t), 2.50(4H, t), 3.63(4H, t), 2.93(2H, s), 4.89(2H, s), 6.90–7.40(14H, m). | $C_{29}H_{31}N_3OS \cdot 2HCl \cdot \frac{1}{2}H_2O$<br>62.57  6.20  7.87<br>(62.53  6.26  7.54) |
| I-32 | 1.40–1.70(2H, m), 2.25(2H, dt), 2.42(2H, t), 2.60(4H, dd), 3.54(4H, t), 3.93(2H, s), 4.88(2H, s), 7.00–7.50(11H, m), 7.80(1H, d), 7.99(1H, d). | $C_{29}H_{31}N_3OS \cdot HCl \cdot \frac{3}{4}H_2O$<br>67.08  6.32  8.39<br>(67.03  6.69  8.08) |
| I-33 | 1.40–2.50(13H, m), 3.98(2H, br d), 3.93(2H, s), 4.88(2H, s), 7.00–7.30(14H, m). | $C_{29}H_{33}NO \cdot HCl \cdot \frac{9}{10}H_2O$<br>75.34  7.58  3.30<br>(75.02  7.77  3.02) |
| I-34 | 1.40–2.40(23H, m), 2.56(4H, t), 2.92(2H, br d), 3.91(2H, s), 4.87(2H, s), 6.90–7.30(9H, m). | $C_{28}H_{38}N_2O \cdot 2HCl$<br>67.19  8.38  5.57<br>(66.80  8.62  5.99) |
| I-35 | 1.30–2.00(10H, m), 2.10–2.90(10H, m), 3.91(2H, dd), 4.87(2H, s), 6.90–7.30(13H, m). | $C_{32}H_{37}NO \cdot HCl \cdot \frac{1}{4}H_2O$<br>73.99  8.00  2.32<br>(73.96  8.05  2.69) |

TABLE 23

| Example | R' | R⁰ | Ar | m | n | Melting Point (°C.) |
|---|---|---|---|---|---|---|
| I-36 | 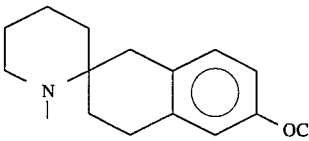 | H |  | 3 | 1 | Noncrystalline powder |
| I-37 | 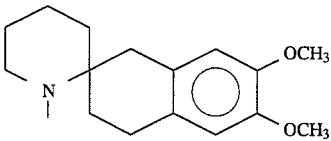 | H |  | 3 | 1 | Noncrystalline powder |
| I-38 | 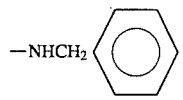 | H |  | 3 | 1 | Noncrystalline powder |
| I-39 | 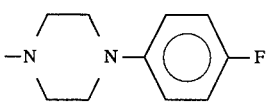 | H | 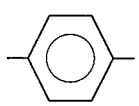 | 3 | 2 | 112–115 |
| I-40 | 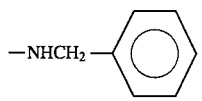 | H |  | 3 | 1 | Noncrystalline powder |
| I-41 | 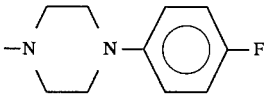 | H |  | 3 | 2 | 139–142 |
| I-42 | 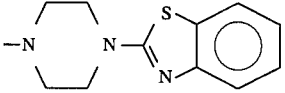 | H |  | 3 | 3 | 145–147 |

| Example | NMR (δ$_{ppm}$, CDCl$_3$) | Elemental Analysis [Found/(Calculated)] | | |
|---|---|---|---|---|
| | | C | N | H |
| I-36 | 1.30–1.90(10H, m), 2.10–2.80(10H, m), 3.77(3H, s), 3.91(1H, d), 3.92(1H, d), 4.97(2H, s), 6.64(2H, m), 6.90–7.30(10H, m). | C$_{33}$H$_{39}$NO$_2$.HCl.¾H$_2$O 74.62 (74.55) | 7.66 (7.87) | 2.86 (2.63) |
| I-37 | 1.30–2.00(10H, m), 2.10–2.90(10H, m), 3.83(6Hx5/7, s), 3.85(6Hx2/7, s), 3.91(2H, d), 4.88(2H, s), 6.55(2Hx 2/7, s), 6.58(2Hx5/7, s), 6.90–7.30 (9H, m). | C$_{34}$H$_{41}$NO$_3$.HCl.9/10H$_2$O 72.76 (72.35) | 7.57 (7.82) | 2.61 (2.48) |
| I-38 | 1.40–1.60(2H, m), 2.19(2H, dt), 2.62 (2H, t), 3.74(2H, s), 3.87(2H, s), 4.85(2H, s), 6.90–7.30(12H, m). | C$_{25}$H$_{26}$FNO.HCl.¾H$_2$O 70.87 (70.57) | 6.80 (6.75) | 3.17 (3.29) |
| I-39 | 1.40–1.60(2H, m), 2.20(2H, m), 2.41(2H, t), 2.53(4H, t), 3.09(4H, t), 3.89(2H, s), 4.87(2H, s), 6.80–7.30(12H, m). | C$_{28}$H$_{30}$FN$_2$O.2HCl 62.75 (62.54) | 6.69 (6.34) | 5.18 (5.21) |
| I-40 | 1.30–1.60(2H, m), 2.18(2H, dt), 2.62 2H, t), 3.73(2H, s), 3.87(2H, s), 4.85(2H, s), 6.90–7.30(13H, m). | C$_{25}$H$_{26}$ClNO.HCl.H$_2$O 67.12 (67.25) | 6.15 (6.55) | 3.11 (3.14) |
| I-41 | 1.40–1.60(2H, m), 2.20(2H, m), 2.37(2H, t), 2.53(4H, t), 3.10(4H, t), 3.89(2H, s), 4.87(2H, s), 6.80–7.30(12H, m). | C$_{28}$H$_{30}$FN$_2$O.2HCl.½H$_2$O 61.74 (61.37) | 6.17 (6.25) | 5.01 (5.11) |
| I-42 | 1.30–1.60(2H, m), 2.21(2H, m), 2.37(2H, t), 2.49(4H, t), 3.62(4H, t), 3.89(2H, s), 4.87(2H, s), 6.90–7.40(10H, m), 7.57(2H, t). | C$_{29}$H$_{30}$ClN$_2$OS.3HCl.¼H$_2$ 56.28 (56.36) | 5.73 (5.46) | 6.70 (6.80) |

TABLE 24

| Example | R' | R⁰ | Ar | m | x | Melting Point (°C.) |
|---|---|---|---|---|---|---|
| I-43 | 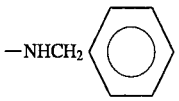 | 7-Cl | 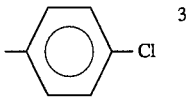 | 3 | 1 | Noncrystalline powder |
| I-44 | 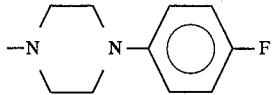 | 7-Cl | 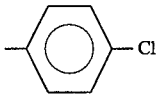 | 3 | 2 | 122–125 |
| I-45 | 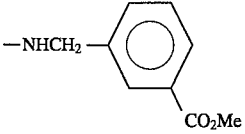 | H |  | 3 | 1 | 71–76 |
| I-46 | 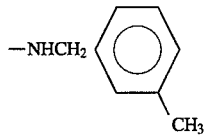 | H |  | 3 | 1 | Noncrystalline powder |
| I-47 | 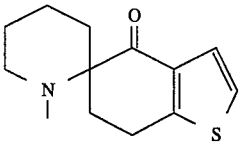 | H |  | 3 | 1 | Noncrystalline powder |
| I-48 | 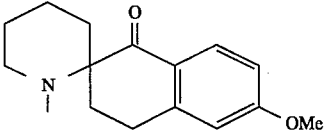 | H |  | 3 | 1 | Noncrystalline powder |

| Example | NMR ($\delta_{ppm}$, CDCl$_3$) | Elemental Analysis [Found/(Calculated)] | | |
|---|---|---|---|---|
| | | C | N | H |
| I-43 | 1.30–1.60(2H, m), 2.16(2H, dt), 2.62 (2H, t), 3.74(2H, s), 3.84(2H, s), 4.80(2H, s), 6.85–7.30(12H, m). | $C_{25}H_{25}Cl_2NO \cdot HCl \cdot H_2O$ 62.73  5.82  2.69 (62.45  5.87  2.91) | | |
| I-44 | 1.30–1.60(2H, m), 2.18(2H, m), 2.37(2H, t), 2.53(4H, t), 3.10(4H, t), 3.86(2H, s), 4.82(2H, s), 6.80–7.30(11H, m). | $C_{28}H_{29}Cl_2FN_2O \cdot 2HCl$ 58.68  5.74  4.67 (58.76  5.46  4.89) | | |
| I-45 | 1.40–1.62(2H, m), 2.08–2.37(2H, m), 2.62(2H, t), 3.78, 3.90, 4.86(2H each, s), 3.90(3H, s), 6.96, 7.02(1H each, dd), 7.06–7.30(6H, m), 7.37(1H, t), 7.49, 7.91(1H each, dt), 7.96(1H, s) | $C_{27}H_{29}NO_3 \cdot HCl \cdot \frac{1}{3}H_2O$ 69.47  6.56  3.01 (69.53  6.83  3.00) | | |
| I-46 | 1.50(2H, m), 2.21(2H, m), 2.33(3H, (2H, t), 3.74(2H, s), 3.84(2H, s), 4.80(2H, s), 6.85–7.30(12H, m) | $C_{26}H_{29}NO \cdot HCl \cdot 0.8H_2O$ 73.83  7.58  3.32 (73.93  7.54  3.32) | | |
| I-47 | 1.40–1.85(8H, m), 2.10–2.60(7H, m), 2.90–3.20(3H, m), 3.91(2H, s), 4.85 (2H, s), 6.95–7.50(11H, m). | $C_{30}H_{33}NO_2S \cdot HCl \cdot 1.5H_2O$ 67.20  7.04  2.41 (67.33  6.97  2.41) | | |
| I-48 | 1.34–1.84(4H, m), 1.95–2.15(3H, m), 2.20–2.65(4H, m), 2.82–3.11(3H, m), 3.84(3H, s), 3.88(3H, s), 4.84(2H, s), 6.65(1H, d), 6.83(1H, dd), 6.92–7.04(2H, m), 7.06–7.31(7H, m), 8.01(1H, dd). | $C_{33}H_{37}NO_3 \cdot HCl \cdot 1.2H_2O$ 70.57  7.13  2.74 (70.89  7.39  2.51) | | |

TABLE 25

| Example | R' | R⁰ | Ar | m | x | Melting Point (°C.) |
|---|---|---|---|---|---|---|
| I-49 | 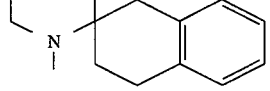 | H |  | 3 | 1 | Noncrystalline powder |
| I-50 | 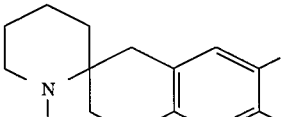 | H |  | 3 | 1 | Noncrystalline powder |
| I-51 | 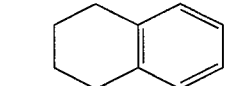 | H |  | 3 | 1 | Noncrystalline powder |
| I-52 | 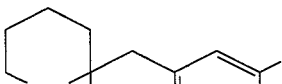 | H |  | 4 | 1 | Noncrystalline powder |
| I-53 | 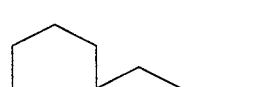 | H |  | 3 | 1 | Noncrystalline powder |

| Example | NMR ($\delta_{ppm}$, CDCl$_3$) | Elemental Analysis [Found/(Calculated)] | | |
|---|---|---|---|---|
| | | C | N | H |
| I-49 | 1.47–1.87(8H, m), 1.96–2.14(3H, m), 2.20–2.68(4H, m), 2.86–3.08(3H, m), 3.87(2H, s), 4.84(2H, s), 6.92–7.04 (2H, m), 7.08–7.36(8H, m), 7.44(2H, dt), 7.99–8.06(1H, m). | C$_{32}$H$_{35}$NO$_2$.HCl.1.5H$_2$O 72.16 (72.64) | 7.17 (7.43) | 2.81 (2.65) |
| I-50 | 1.30–2.00(10H, m), 2.10–2.90(10H, m), 3.80–3.90(8H, m), 4.87(2H, s), 6.56–6.58(2H, m), 6.90–7.30(8H, m). | C$_{34}$H$_{40}$FNO$_3$.HCl.2.5H$_2$O 67.07 (66.82) | 7.33 (7.59) | 2.14 (2.29) |
| I-51 | 1.50(2H, m), 1.60–2.00(4H, m), 2.10–2.40(2H, m), 2.60–2.80(4H, m), 3.70(1H, t), 3.92(2H, s), 4.87(2H, s), 6.95–7.35(13H, m). | C$_{28}$H$_{31}$NO.HCl.H$_2$O 74.73 (74.40) | 7.40 (7.58) | 2.97 (3.10) |
| I-52 | 1.19–1.38(1H, m), 1.37–1.92(11H, m), 2.08–2.37(4H, m), 2.51–2.85(6H, m), 3.83(6H, s), 3.90, 4.87(2H each, s), 6.54, 6.56(1H each, s), 6.94–7.34 (9H, m) | C$_{35}$H$_{43}$NO$_3$.HCl.H$_2$O 72.48 (72.45) | 7.87 (7.99) | 2.56 (2.41) |
| I-53 | 1.35–2.95(15H, m), 3.91(2H, d), 4.88('2H, s), 6.91(1H, q), 6.98–7.50(10H, m) | C$_{30}$H$_{35}$NOS.HCl.H$_2$O 70.18 (70.36) | 7.17 (7.48) | 2.56 (2.78) |

TABLE 26

| Example | R' | R⁰ | Ar | m | x | (%) Yield | Melting Point (°C.) |
|---------|----|----|-----|----|----|----|----|
| I-54 | —N(CH₃)(CH₂)₂O-(3,4-methylenedioxyphenyl) | H | phenyl | 3 | 1 | 69 | Noncrystalline powder |
| I-55 | —NHCH₂-(biphenyl) | | phenyl | 3 | 1 | 66 | Noncrystalline powder |
| I-56 | —NHCONH-(3,4-dimethoxyphenyl) | H | phenyl | 3 | — | 50 | 69–74 |
| I-57 | spiro-piperidine tetrahydronaphthalenone fused indole | H | phenyl | 3 | 1 | 79 | 183–188 |
| I-58 | spiro-piperidine methoxy-tetrahydronaphthalenone fused indole | H | phenyl | 3 | 1 | 83 | 174–179 |
| I-59 | spiro-piperidine methoxy-tetrahydronaphthalene fused indole | H | phenyl | 3 | 1 | 69 | 175–180 |

| Example | NMR (δ$_{ppm}$, CDCl₃) | Elemental Analysis [Found/(Calculated)] C  N  H |
|---------|----|----|
| I-54 | 1.39–1.61(2H, m), 2.14–2.26(2H, m), 2.26(3H, s), 2.43, 2.70(2H each, t), 3.91, 4.87(2H each, s), 3.95 (2H, t), 5.90(2H, s), 6.29(1H, dd), 6.47, 6.68 (1H each, d), 6.93–7.32(9H, m) | C₂₆H₃₁NO₄·HCl·H₂O<br>67.27  6.84  3.58<br>(67.26  6.85  2.80) |
| I-55 | 1.24–1.50(2H, m), 1.97–2.24(2H, m), 2.45(2H, t), 3.69, 4.84(2H each, s), 3.86(2H, q), 6.91(1H, dd), 6.99–7.44(17H, m) | C₃₁H₃₁NO·HCl·½H₂O<br>77.47  6.79  3.16<br>(77.72  6.94  2.92) |
| I-56 | 1.36–1.65(2H, m), 2.05–2.34(2H, m), 3.21(2H, q), 3.81 3.84(3H each, s), 3.87(2H, s), 4.83(2H, s), 4.84(1H, br t), 6.47(1H, br s), 6.66(1H, dd), 6.77(1H, d), 6.87–7.31(10H, m). | C₂₇H₃₀N₂O₄<br>72.79  6.77  6.10<br>(72.62  6.77  6.27) |
| I-57 | 1.35–1.79(8H, m), 2.00–2.30(2H, m), 2.33–2.72(3H, m), 2.99–3.16(1H, m), 3.30, 4.85(2H each, s), 3.93(2H, q), 6.97–7.31(11H, m), 7.50(1H, d), 7.62(1H, ddd), 8.47(1H, br s), | C₃₃H₃₄N₂O₂·HCl·H₂O<br>72.61  6.87  4.95<br>(72.71  6.84  5.14) |
| I-58 | 1.30–1.80(7H, m), 2.04–2.20(2H, m), 2.41–2.83(4H, m), 3.05(1H, dd), 3.07–3.30(1H, m), 3.34(1H, d), 3.90, 4.83(2H each, s), 3.94(3H, s), 6.85(1H, d), 6.94–7.30 (10H, m), 7.43(1H, dd), 8.42(1H, br s) | C₃₄H₃₆N₂O₃·HCl·½H₂O<br>70.10  6.91  4.85<br>(69.91  6.90  4.80) |
| I-59 | 1.30–1.66(9H, m), 2.10–2.34(2H, m), 2.37–2.79(5H, m), | C₃₄H₃₈N₂O₂·HCl·⅒H₂O |

TABLE 26-continued

| | | | |
|---|---|---|---|
| 2.80–3.19(2H, m), 3.85(3H, s), 3.92, 4.88(2H each, s), 6.80–6.87(2H, m), 6.95–7.31(10H, m), 7.66(1H, br s) | 73.40 (73.48 | 7.28 7.33 | 4.93 5.04) |

TABLE 27

| Example | R' | R⁰ | Ar | m | x | (%) Yield | Melting Point (°C.) |
|---|---|---|---|---|---|---|---|
| I-60 | 6,7-dimethoxy-tetrahydroisoquinolin-2-yl (N-Me) | H | phenyl | 3 | 1 | 67 | Noncrystalline powder |
| I-61 | 1-methylpiperidin-4-yl-CH(C(O)NH-o-tolyl)- | H | phenyl | 3 | — | 44 | Noncrystalline powder |
| I-62 | —NHCH₂—Ph | H | 2-methylpyridin-6-yl | 3 | 2 | 52 | 117–122 |
| I-63 | isoindolin-2-yl | H | phenyl | 3 | 1 | 51 | Noncrystalline powder |
| I-64 | —NHCH₂—Ph | H | 2-methylbenzothiazol-? | 3 | 1 | 70 | Noncrystalline powder |
| I-65 | spiro[piperidine-tetrahydronaphthalene] N-Me | 6,7-(OMe)₂ | phenyl | 3 | 1 | 57 | Noncrystalline powder |
| I-66 | —NHCH₂—naphthyl | H | phenyl | 3 | 1 | 80 | Noncrystalline powder |
| I-67 | —NHCO(CH₂)₂—(2,4,5-trimethoxyphenyl) | H | phenyl | 3 | — | 47 | Oil |

| | | Elemental Analysis [Found/(Calculated)] | | |
|---|---|---|---|---|
| Example | NMR (δ$_{ppm}$, CDCl₃) | C | N | H |
| I-60 | 1.52–1.72(2H, m), 2.20–2.35(2H, m), 2.49, 2.64, 2.80 (2H each, t), 3.48, 3.93, 4.88(2H each, s), 3.82, 3.83 (3H each, s), 6.49, 6.58(1H each, s), 6.99–7.33(9H, m), | C₂₉H₃₃NO₃·HCl·½H₂O 68.90 (68.69 | 7.17 7.35 | 2.65 2.76) |
| I-61 | 1.31–1.60(4H, m), 1.62–2.00(5H, m), 2.01–2.33(4H, m), 2.72–2.98(2H, m), 3.37(1H, d), 3.88(2H, q), 4.84(2H, s), 6.79–7.33(13H, m), 8.42(1H, br s) | C₃₁H₃₄N₂O₂·3.5H₂O 77.93 (77.99 | 7.26 7.43 | 6.20 5.87) |

TABLE 27-continued

| | | | |
|---|---|---|---|
| I-62 | 1.30–1.63(2H, m), 2.12–2.51(2H, m), 2.63(2H, t), 3.73, 4.85(2H each, s), 3.96, 4.29(1H each, d), 7.01–7.13(3H, m), 7.15–7.40(8H, m), 7.50(1H, dt), 8.59 (1H, ddd) | $C_{24}H_{26}N_2O \cdot 2HCl \cdot \frac{2}{5}H_2O$ | 63.82 6.91 5.53 (63.63 6.76 6.18) |
| I-63 | 1.43–1.76(2H, m), 2.18–2.43(2H, m), 2.71(2H, t), 3.85(4H, s), 3.94, 4.88(2H each, s), 6.98–7.07(2H, m), 7.10–7.31(11H, m) | $C_{26}H_{27}NO \cdot HCl \cdot \frac{2}{5}H_2O$ | 73.13 6.90 3.17 (73.03 7.17 3.28) |
| I-64 | 1.40–1.75(2H, m), 2.30–2.62(2H, m), 2.67(2H, t), 3.75, 4.89(2H each, s), 4.08, 4.42(1H each, d), 7.02–7.09(1H, m), 7.19–7.47(10H, m), 7.75, 8.00 (1H each, dd) | $C_{26}H_{26}N_2OS \cdot HCl \cdot \frac{3}{5}H_2O$ | 67.58 6.22 6.02 (67.62 6.15 6.07) |
| I-65 | 1.30–2.00(10H, m), 2.05–2.93(10H, m), 3.69(3H, s), 3.86(5H, s), 4.79(2H, s), 6.45(1H, s), 6.50(1H, s), 7.00–7.34(9H, m) | $C_{34}H_{41}NO_3 \cdot HCl \cdot \frac{2}{5}H_2O$ | 68.70 7.79 2.23 (68.84 7.99 2.36) |
| I-66 | 1.40–1.65(2H, m), 2.09–2.37(2H, m), 2.73(2H, t), 3.90 (2H, s), 4.19(2H, s), 4.86(2H, s), 6.92–7.33(9H, m), 7.38–7.55(4H, m), 7.70–7.99(2H, m), 8.05–8.70(1H, m) | $C_{26}H_{29}NO \cdot HCl \cdot \frac{1}{2}H_2O$ | 75.45 6.73 2.97 (75.39 6.98 3.03) |
| I-67 | 1.30–1.60(2H, m), 2.05–2.32(2H, m), 2.40(2H, t), 2.88 (2H, t), 3.23(2H, q), 3.79(3H, s), 3.80(6H, s), 3.88 (2H, s), 4.86(2H, s), 5.33(1H, br t), 6.39(2H, s), 6.88–7.33(9H, m) | $C_{28}H_{33}NO_4 \cdot \frac{1}{2}H_2O$ | 68.35 7.40 2.76 (68.21 7.16 2.84) |

TABLE 28

| Example | R' | R⁰ | Ar | m | x | (%) Yield | Melting Point (°C.) |
|---|---|---|---|---|---|---|---|
| I-68 | (bicyclic N-containing ring with OMe, OMe, Me, Me substituents) | H | phenyl | 3 | 1 | 56 | Noncrystalline powder |
| I-69 | –NHCH₂–phenyl / AC | H | phenyl | 3 | — | 99 | Oil |
| I-70 | –NH–tetrahydronaphthyl–OMe | H | (piperidine-fused ketone with NH) | 3 | 2 | 55 | Noncrystalline powder |

| Example | NMR (δ_ppm, CDCl₃) | Elemental Analysis [Found/(Calculated)] | | |
|---|---|---|---|---|
| | | C | N | H |
| I-68 | 1.00–1.40(8H, m), 1.65–2.40(12H, m), 3.65–3.85(8H, m), 4.79(2H, s), 6.48(1H, s), 6.80–7.29(10H, m) | $C_{33}H_{41}NO_3 \cdot HCl \cdot \frac{1}{2}H_2O$ 70.31 (70.38 | 7.78 8.05 | 2.38 2.49) |
| I-69 | 1.35–1.75(2H, m), 1.90–2.30(5H, m), 3.15(1H, t), 3.36 (1H, t), 3.85(1H, d), 3.88(1H, s), 4.40–4.60(2H, m), 4.84(1H, s), 4.86(1H, s), 6.85–7.38(14H, m) | $C_{27}H_{29}NO_2 \cdot \frac{7}{10}H_2O$ 78.78 (79.02 | 7.20 7.47 | 3.41 3.41) |
| I-70 | 1.40–1.63(3H, m), 1.90–3.01(11H, m), 3.74(3H, s), 3.91(2H, s), 4.85(2H, s), 6.59(1H, d), 6.66(1H, dd), 6.95–7.30(10H, m) | $C_{31}H_{33}NO_2 \cdot HCl \cdot \frac{1}{2}H_2O$ 72.02 (72.29 | 7.10 7.24 | 2.78 2.72) |

EXAMPLE II-1

4-{2-[4-(p-Fluorophenyl)piperazin-1-yl]ethyl}-3,4-dihydro-4-phenylisoquinoline dihydrochloride 1-[4-(p-Fluorophenyl)piperazin-1-yl]-4-formylamino-3,3-diphenylbutane (7 g) was heated in polyphosphoric acid (70 g) at 170° C. with stirring for 2 hours. The reaction mixture was poured in ice-water (500 ml), made basic with concentrated aqueous ammonia and extracted with ethyl acetate. The extract was washed with water, dried over anhydrous sodium sulfate and concentrated to dryness. The residue was purified by silica gel column chromatography (ethyl acetate) and treated with hydrochloric acid to provide the title compound (3.5 g) as non-crystalline powder.

Compounds II-2~4 and II-6~15 were respectively synthesized in the same manner as Example II-1.

Compound II-2
3,4-Dihydro-4-(3-morpholinopropyl)-4-phenylisoquinoline hydrochloride Compound II-3
3,4-Dihydro-4-phenyl-4-[3-(phthalimido)propyl]isoquinoline hydrochloride Compound II-4
3,4-Dihydro-4-[3-(2,3,4,5-tetrahydro-1(H)-3-benzazepin-3-yl]propylisoquinoline dihydrochloride Compound II-6
3,4-Dihydro-4-(3-dimethylaminopropyl)-4-phenylisoquinolin dihydrochloride Compound II-7
4-[3-(N-Benzyl-N-methyl)aminopropyl]-3,4-dihydro-4-phenylisoquinoline dihydrochloride Compound II-8
4-Phenyl-4-[3-(4-phenylpiperazin-1-yl)propyl]isoquinoline Compound II-9
4-{3-[4-(p-Fluorophenyl)piperazin-1-yl]propyl}-3,4-dihydro- 4-phenylisoquinoline dihydrochloride Compound II-10
4-[3-(4-Benzylpiperazin-1-yl]propyl]-3,4-dihydro-4-phenylisoquinoline trihydrochloride Compound II-11
3,4-Dihydro-4-phenyl-4-[3-(4-phenylpiperidin-1-yl]propyl]isoquinoline dihydrochloride Compound II-12
4-(p-Chlorophenyl)-3,4-dihydro-4-(3-phthalimidopropyl)isoquinoline hydrochloride Compound II-13
4-(p-Chlorophenyl)-3,4-dihydro-4-[3-(4-phenylpiperazino)propyl]isoquinoline trihydrochloride Compound II-14
3-(p-Chlorphenyl)-3,4-dihydro-4-[3-(4-phenylpiperidino)propyl]isoquinoline dihydrochloride Compound II-15
4-(p-Chlorophenyl)-4-{3-[4-(p-fluorophenyl)-piperazin-1-yl]propyl}-3,4-dihydroisoquinoline dihydrochloride

EXAMPLE II-5

4-(3-Aminopropyl)-3,4-dihydro-4-phenylisoquinoline dihydrochloride

To a solution of 3,4-dihydro-4-phenyl-4-[3-(phthalimidopropyl)]isoquinoline (4.1 g) in methanol (100 ml) was added hydrazine hydrate (1.04 g) and the mixture was refluxed for 22 hours. The reaction mixture was concentrated to dryness and the residue was dissolved in ethyl acetate—1N aqueous sodium hydroxide solution. The organic layer was washed with water, dried over anhydrous sodium sulfate and concentrated to dryness. The residue was treated with hydrochloric acid to provide the title compound (2 g) as light-tan non-crystalline powder.

The structural formulas, physical properties and NMR spectra of the respective compounds are shown in Tables 29, 30 and 31.

TABLE 29

| Example | R' | R⁰ | Ar | m | x | Melting Point (°C.) |
|---------|-----|-----|-----|---|---|---------------------|
| II-1 | −N(piperazinyl)−phenyl−F | H | phenyl | 2 | 2 | Noncrystalline powder |
| II-2 | −N(morpholino) | H | phenyl | 3 | 1 | Noncrystalline powder |
| II-3 | −N(phthalimido) | H | phenyl | 3 | 1 | 140–143 |
| II-4 | −N(benzazepinyl) | H | phenyl | 4 | 2 | Noncrystalline powder |

TABLE 29-continued

| | | | | | | |
|---|---|---|---|---|---|---|
| II-5 | —NH$_2$ | H | (phenyl) | 3 | 2 | Noncrystalline powder |

| Example | NMR ($\delta_{ppm}$, CDCl$_3$) | Elemental Analysis [Found/(Calculated)] | | |
|---|---|---|---|---|
| | | C | N | H |
| II-1 | 2.10–2.50(4H, m), 2.54(4H, t), 3.09 (4H, t), 3.83(1H, dd), 4.31(1H, dd), 6.80–7.00(4H, m), 7.20–7.50(9H, m), 8.31(1H, s). | C$_{27}$H$_{28}$FN$_3$.2HCl.⅚H$_2$O 61.35 (61.02 | 6.55 6.64 | 7.49 7.91) |
| II-2 | 1.40–1.70(2H, m), 2.00–2.40(8H, m), 3.67(2H, t), 3.80(1H, dd), 4.25 (1H, dd), 7.20–7.50(9H, m), 8.30 (1H, s). | C$_{22}$H$_{26}$N$_2$O.HCl.2H$_2$O 62.38 (62.47 | 7.62 7.39 | 6.55 6.62) |
| II-3 | 1.38–1.58(1H, m), 1.67–1.89(1H, m), 1.94–2.25(2H, m), 3.64(2H, t), 3.77 (1H, dd), 4.25(1H, dd), 7.11–7.45 (9H, m), 7.66–7.76(2H, m), 7.77–7.87 (2H, m), 8.28(1H, t) | C$_{26}$H$_{22}$N$_2$O$_2$.HCl.½H$_2$O 71.01 (70.98 | 5.49 5.50 | 6.16 6.37) |
| II-4 | 1.26(1H, m), 1.58(1H, m), 2.07(2H, m), 2.41(2H, m), 2.54(4H, m), 2.88 (4H, m), 3.82(1H, dd), 4.27(1h, dd), 7.00–7.50(13H, m), 8.30(1H, s). | C$_{28}$H$_{30}$N$_2$.2HCl.⅔H$_2$O 69.93 (69.78 | 7.21 7.03 | 5.78 5.80) |
| II-5 | 1.11–1.38(1H, m), 1.25(2H, br s), 1.40–1.63(1H, m), 2.01–2.12(2H, m), 2.66(2H, t), 3.81(1H, dd), 4.28 (1H, dd), 7.14–7.48(9H, m), 8.30 (1H, t) | C$_{18}$H$_{20}$N$_2$.2HCl.½H$_2$O 62.82 (62.43 | 7.03 6.69 | 7.51 8.09) |

TABLE 30

| Example | R' | R⁰ | Ar | m | x | Melting Point (°C.) |
|---|---|---|---|---|---|---|
| II-6 | —N(CH$_3$)$_2$ | H | (phenyl) | 3 | 2 | 155–160 |
| II-7 | —N(CH$_3$)CH$_2$-(phenyl) | H | (phenyl) | 3 | 2 | 159–164 |
| II-8 | —N(piperazinyl)-(phenyl) | H | (phenyl) | 3 | — | Syrup |
| II-9 | —N(piperazinyl)-(phenyl)-F | H | (phenyl) | 3 | 2 | Noncrystalline powder |
| II-10 | —N(piperazinyl)-CH$_2$-(phenyl) | H | (phenyl) | 3 | 3 | 150–154 |
| II-11 | —N(piperidinyl)-(phenyl) | H | (phenyl) | 3 | 2 | Noncrystalline powder |

TABLE 30-continued

| Example | NMR (δ$_{ppm}$, CDCl$_3$) | Elemental Analysis [Found/(Calculated)] | | |
|---|---|---|---|---|
| | | C | N | H |
| II-6 | 1.12–1.36(1H, m), 1.41–1.63(1H, m), 2.00–2.11(2H, m), 2.14(6H, s), 2.13–2.25(2H, m), 3.81(1H, dd), 4.28(1H, dd), 7.15–7.46(9H, m), 8.29(1H, t) | C$_{20}$H$_{24}$N$_2$·2HCl·⅔H$_2$O 63.62 (63.26 | 7.83 7.33 | 6.89 7.38) |
| II-7 | 1.20–1.40(1H, m), 1.46–1.69(1H, m), 2.01–2.12(2H, m), 2.28–2.38(2H, m), 2.10(3H, s), 3.40(2H, s), 3.81 (1H, dd), 4.26(1H, dd), 7.13–7.45 (14H, m), 8.30(1H, t) | C$_{26}$H$_{28}$N$_2$·2HCl·½H$_2$O 69.60 (69.33 | 7.53 6.94 | 5.99 6.22) |
| II-8 | 1.16–1.41(1H, m), 1.40–1.70(1H, m), 2.00–2.15(2H, m), 2.26–2.41(2H, m), 2.50(4H, t), 3.16(4H, t), 3.82 (1H, dd), 4.27(1H, dd), 6.80–6.95 (3H, m), 7.14–7.46(11H, m), 8.30 (1H, dd) | | | |
| II-9 | 1.20–1.70(2H, m), 2.09(2H, m), 2.51 (4H, m), 3.09(4H, t), 3.83(1H, dd), 4.27(1h, dd), 6.80–7.00(4h, m), 7.10–7.50(9H, m), 8.31(1H, s). | C$_{28}$H$_{30}$FN$_5$·2HCl·2H$_2$O 63.07 (62.68 | 6.90 6.95 | 8.00 7.83) |
| II-10 | 1.20–2.50(14H, m), 3.49(2H, s), 3.80(1H, dd), 4.25(1H, dd), 7.10–7.40(14H, m), 8.29(1H, s). | C$_{29}$H$_{33}$N$_2$·3HCl·½H$_2$O 62.53 (62.20 | 7.24 7.02 | 7.42 7.50) |
| II-11 | 1.20(2.60 (13H, m), 2.95(2H, br d), 3.83(1H, dd), 4.27(1H, dd), 7.10–7.50(14H, m), 8.31(1H, br s). | C$_{29}$H$_{32}$N$_2$·2HCl·2H$_2$O 67.46 (67.30 | 7.25 7.40 | 5.47 5.41) |

TABLE 31

| Example | R¹ | R² | Ar | m | x | Melting point (°C.) | NMR ($\delta_{ppm}$, CDCl$_3$) | Elemental Analysis [Found/(Calculated)] | | |
|---|---|---|---|---|---|---|---|---|---|---|
| | | | | | | | | C | H | N |
| II-12 | phthalimide | H | 4-Cl-C$_6$H$_4$ | 3 | 1 | 136–141 | 1.38–1.59 (1H, m), 1.64–1.89 (1H, m), 1.96–2.22 (2H, m), 3.64 (2H, t), 3.73 (1H, dd), 4.23 (1H, dd), 7.10–7.48 (8H, m), 7.66–7.88 (4H, m), 8.26 (1H, t) | C$_{26}$H$_{21}$ClN$_2$O$_2$·HCl·1/2H$_2$O 65.99  4.91  5.85 (65.83  4.89  5.91) | | |
| II-13 | 4-phenylpiperazinyl | H | 4-Cl-C$_6$H$_4$ | 3 | 3 | 164–169 | 1.17–1.40 (1H, m), 1.45–1.68 (1H, m), 2.00–2.40 (2H, m), 2.27–2.42 (2H, m), 2.45–2.58 (4H, m), 3.17 (4H, t), 3.79 (1H, dd), 4.24 (1H, dd), 6.80–6.96 (3H, m), 7.17–7.49 (10H, m), 8.29 (1H, t) | C$_{28}$H$_{30}$ClN$_3$·3HCl 60.86  6.24  7.54 (60.77  6.01  7.59) | | |
| II-14 | 4-phenylpiperidinyl | H | 4-Cl-C$_6$H$_4$ | 3 | 2 | 165–170 | 1.20–1.40 (1H, m), 1.35–1.70 (1H, m), 1.68–1.88 (4H, m), 1.88–2.15 (4H, m), 2.20–2.55 (3H, m), 2.85–3.00 (2H, m), 3.79 (1H, dd), 4.25 (1H, dd), 7.14–7.48 (13H, m), 8.29 (1H, t) | C$_{29}$H$_{31}$ClN$_2$·2HCl·H$_2$O 65.36  7.13  4.80 (65.23  6.61  5.25) | | |
| II-15 | 4-(4-fluorophenyl)piperazinyl | 7-Cl | 4-Cl-C$_6$H$_4$ | 3 | 2 | Noncrystalline powder | 1.20–1.60 (2H, m), 2.05 (2H, m), 2.51 (4H, m), 3.09 (4H, t), 3.80 (1H, dd), 4.23 (1H, dd), 6.80–7.00 (4H, m), 7.10–7.40 (7H, m), 8.25 (1H, s) | C$_{28}$H$_{28}$Cl$_2$FN$_3$·2HCl·1/2H$_2$O 54.79  5.96  7.2 (54.74  5.74  6.84) | | |

EXAMPLE III-1

1,2,3,4-Tetrahydro-4-{2-[4-(p-fluorophenyl)-piperazin-1-yl]ethyl}-4-phenylisoquinoline dihydrochloride To a solution of 4-{2-[4-(p-fluorophenyl)piperazin-1-yl]ethyl}-3,4-dihydro-4-phenylisoquinoline (3.1 g) in ethanol (50 ml) was added sodium borohydride (0.774 g) and the mixture was stirred at room temperature for 1 hour. The reaction mixture was dissolved in iced water (50 ml) and extracted with ethyl acetate. The extract was washed with water, dried over anhydrous sodium sulfate and concentrated to dryness. The residue was purified by silica gel column chromatography (ethyl acetate) and treated with hydrochloric acid to provide the title compound (3.0 g) as non-crystalline powder.

Compounds III-2, III-4, III-7 and III-9~15 were respectively synthesized in the same manner as Example III-1.

Compound III-2
1,2,3,4-Tetrahydro-4-(3-morpholinopropyl)-4-phenylisoquinoline dihydrochloride Compound III-4
1,2,3,4-Tetrahydro-4-[3-(2,3,4,5-tetrahydro-1(H)-3-benzazepin-3-yl)]propyl-4-phenylisoquinoline dihydrochloride Compound III-7
4-[3-(N-Benzyl-N-methyl)aminopropyl]-1,2,3,4-tetrahydro-4-phenylisoquinoline dihydrochloride Compound III-9
4-{3-[4-(p-fluorophenyl)piperazin-1-yl]propyl}-1,2,3,4-tetrahydro-4-phenylisoquinoline dihydrochloride Compound III-10
4-[3-(4-Benzylpiperazin-1-yl)propyl]-1,2,3,4-tetrahydro-4-phenylisoquinoline trihydrochloride Compound III-11
1,2,3,4-Tetrahydro-4-phenyl-4-[3-(4-phenylpiperidino)propyl]isoquinoline dihydrochloride Compound III-13
4-(p-Chlorophenyl)-1,2,3,4-tetrahydro-4-[3-(4-phenylpiperazin-1-yl)propyl]isoquinoline dihydrochloride Compound III-14
4-(p-Chlorophenyl)-1,2,3,4-tetrahydro-4-[3-(4-phenylpiperidino)propyl]isoquinoline dihydrochloride Compound III-15
4-(p-Chlorophenyl)-4-{3-[4-(p-fluorophenyl)piperazin-1-yl]propyl}-1,2,3,4-tetrahydroisoquinoline dihydrochloride

EXAMPLE III-3

1,2,3,4-Tetrahydro-4-phenyl-4-[3-(phthalimido)propyl]isoquinoline hydrochloride

To a solution of 3,4-dihydro-4-phenyl-4-[3(phthalimido)propyl]isoquinoline (1 g) in ethanol (30 ml) was added 10% palladium-on-carbon (0.3 g) and hydrogenation was carried out at atmospheric pressure and temperature for 5 hours. The catalyst was then filtered off and the filtrate was concentrated to dryness. The residue was treated with hydrochloric acid to provide the title compound (0.77 g) as light-yellow powder.

Compounds III-5, 6, 8 and 12 were respectively synthesized in the same manner as Example III-3.

Compound III-5
4-(3-Aminopropyl)-1,2,3,4-tetrahydro-4-phenylisoquinoline dihydrochloride Compound III-6
4-[3-(Dimethylamino)propyl]-1,2,3,4-tetrahydro-4'-phenylisoquinoline dihydrochloride Compound III-8
1,2,3,4-Tetrahydro-4-phenyl-4-[3-(4-phenylpiperazin-1-yl)propyl]isoquinoline trihydrochloride Compound III-12
4-(p-Chlorophenyl)-1,2,3,4-tetrahydro-4-[3(phthalimido)propyl]isoquinoline The structural formulas, physical properties and NMR spectra of the above compounds are shown in Tables 32, 33 and 34.

TABLE 32

[Structure: Ar-(CH₂)ₘ-R' with adjacent CH₂-NH group on benzene bearing R⁰]

| Example | R' | R⁰ | Ar | m | x | Melting Point (°C.) | NMR (δ_ppm, CDCl₃) | Elemental Analysis [Found/(Calculated)] C / H / N |
|---|---|---|---|---|---|---|---|---|
| III-1 | piperazinyl-(4-fluorophenyl) | H | phenyl | 2 | 2 | Noncrystalline powder | 2.20–2.70 (8H, m), 3.11 (4H, t), 3.18 (1H, d), 3.28 (1H, d), 4.06 (2H, d), 6.80–7.30 (13H, m). | C₂₇H₃₀FN₃·2HCl·2H₂O  61.89 / 6.95 / 7.89  (61.83 / 6.95 / 7.89) |
| III-2 | morpholinyl | H | phenyl | 3 | 2 | Noncrystalline powder | 1.30–1.60 (2H, m), 2.10–2.40 (8H, m), 3.19 (2H, s), 3.68 (4H, t), 4.04 (2H, d), 7.00–7.30 (9H, m). | C₂₂H₂₈N₂O·2HCl·1/2H₂O  63.33 / 7.47 / 6.57  (63.15 / 7.47 / 6.70) |
| III-3 | phthalimido | H | phenyl | 3 | 1 | 146–150 | 1.50–1.80 (2H, m), 2.20–2.41 (2H, m), 3.35 (1H, d), 3.69 (1H, d), 3.69 (2H, m), 4.27 (2H, q), 7.09–7.36 (9H, m), 7.63–7.73 (2H, m), 7.73–7.82 (2H, m) | C₂₆H₂₄N₂O₂·HCl·1/2H₂O  70.74 / 6.04 / 6.16  (70.66 / 5.93 / 6.34) |
| III-4 | tetrahydroisoquinolinyl | H | phenyl | 3 | 2 | Noncrystalline powder | 1.30–1.60 (2H, m), 2.16 (2H, m), 2.46 (2H, t), 2.56 (4H, dd), 2.89 (4H, dd), 3.15 (1H, d), 3.25 (1H, d), 3.98 (1H, d), 4.12 (1H, d), 7.00–7.30 (13H, m). | C₂₈H₃₂N₂·2HCl·6/5H₂O  68.51 / 7.38 / 5.63  (68.47 / 7.47 / 5.70) |
| III-5 | —NH₂ | H | phenyl | 3 | 2 | 169–173 | 1.45–1.75 (2H, m), 2.09–2.42 (2H, m), 2.83 (2H, t), 3.24 (2H, q), 4.02 (2H, q), 4.72 (2H, br s), 6.97–7.30 (9H, m) | C₁₈H₂₂N₂·2HCl·3/5H₂O  61.86 / 7.69 / 7.93  (61.75 / 7.25 / 8.00) |
| III-6 | —N(CH₃)₂ | H | phenyl | 3 | 2 | 148–153 | 1.41–1.80 (2H, m), 2.18–2.30 (2H, m), 2.43 (6H, s), 2.53–2.70 (2H, m), 3.25 (2H, s), 4.10 (2H, q), 4.82 (1H, br s), 7.00–7.33 (9H, m) | C₂₀H₂₆N₂·2HCl·H₂O  62.62 / 8.51 / 7.23  (62.33 / 7.85 / 7.27) |

TABLE 33

| Example | R' | R⁰ | Ar | m | x | Melting Point (°C.) | NMR (δ$_{ppm}$, CDCl₃) | Elemental Analysis [Found/(Calculated)] C | H | N |
|---|---|---|---|---|---|---|---|---|---|---|
| III-7 | -NCH₂-Ph / CH₃ | H | phenyl | 3 | 2 | 150–155 | 1.31–1.58 (2H, m), 2.13 (3H, s), 2.16 (2H, t), 2.36 (2H, t), 3.18 (2H, q), 3.43 (2H, s), 4.04 (2H, q), 7.00–7.35 (14H, m) | C₂₆H₃₀N₂·2HCl·4/5H₂O 68.09 (68.20) | 7.44 (7.40) | 5.83 (6.12) |
| III-8 | 4-N-piperazinyl-Ph | H | phenyl | 3 | 3 | 175–179 | 1.36–1.41 (2H, m), 2.08–2.30 (2H, m), 2.39 (2H, t), 2.53 (4H, t), 3.17 (4H, t), 3.21 (2H, q), 4.05 (2H, q), 6.80–6.98 (3H, m), 7.00–7.30 (11H, m) | C₂₈H₃₃N₃·3HCl·1/5H₂O 64.07 (64.11) | 7.32 (6.99) | 7.67 (8.01) |
| III-9 | 4-F-Ph-piperazinyl | H | phenyl | 3 | 2 | 139–140 | 1.40–1.60 (2H, m), 2.18 (2H, m), 2.39 (2H, t), 2.52 (4H, t), 3.09 (4H, t), 3.21 (2H, d), 4.05 (2H, q), 6.80–7.40 (13H, m) | C₂₈H₃₂FN₃·2HCl·2H₂O 62.49 (62.44) | 7.15 (7.00) | 7.92 (7.80) |
| III-10 | N-CH₂-Ph piperazinyl | H | phenyl | 3 | 3 | 160–165 | 1.30–1.50 (2H, m), 2.10–2.50 (12H, m), 3.15 (1H, d), 3.24 (1H, d), 3.97 (1H, d), 3.97 (1H, d), 4.10 (1H, d), 7.00–7.30 (14H, m). | C₂₉H₃₅N₃·3HCl 62.89 (62.99) | 7.70 (7.29) | 7.53 (7.60) |
| III-11 | 4-Ph-piperidinyl | H | phenyl | 3 | 2 | 164–169 | 1.40–1.60 (2H, m), 1.70–2.60 (11H, m), 2.98 (2H, m), 3.17 (1H, d), 3.26 (1H, d), 4.03 (1H, d), 4.12 (1H, d), 7.00–7.30 (14H, m). | C₂₉H₃₄N₂·2HCl·H₂O 69.23 (69.45) | 7.95 (7.64) | 5.55 (5.59) |
| III-12 | phthalimido | H | 4-Cl-Ph | 3 | — | 139–143 | 1.49–1.80 (2H, m), 2.18 (2H, t), 3.13 (2H, q), 3.68 (2H, t), 4.02 (2H, q), 6.96–7.27 (8H, m), 7.69–7.89 (4H, m) | C₂₆H₂₃ClN₂O₂·8/5H₂O 67.85 (67.92) | 5.49 (5.74) | 5.89 (6.09) |
| III-13 | 4-N-piperazinyl-Ph | H | 4-Cl-Ph | 3 | 2 | 165–170 | 1.30–1.60 (2H, m), 2.03–2.23 (2H, m), 2.38 (2H, t), 2.52 (4H, t), 3.17 (4H, t), 3.17 (2H, q), 4.05 (2H, q), 6.80–6.96 (3H, m), 7.00–7.30 (10H, m) | C₂₈H₃₂ClN₃·2HCl·H₂O 62.79 (62.63) | 7.00 (6.76) | 7.81 (7.83) |

TABLE 34

| Example | R' | R⁰ | Ar | m | x | Melting Point (°C.) | NMR (δ_ppm, CDCl₃) | Elemental Analysis [Found/(Calculated)] C H N |
|---|---|---|---|---|---|---|---|---|
| III-14 | -N⟩—⟨phenyl⟩ | H | 4-Cl-phenyl | 3 | 2 | 182–187 | 1.33–1.59 (2H, m), 1.70–1.90 (4H, m), 1.89–2.23 (4H, m), 2.36 (2H, t), 2.30–2.55(1H, m), 2.89–3.04 (2H, m), 3.18 (2H, q), 4.05 (2H, q), 6.99–7.33 (13H, m) | $C_{29}H_{33}ClN_2 \cdot 2HCl \cdot H_2O$<br>65.35  7.24  4.89<br>(64.99  6.96  5.23) |
| III-15 | -N⟩N—⟨4-F-phenyl⟩ | 7-Cl | 4-Cl-phenyl | 3 | 2 | Noncrystalline powder | 1.30–1.60 (2H, m), 2.13 (2H, m), 2.38 (2H, t), 2.53 (4H, t), 3.00–3.20 (6H, m), 4.02 (2H, d), 6.80–7.30 (11H, m). | $C_{28}H_{30}Cl_2FN_3 \cdot 2HCl \cdot 3H_2O$<br>53.84  6.20  6.44<br>(53.77  6.12  6.72) |

EXAMPLE IV-1

4-{2-[4-(p-Fluorophenyl)piperazin-1-yl]ethyl}-1,2,3, 4-tetrahydro-2-methyl-4-phenylisoquinoline hydrochloride To a solution of 4-{2-[4-(p-fluorophenyl)piperazin-1-yl] ethyl}-1,2,3,4-tetrahydro-4-phenylisoquinoline (0.6 g) in ethanol (15 ml) was added 37% formalin (1 ml) as well as 10% palladium-on-carbon (0.25 g) and the mixture was stirred in hydrogen streams at atmospheric pressure and room temperature for 3 hours. The catalyst was then filtered off and the filtrate was concentrated to dryness. The residue was purified by silica gel column chromatography (ethyl acetate) and treated with hydrochloric acid to provide the title compound (0.43 g) as non-crystakkube powder.

Compounds IV-2, 7, 8 and 9 were respectively synthesized in the same manner as Example IV-1.

Compound IV-2
1,2,3,4-Tetrahydro-2-methyl-4-phenyl-4-[3-(phthalimido)propyl]isoquinoline hydrochloride Compound IV-7
1,2,3,4-Tetrahydro-2-methyl-4-phenyl-4-[3-(4-phenylpiperazin-1-yl)propyl]isoquinoline trihydrochloride Compound IV-8
4-{3-[4-(p-Fluorophenyl)piperazin-1-yl]propyl}-1,2,3,4-tetrahydro-2-methyl-4-phenylisoquinoline trihydrochloride Compound IV-9
4-(p-Chlorophenyl)-1,2,3,4-tetrahydro-2-methyl-4-[(3-phthalimido)propyl]isoquinoline hydrochloride

EXAMPLE IV-3

4-(3-Aminopropyl)-1,2,3,4-tetrahydro-2-methyl-4-phenylisoquinoline hydrochloride 2-Methyl-4-phenyl-4-[3-(phtalimido)propyl]-1,2,3,4-tetrahydroisoquinoline (2 g) was heated in methanol (50 ml) under reflux in the presence of hydrazine hydrate (0.5 g) for 17 hours. The reaction mixture was concentrated to dryness and the residue was dissolved in ethyl acetate - 1N sodium hydroxide solution. The organic layer was washed with water, dried over anhydrous sodium sulfate and concentrated to dryness. The residue was treated with hydrochloric acid to provide the title compound (1.5 g) as white powder.

Compound IV-10 was synthesized in the same manner as Example IV-3.

Compound IV-10
4-(3-Aminopropyl)-4-(chlorophenyl)-1,2,3,4-tetrahydro-2-methylisoquinoline hydrochloride

EXAMPLE IV-4

4-[3-Benzylamino)propyl]-1,3,3,4-tetrahydro-2-methyl-4-phenylisoquinoline hydrochloride To a solution of 4-(3-aminopropyl)-2-methyl-4-phenyl-1, 2,3,4-tetrahydroisoquinoline (0.4 g) and benzaldehyde (0.76 g) in ethanol (15 ml) was added 10% palladium-on-carbon (0.15 g) and hydrogenation was carried out at atmospheric temperature and room temperature overnight. From this reaction mixture the catalyst was filtered off and the filtrate was concentrated to dryness. The residue was purified by silica gel column chromatography and treated with hydrochloric acid to provide the title compound (0.38 g) as light-yellow powder.

EXAMPLE IV-5

1,2,3,4-Tetrahydro-2-methyl-4-phenyl-4-[3-(phenylureido]propyl]isoquinoline

To a solution of 4-(3-aminopropyl)-2-methyl-4-phenyl-1, 2,3,4-tetrahydroisoquinoline (0.4 g) in chloroform (10 ml) was added phenyl isocyanate (0.25 g) and the mixture was stirred at room temperature for 1.5 hours. The reaction mixture was concentrated to dryness and the residue was crystallized from methanolisopropyl ether to provide the title compound (0.39 g) as colorless powder.

Compound IV-6 and IV-24 was synthesized in the same manner as Example IV-5.

Compound IV-6
1,2,3,4-Tetrahydro-2-methyl-4-[3-(3-methoxyphenylureido)propyl]-4-phenylisoquinoline Compound IV-24
1,2,3,4-Tetrahydro-2-methyl-4-[3-phenylthioureido)propyl] -4-phenylisoquinoline

EXAMPLE IV-12

4-(p-Chlorophenyl)-2-methyl-4-[3-(4-phenylpiperazin-1-yl)propyl]-1,2,3,4-tetrahydroisoquinoline hydrochloride To a solution of 4-(p-chlorophenyl)-4-[3-(4-phenylpiperazin-1-yl)propyl]-1,2,3,4-tetrahydroisoquinoline (0.7 g) in acetonitrile (15 ml) was added formalin (0.64 ml). Then, sodium cyanoborohydride (0.16 g) was added portionwise with stirring. The mixture was stirred for 15 minutes, at the end of which time acetic acid was added dropwise until the solution became neutral. The mixture was further stirred for 2 hours and the reaction mixture was extracted with ethyl acetate-1N aqueous sodium hydroxide solution. The organic layer was washed with water, dried over anhydrous sodium sulfate and concentrated to dryness. The residue was purified by silica gel column chromatography and treated with hydrochloric acid to provide the title compound (0.6 g) as colorless powder.

Compounds IV-11, 13 and 14 were respectively synthesized in the same manner as Example IV-12.

Compound IV-11
4-(p-Chlorophenyl)-4-[3-(2-hydroxymethylbenzoylamino) propyl]-2-methyl-1,2,3,4-tetrahydroisoquinoline hydrochloride Compound IV-13
4-(p-Chlorophenyl)-2-methyl-4-[3-(4-phenylpiperidino) propyl]-1,2,3,4-tetrahydroisoquinoline trihydrochloride Compound IV-14
4-(p-Chlorophenyl)-4-{3-[4-(p-fluorophenyl)piperidino] propyl}-2-methyl-1,2,3,4-tetrahydroisoquinoline trihydrochloride

EXAMPLE IV-15

4-[3-(4-Benzylpiperazin-1-yl)propyl]-4-phenyl-2-propyl-1,2,3,4,-tetrahydroisoquinoline hydrochloride To a solution of 4-[3-(4-benzylpiperazin-1-yl)propyl]-4-phenyl-1,2,3,4-tetrahydroisoquinoline (0.62 g) in a mixture of acetonitrile (20 ml) and DMF (10 ml) were added 3-iodopropane (0.26 g) and potassium carbonate (0.38 g) and the mixture was stirred at room temperature for 2 days. The reaction mixture was concentrated to dryness and dissolved in water-ethyl acetate. The ethyl acetate layer was washed with water, dried over anhydrous sodium sulfate and concentrated to dryness. The residue was purified by silica gel column chromatography (chloroform-methanol=15:1) and treated with hydrochloric acid to provide the title compound (0.6 g) as non-crystalline powder.

Compound IV-16 was synthesized in the same manner as Example IV-15.

Compound IV-16
2-Benzyl-1,2,3,4-tetrahydro-4-[3-(morpholino)propyl]-4-phenylisoquinoline dihydrochloride

EXAMPLE IV-17

2-Acetyl-4-phenyl-4-{2-[4-(p-fluorophenyl)-piperazin-1-yl]propyl}-1,2,3,4-tetrahydroisoquinoline hydrochloride To a solution of 4-phenyl-4-{2-[4-(p-fluorophenyl)piperazin-1-yl]propyl}-1,2,3,4-tetrahydroisoquinoline (1.2 g) in methylene chloride (30 ml) was added acetic anhydride (0.33 ml) with ice-cooling and stirring and the mixture was further stirred at room temperature for 1 hour. The reaction mixture was then concentrated to dryness and the residue was purified by silica gel column chromatography (ethyl acetate-methanol=10:1) and treated with hydrochloric acid to provide the title compound (1.2 g) as white crystals.

Compounds IV-18, 21, 22 and 23 were synthesized in the same manner as Example IV-17.

Compound IV-18
2-(p-Bromobenzoyl)-4-(p-chlorophenyl)-1,2,3,4-tetrahydro-4-[2-(4-phenylpiperazin-1-yl)propyl]isoquinoline dihydrochloride Compound IV-21
2-Methanesulfonyl-4-phenyl-1,2,3,4-tetrahydro-4-{3-[2,3,4,5-tetrahydro-1-(H)-3-benzazepin-3-yl]propyl}isoquinoline dihydrochloride Compound 22
2-(2-Methylenesulfonyl)-4-phenyl-1,2,3,4-tetrahydro-4-{3-[4-(p-fluorophenyl)piperazin-1-yl]propyl}isoquinoline hydrochloride Compound 23
2-Methoxycarbonyl-4-(p-chlorophenyl)-1,2,3,4-tetrahydro-4-{3-[4-(p-fluorophenyl)piperazin-1-yl]propyl}isoquinoline hydrochloride

EXAMPLE IV-19

4-[3-(N-Benzyl-N-methylamino)propyl]-4-phenyl-2-phenylcarbamoyl-1,2,3,4-tetrahydroisoquinoline hydrochloride To a solution of 4-[3-(N-benzyl-N-methylamino)propyl]-4-phenyl-1,3,3,4-tetrahydroisoquinoline (0.8 g) in chloroform (20 ml) was added phenyl isocyanate (0.38 g) and the mixture was stirred at room temperature for 1.5 hours. The reaction mixture was concentrated to dryness and the residue was purified by silica gel column chromatography. The resulting syrup was treated with hydrochloric acid to provide the title compound (0.8 g) as colorless powder.

Compound IV-20 was synthesized in the same manner as Example IV-19.

Compound IV-20
1,2,3,4-Tetrahydro-4-{2-[4-(p-fluorophenyl)-piperazin-1-yl]ethyl}-2-(3-methoxyphenyl)carbamoyl-4-phenylisoquinoline hydrochloride The structural formulas, physical properties and NMR spectra of the respective compounds are shown in Tables 35, 36, 37, 38, 39 and 40.

TABLE 35

$$\text{R}^0\text{-Ar-C(CH}_2\text{)}_m\text{-R}'\text{-CH}_2\text{-N-R}''$$

| Example | R' | R⁰ | R'' | Ar | m | x | Melting Point (°C.) | NMR ($\delta_{ppm}$, CDCl$_3$) | Elemental Analysis [Found/(Calculated)] | | |
|---|---|---|---|---|---|---|---|---|---|---|---|
| | | | | | | | | | C | H | N |
| IV-1 | 4-(4-fluorophenyl)piperazin-1-yl | H | CH$_3$ | phenyl | 2 | 2 | Noncrystalline powder | 2.34 (3H, s), 2.58 (4H, t), 2.74 (2H, s), 3.11 (4H, t), 3.62 (2H, d), 6.80–7.00 (4H, m), 7.10–7.30 (9H, m). | C$_{28}$H$_{32}$FN$_3$·2HCl·5/2H$_2$O 61.48 7.21 7.61 (61.42) (7.18) (7.67) | | |
| IV-2 | phthalimido | H | CH$_3$ | phenyl | 3 | 1 | 191–194 | 1.50–1.87 (2H, m), 2.09–2.43 (2H, m), 2.32 (3H, s), 2.70 (2H, s), 3.59 (2H, s), 3.67 (2H, t), 6.87–6.93 (1H, m), 7.01–7.30 (8H, m), 7.65–7.75 (2H, m), 7.77–7.87 (2H, m) | C$_{27}$H$_{28}$N$_2$O$_2$·HCl·1/2H$_2$O 71.27 6.08 6.18 (71.12) (6.19) (6.14) | | |
| IV-3 | —NH$_2$ | H | CH$_3$ | phenyl | 3 | 2 | 183–189 | 1.16 (2H, br s), 1.28–1.60 (2H, m), 2.06–2.32 (2H, m), 2.34 (3H, s), 2.68 (2H, t), 2.71 (2H, s), 3.62 (2H, q), 6.91–6.97 (1H, m), 7.05–7.30 (8H, m) | C$_{19}$H$_{24}$N$_2$·2HCl·3/5H$_2$O 63.04 7.86 7.19 (62.67) (7.53) (7.69) | | |
| IV-4 | —NHCH$_2$-phenyl | H | CH$_3$ | phenyl | 3 | 2 | 157–162 | 1.38–1.65 (3H, m), 2.06–2.35 (2H, m), 2.33 (3H, s), 2.62 (2H, t), 2.70 (2H, s), 3.61 (2H, q), 3.74 (2H, s), 6.90–6.97 (1H, m), 7.05–7.37 (13H, m) | C$_{26}$H$_{30}$N$_2$·2HCl·1.65H$_2$O 67.15 7.56 5.57 (67.15) (7.46) (6.02) | | |

TABLE 36

| Example | R' | R⁰ | R" | Ar | m | x | Melting Point (°C.) | NMR (δ_ppm, CDCl₃) | Elemental Analysis [Found/(Calculated)] | | | |
|---|---|---|---|---|---|---|---|---|---|---|---|---|
| | | | | | | | | | | C | H | N |
| IV-5 | —NHCONH—(phenyl) | H | CH₃ | phenyl | 3 | — | 143–146 | 1.32–1.65 (2H, m), 2.03–2.35 (2H, m), 2.32 (3H, s), 2.68 (2H, s), 3.21 (2H, q), 3.60 (2H, q), 4.74 (1H, br t), 6.34 (1H, m), 6.85–6.91 (1H, m), 7.02–7.33 (13H, m) | C₂₆H₂₉N₃O·7/5H₂O | 73.26 (73.52 | 7.25 7.55 | 9.97 9.89) |
| IV-6 | —NHCONH—(3-OCH₃-phenyl) | H | CH₃ | phenyl | 3 | — | 153–155 | 1.36–1.69 (2H, m), 2.04–2.38(2H, m), 2.32 (3H, s), 2.69 (2H, s), 3.22 (2H, q), 3.60 (2H, q), 3.77 (3H, s), 4.73 (1H, br t), 6.24 (1H, br s), 6.60–6.66 (1H, m), 6.71–6.77 (1H, m), 6.86–6.96 (2H, m), 7.03–7.31 (9H, m) | C₂₇H₃₁N₃O₂ | 75.25 (75.49 | 7.27 7.27 | 9.48 9.78) |
| IV-7 | piperazinyl-N-phenyl | H | CH₃ | phenyl | 3 | 3 | 168–172 | 1.20–1.62 (2H, m), 2.13–2.30 (2H, m), 2.35 (3H, s), 2.38 (2H, t), 2.54 (4H, t), 2.72 (2H, s), 3.18 (4H, t), 3.63 (2H, q), 6.80–7.00 (4H, m), 7.02–7.31 (10H, m) | C₂₉H₃₅N₃·3HCl | 65.32 (65.11 | 7.68 7.16 | 7.73 7.85) |
| IV-8 | piperazinyl-N-(4-F-phenyl) | H | CH₃ | phenyl | 3 | 3 | 139–140 | 1.40–1.60 (2H, m), 2.10–2.30 (2H, m), 2.35 (3H, s), 2.38 (2H, t), 2.53 (4H, t), 2.72 (2H, s), 3.10 (4H, t), 3.62 (2H, d), 6.80–7.00 (4H, m), 7.05–7.30 (9H, m). | C₂₉H₃₄FN₃·3HCl·2H₂O | 59.37 (59.14 | 7.09 7.02 | 7.39 7.13) |

TABLE 37

| Example | R' | R⁰ | R" | Ar | m | x | Melting Point (°C.) | NMR (δ_ppm, CDCl₃) | Elemental Analysis [Found/(Calculated)] C H N |
|---------|----|----|----|----|----|----|---|---|---|
| IV-9 | phthalimido | H | CH₃ | 4-Cl-C₆H₄ | 3 | 1 | 176–181 | 1.43–1.83 (2H, m), 2.03–2.37 (2H, m), 2.31 (3H, s), 2.66 (2H, s), 3.57 (2H, s), 3.65 (2H, t), 6.84–6.92 (1H, m), 7.01–7.23 (7H, m), 7.67–7.85 (4H, m) | C₂₇H₂₅ClN₂O₂·HCl·3/10H₂O  66.91 6.00 5.43  (66.61 5.51 5.75) |
| IV-10 | —NH₂ | H | CH₃ | 4-Cl-C₆H₄ | 3 | 2 | 184–190 | 1.20–1.55 (2H, m), 1.50 (2H, br s), 2.00–2.30 (2H, m), 2.33 (3H, s), 2.66 (2H, t), 2.68 (2H, s), 3.61 (2H, s), 6.88–6.95 (1H, m), 7.03–7.30 (7H, m) | C₁₉H₂₃ClN₂·2HCl·7/10H₂O  57.38 7.29 6.34  (57.00 6.65 7.00) |
| IV-11 | 2-(HOCH₂)-C₆H₄-NHCO— | H | CH₃ | 4-Cl-C₆H₄ | 3 | 1 | 147–152 | 1.46–1.79 (2H, m), 2.11–2.46 (2H, m), 2.34 (3H, s), 2.70 (2H, q), 3.44 (2H, q), 3.64 (2H, q), 4.53 (2H, s), 4.87 (1H, br s), 6.69 (1H, br t), 6.82–6.89 (1H, m), 7.06–7.53 (11H, m) | C₂₇H₂₉ClN₂O₂·HCl·3/2H₂O  63.22 6.65 5.40  (63.28 6.65 5.40) |
| IV-12 | 4-phenylpiperazin-1-yl | H | CH₃ | 4-Cl-C₆H₄ | 3 | 3 | 176–182 | 1.30–1.63 (2H, m), 2.05–2.34 (2H, m), 2.34 (3H, s), 2.37 (2H, t), 2.54 (4H, t), 2.69 (2H, s), 3.18 (4H, t), 3.62 (2H, s), 6.82–6.99 (4H, m), 7.08–7.31 (9H, m) | C₂₉H₃₄ClN₃·3HCl·1/5H₂O  60.72 6.77 7.41  (60.78 6.58 7.33) |
| IV-13 | 4-phenylpiperidin-1-yl | H | CH₃ | 4-Cl-C₆H₄ | 3 | 2 | 172–177 | 1.35–1.63 (2H, m), 1.70–1.89 (4H, m), 1.89–2.24(4H, m), 2.34 (3H, s), 2.34 (2H, t), 2.38–2.56 (1H, m), 2.70 (2H, s), 2.97 (2H, d), 3.61 (2H, s), 6.90–6.98 (1H, m), 7.03–7.34 (12H, m) | C₃₀H₃₅ClN₂·2HCl·7/5H₂O  65.01 7.73 5.46  (64.67 7.20 5.03) |

TABLE 38

| Example | R' | R⁰ | R" | Ar | m | x | Melting Point (°C.) | NMR (δ_ppm, CDCl₃) | Elemental Analysis [Found/(Calculated)] C / H / N |
|---|---|---|---|---|---|---|---|---|---|
| IV-14 | -N(piperidine)-C₆H₄-F | 7-Cl | CH₃ | 4-Cl-C₆H₄- | 3 | 3 | 163–168 | 1.30–1.60 (2H, m), 2.15 (2H, m), 2.33 (3H, s), 2.37 (2H, t), 2.53 (4H, t), 2.66 (2H, s), 3.10 (4H, t), 3.57 (2H, s), 6.80–7.30 (11H, m). | C₂₉H₃₂Cl₂FN₃·3HCl·H₂O 54.31 6.12 6.38 (54.52 6.12 6.38) |
| IV-15 | -N(piperidine)-CH₂-C₆H₅ | H | ⁿPr | C₆H₅- | 3 | 3 | Noncrystalline powder | 0.84 (3H, t), 1.30–1.60 (4H, m), 2.00–2.50 (14H, m), 2.71 (2H, s), 3.49 (1H, s), 3.65 (2H, q), 6.70–(14H, m). | C₃₂H₄₁N₃·3HCl·5/2H₂O 62.00 7.79 6.77 (61.88 7.79 7.20) |
| IV-16 | -N(morpholine) | H | Bn | C₆H₅- | 3 | 2 | Noncrystalline powder | 1.30–1.60 (2H, m), 2.10–2.40 (8H, m), 2.75 (2H, s), 3.50–3.80 (8H, m), 6.90–7.30 (14H, m). | C₂₉H₃₄N₂O·2HCl·H₂O 67.14 7.50 5.25 (67.33 7.40 5.41) |
| IV-17 | -N(piperidine)-C₆H₄-F | H | Ac | C₆H₅- | 3 | 2 | 118–120 | 1.60–1.80 (2H, d), 2.06 (3H, s), 2.30 (3H, t), 3.00–3.80 (10H, m), 3.94 (1H, d), 4.08 (1H, d), 4.44 (1H, d), 4.77 (1H, d), 6.9–7.4 (13H, d). | C₃₀H₃₄FN₃O·2HCl·3/2H₂O 63.37 6.85 7.40 (63.04 6.88 7.35) |
| IV-18 | -N(piperidine)-C₆H₄-N | H | -CO-C₆H₄-Br | 4-Cl-C₆H₄- | 3 | 2 | 142–146 | 1.20–1.60 (2H, m), 1.94–2.32 (2H, m), 2.35 (2H, t), 2.51 (4H, t), 3.16 (4H, t), 3.58–3.94 (2H, m), 4.47–4.74 (1H, m), 4.98–5.17 (1H, m), 6.73–7.59 (17H, m) | C₃₅H₃₅BrClN₃O·2HCl 60.13 5.58 5.85 (59.89 5.31 5.99) |

TABLE 39

| Example | R' | R⁰ | R'' | Ar | m | x | Melting Point (°C.) | NMR (δ_ppm, CDCl₃) | Elemental Analysis [Found/(Calculated)] C | H | N |
|---|---|---|---|---|---|---|---|---|---|---|---|
| IV-19 | -NCH₂-CH₃ (phenyl) | H | -CONH- (phenyl) | phenyl | 3 | 1 | 189-192 | 1.30-1.59 (2H, m), 2.12 (3H, s), 2.21 (2H, t), 2.35 (2H, t), 3.42 (2H, s), 3.61 (1H, d), 4.06 (1H, d), 4.59 (2H, q), 5.80 (1H, br s), 6.92-7.05 (1H, m), 7.05-7.38 (18H, m) | C₃₃H₃₅N₃O.HCl 75.17 (75.34) | 6.98 6.90 | 8.16 7.99 |
| IV-20 | piperazinyl-(4-F-phenyl) | H | -CONH- (3-OCH₃-phenyl) | phenyl | 3 | 1 | 144-147 | 1.30-1.60 (2H, m), 2.24 (2H, t), 2.38 (2H, t), 2.51 (4H, m), 3.08 (4H, t), 3.65 (1H, d), 3.77 (3H, s), 4.09 (1H, d), 4.55 (1H, d), 4.66 (1H, d), 5.87 (1H, s), 6.50-6.70 (2H, m), 6.80-7.40 (15H, m). | C₃₆H₃₉FN₄O₂.HCl.13/10H₂O 67.44 (67.68) | 6.49 6.72 | 8.50 8.77 |
| IV-21 | tetrahydroisoquinolinyl | H | SO₂Me | phenyl | 3 | 1 | Noncrystalline powder | 1.51 (2H, m), 2.24 (2H, m), 2.46 (2H, t), 2.50-2.60 (7H, m), 2.89 (4H, m), 3.59 (2H, s), 4.36 (1H, d), 4.61 (1H, d), 7.00-7.30 (13H, m) | C₂₉H₃₄N₂O₂S.HCl.5/2H₂O 62.37 (62.63) | 6.81 7.25 | 5.09 5.04 |

TABLE 40

| Example | R' | R⁰ | R" | Ar | m | x | Yield (%) | Melting Point (°C.) | NMR ($\delta_{ppm}$, in CDCl$_3$) | Elemental Analysis [Found/(Calculated)] | | |
|---|---|---|---|---|---|---|---|---|---|---|---|---|
| | | | | | | | | | | C | H | N |
| IV-22 | -N(piperazine)-C$_6$H$_4$F | H | 3,5-Me$_2$-4-SO$_2$-C$_6$H$_2$-Me (mesityl-SO$_2$) | phenyl | 4 | — | 55 | Noncrystalline powder | 1.04–1.33 (2H, m), 1.35–1.55 (2H, m), 2.02, 2.28, (2H each, t), 2.28 (3H, s), 2.40 (6H, s), 2.54, 3.10 (4H each, t), 3.45, 4.44 (2H each, q), 6.79–7.28 (15H, m) | C$_{39}$H$_{44}$FN$_3$O$_2$S·6/5H$_2$O  70.24 (70.49) | 6.93 7.22 | 6.47 6.49 |
| IV-23 | -N(piperazine)-C$_6$H$_4$F | H | CO$_2$Me | 2-Cl-C$_6$H$_4$ | 3 | 1 | 63 | 123–128 | 1.25–1.62 (2H, m), 1.98–2.21 (2H, m), 2.35 (2H, t), 2.51, 3.09 (4H each t), 3.58–3.77 (4H, m), 3.83–4.11 (1H, m), 4.28–4.73 (2H, m), 6.81–7.00 (4H, m), 7.01–7.30 (8H, m) | C$_{30}$H$_{33}$FClN$_3$O$_2$·HCl·3/2H$_2$O  61.53 (61.54) | 6.21 6.37 | 7.30 7.18 |
| IV-24 | -NHC(=S)NH-C$_6$H$_5$ | H | CH$_3$ | phenyl | 3 | — | 65 | Noncrystalline powder | 1.38–1.76 (2H, m), 2.04–2.37 (2H, m), 2.31 (3H, s), 2.68 (2H, s), 3.48–3.68 (4H, m), 6.01 (1H, br s), 6.84 (1H, dd), 7.00–7.45 (13H, m), 7.83 (1H, br s) | C$_{26}$H$_{29}$N$_3$S·H$_2$O  71.91 (72.02) | 7.02 7.21 | 9.53 9.69 |

FORMULATION EXAMPLE 1

| | | |
|---|---|---|
| (1) Compound of Example I-45 | 10.0 g | |
| (2) Lactose | 60.0 g | |
| (3) Corn starch | 35.0 g | |
| (4) Gelatin | 3.0 g | |
| (5) Magnesium stearate | 2.0 g | |

Using 30 ml of an aqueous solution of gelatin (10% by weight, 3.0 g as gelatin), a mixture of 10.0 g of the compound obtained in Example 1-45, 60.0 g of lactose and 35.0 g of corn starch was granulated through a 1 mm-mesh sieve, dried at 40° C., and resieved. To the granulation thus obtained was added 2.0 g of magnesium stearate and the mixture was compressed. The core tablets thus prepared were coated with a coating composition comprising an aqueous suspension of sucrose, titanium dioxide, talc and gum arabic and, then, grazed with beeswax to provide 1000 coated tablets.

FORMULATION EXAMPLE 2

| | |
|---|---|
| (1) Compound of Example I-45 | 10.0 g |
| (2) Lactose | 70.0 g |
| (3) Corn starch | 50.0 g |
| (4) Soluble starch | 7.0 g |
| (5) Magnesium stearate | 3.0 g |

Using 70 ml of an aqueous solution of soluble starch (7.0 g as soluble starch), a mixture of 10.0 g of the compound obtained in Example 1-45 and 3.0 g of magnesium stearate was granulated. The granulation was dried and mixed with 70.0 g of lactose and 50.0 g of corn starch. The resulting composition was compressed to provide 1000 tablets.

FORMULATION EXAMPLE 3

| | |
|---|---|
| (1) Compound of Example I-36 | 10.0 g |
| (2) Lactose | 60.0 g |
| (3) Corn starch | 35.0 g |
| (4) Gelatin | 3.0 g |
| (5) Magnesium stearate | 2.0 g |

A mixture of 10.0 g of the compound obtained in Example 1-36, 60.0 g of lactose and 35.0 g of corn starch was passed through a 1 mm mesh sieve and granulated with 30 ml of 10 wt. % aqueous gelatin solution (3.0 g as gelatin) and the granulation was dried at 40° C. and re-sieved. The granules thus prepared were mixed with 2.0 g of magnesium stearate and the mixture was compressed. The resulting core tablets were coated with an aqueous suspension containing sucrose, titanium dioxide, talc and gum arabic. The coated tablets were then grazed with beeswax to provide 1000 tablets.

FORMULATION EXAMPLE 4

| | |
|---|---|
| (1) Compound of Example I-36 | 10.0 g |
| (2) Lactose | 70.0 g |
| (3) Corn starch | 50.0 g |
| (4) Soluble starch | 7.0 g |
| (5) Magnesium stearate | 3.0 g |

A mixture of 10.0 g of the compound obtained in Example 1-36 and 3.0 g of magnesium stearate was granulated with 70 ml of an aqueous solution of soluble starch (7.0 g as soluble starch) and the granulation was dried and mixed with 70.0 g of lactose and 50.0 g of corn starch. This mixture was compressed to provide 1000 tablets.

EXPERIMENTAL EXAMPLE 1

(A) Preparation of $^{125}I$-leuprolerin

Ten (10) μl of $3\times10^4$M aqueous leuprolerin solution and 10 μl of 0.01 mg/ml lactoperoxidase were taken in a tube and 10 μl of $Na^{125}I$ solution (37 MBq) was added. After stirring, 10 μl of 0.001% $H_2O_2$ was added and the reaction was conducted at room temperature for 20 minutes. Then, 700 μl of 0.05% TFA solution was added to the tube to terminate the reaction and the reaction mixture was purified by reverse-phase HPLC. The HPLC conditions are shown below. $^{125}I$-leuprolerin was eluted after a retention time of 26–27 minutes.

Column: TSKgel ODS-80T$_M$CTR (4.6 mm×10 cm)

Eluent: Solvent A (0.05% TFA); Solvent B (40% $CH_3CN$-0.05% TFA)

Min. 0 (100% Solvent A)–Min. 3 (100% Solvent A)–Min. 7 (50% Solvent A+50% Solvent B)–Min. 40 (100% Solvent B)

Elution temperature: room temperature

Elution speed: 1 ml/min.

(B) Preparation of a rat pituitary anterior lobe membrane fraction containing GnRH receptors Forty Wistar rats (8 weeks old, male) were sacrificed by decapitation under no anesthesia and the anterior lobe of the pituitary gland was isolated and washed with ice-cooled homogenate buffer [25 mM Tris (tris(hydroxymethyl)aminomethane)-HCl, 0.3M sucrose, 1 mM EGTA (glycoletherdiamine-N,N,N',N'-tetraacetic acid), 0.25 mM PMSF (phenylmethylsulfonyl fluoride), 10 U/ml aprotinin, 1 μg/ml pepstatin, 20 μg/ml leupeptin, 100 μg/ml phosphoramidon, 0.03% sodium azide, pH 7.5]. The pituitary tissue was floated in 2 ml of the homogenate buffer and homogenized using a Polytron homogenizer. The homogenate was centrifuged at 700×G for 15 minutes. The supernatant was taken in an ultracentrifuge tube and centrifuged at 100,000×G for 1 hour to provide a membrane fraction pellet. This pellet was suspended in 2 ml of assay buffer [25 mM Tris-HCl, 1 mM EDTA (ethylenediaminetetraacetic acid), 0.1% BSA (bovine serum albumin), 0.25 mM PMSP, 1 μg/ml pepstatin, 20 μg/ml leupeptin, 100 μg/ml phosphoramidon, 0.03% sodium azide, pH 7.5) and the suspension was centrifuged at 100,000×G for 1 hour. The membrane fraction recovered as a pellet was resuspended in 10 ml of assay buffer, divided into portions, preserved at −80° C. and thawed when needed.

(C) Preparation of a bovine pituitary anterior lobe membrane fraction containing GnRH receptors A bovine pituitary anterior lobe membrane fraction containing GnRH receptors was prepared by the same procedure as described under (B). However, a 10,000×G centrifugation supernatant was recentrifuged at 100,000×G for 1 hour to provide the membrane fraction pellet.

(D) Preparation of a CHO (Chinese hamster ovarian) cell membrane fraction containing human GnRH receptors A CHO cell line (109 cells) with human GnRH receptors expressed was suspended in 5 mM EDTA-supplemented phosphate-buffered physiological saline (PBS-EDTA) and centrifuged at 100×G for 5 minutes. To the cell pellet was added 10 ml of cell homogenate buffer (10 mM $NaHCO_3$, 5 mM EDTA, pH 7.5) and the mixture was homogenized using a Polytron homogenizer. The homogenate was centrifuged at 400×G for 15 minutes. The supernatant was taken in an ultracentrifuge tube and centrifuged at 100,000×G for 1 hour to provide a membrane fraction pellet. This pellet was suspended in 2 ml of assay buffer and centrifuged at 100,000×G for 1 hour. The membrane fraction recovered as a pellet was resuspended in 20 ml of assay buffer, divided into portions, preserved at −80° C. and thawed when needed.

(E) Determination of the $^{125}$I-leuprolerin binding inhibition rate

For the rat and human membrane fractions prepared in (B) and (D), each membrane fraction was diluted with assay buffer to a concentration of 200 µg/ml and distributed in 188 µl portions into tubes. As to the bovine membrane fraction prepared in (C), the membrane fraction was diluted with assay buffer to 750 µg/ml and distributed in 188 µl portions into tubes. Where the rat pituitary anterior lobe membrane fraction was used, 2 µl of a 0.1 mM solution of the compound in 60% DMSO (dimethyl sulfoxide) and 10 µl of 38 nM $^{125}$-leuprolerin solution were simultaneously added. Where the bovine pituitary anterior lobe fraction or the cell membrane fraction of the CHO with human GnRH receptors expressed, 2 µl of a 2 mM solution of the compound in 60% DMSO and 10 µl of 38 nM $^{125}$-leuprolerin solution were simultaneously added. For determining the maximum binding amount, a reaction system comprising 2 µl of 60% DMSO and 10 µl of 38 nM $^{125}$I-leuprolerin solution was prepared. On the other hand, for determining the nonspecific binding amount, a reaction system comprising 2 µl of 100 µM leuprolerin in 60% DMSO and 10 µl of 38 nM $^{125}$I-leuprolerin was also prepared at the same time.

Where the rat or bovine pituitary anterior lobe membrane fraction was used, the reaction was conducted at 4° C. for 90 minutes. Where the membrane fraction of the CHO with human GnRH receptors expressed was used, the reaction was carried out at 25° C. for 60 minutes. After each reaction, the reaction mixture was filtered under suction through a polyethyleneimine-treated Whatman glass filter (GF-F). After filtration, the radioactivity of $^{125}$I-leuprolerin remaining on the filter was measured with a γ-counter.

The expression (TB-SB)/(TB-NSB)×100 (where SB=radioactivity with the compound added, TB=maximum bound radioactivity, NSB=nonspecifically bound radioactivity) was calculated to find the binding inhibition rate of each test compound. Furthermore, the inhibition rate was determined by varying the concentration of the test substance and the 50% inhibitory concentration (IC$_{50}$) of the compound was calculated from Hill plot. The results are shown in Table 41.

TABLE 41

| Example No. | GnRH receptor binding inhibition test | | |
|---|---|---|---|
| | Binding inhibitory activity (IC$_{50}$ µM) | | |
| of compound | Human | Rat | Bovine |
| I-24 | — | 0.9 | 7 |
| I-35 | — | 0.7 | 6 |
| I-36 | 0 | 0.6 | 11 |
| I-37 | — | 0.03 | 6 |
| I-45 | 6 | 0.5 | 5 |
| I-46 | — | 0.5 | 14 |
| I-47 | — | 0.3 | 7 |
| I-48 | — | 0.4 | 10 |
| I-49 | — | 0.5 | 10 |
| I-50 | — | 0.08 | 8 |
| I-51 | — | 0.5 | 10 |
| I-52 | 6 | 0.03 | 5 |

It is apparent from Table 41 that the compound (I) or salt of this invention has excellent GnRH receptor binding inhibitory activity.

EXPERIMENTAL EXAMPLE 2

Assay of Monoamine Uptake-antagonizing Activity (a) Activity to inhibit serotonine (5-HT) uptake The experiment was performed in accordance with the method of Hyttel et al. [Psychopharmacology 60, 13, 1978]. The whole brain of a rat was homogenized in 40 volumes of ice-cooled 0.32M sucrose solution containing 10 µM pargyline and, then, centrifuged (600×G) for 10 minutes. The supernatant was centrifuged (2500×G) for 55 minutes to provide a pellet. This pellet was suspended in Krebs-Ringer-phosphate buffer (pH 7.4; 122 mM NaCl, 4.82 mM KCl, 0.972 mM CaCl$_2$, 1.21 mM MgSO$_4$, 12.7 mM Na$_2$HPO$_4$, 2.97 mM NaH$_2$PO$_4$, 0.162 mM EDTA sodium, 10 mM glucose, 1.14 mM ascorbic acid) saturated with a mixed gas (95% O and 5% CO$_2$). To 900 µl of this suspension was added a solution of the test drug (10 µl) in DMSO and the mixture was incubated at 37° C. for 5 minutes. Then, 100 µl of 3H-5-HT (final concentration 10 nM) was added and the mixture was further incubated at 37° C. for 5 minutes. This reaction mixture was filtered under suction using a GF/B filter and the filter was washed with 4 ml of the above-mentioned buffer. The radioactivity on the filter was measured by the liquid scintillation method.

The amount of the drug which caused a 50% decrease in 5-HT uptake is shown as 50% inhibitory activity (IC$_{50}$) in Table 42.

TABLE 42

| Example No. of Compound | 5-HT uptake inhibitory activity (IC$_{50}$ µM) |
|---|---|
| I-6 | 1.0 |
| I-12 | 0.022 |
| I-18 | 0.8 |
| I-24 | 0.26 |
| I-25 | 0.14 |
| I-30 | 0.068 |
| I-33 | 0.27 |
| I-35 | 0.13 |
| I-36 | 0.0051 |
| II-7 | 0.88 |
| II-8 | 0.41 |
| II-13 | 0.14 |
| III-7 | 0.2 |
| III-8 | 0.16 |
| III-9 | 0.17 |
| IV-7 | 0.18 |
| IV-13 | 0.13 |
| IV-19 | 0.23 |
| IV-20 | 0.03 |

It is apparent from Table 42 that the compound (I) or salt of this invention has excellent serotonine uptake antagonizing activity.

(b) Activity to inhibit norepinephrine (NE) uptake

Using the rat cerebral cortex and, as the substrate, $^3$H-NE, an experiment was performed by otherwise the same procedure as described for 5-HT. See Table 43.

TABLE 43

| Example No. of Compound | NE uptake inhibitory activity (IC$_{50}$ µM) |
|---|---|
| I-12 | 0.015 |
| I-24 | 0.22 |
| I-25 | 0.39 |

TABLE 43-continued

| Example No. of Compound | NE uptake inhibitory activity (IC$_{50}$ μM) |
|---|---|
| I-30 | 0.59 |
| I-33 | 0.55 |
| I-35 | 0.30 |
| I-36 | 0.41 |
| IV-19 | 0.56 |
| IV-20 | 0.12 |

It is apparent from Table 43 that the compound (I) or salt of this invention has excellent norepinephrine uptake antagonizing activity.

$^{45}Ca^{2+}$ uptake inhibition experiment

The rat cerebral cortex was homogenized in 10 volumes of ice-cooled 0.32M sucrose solution to prepare a crude synaptosome fraction (100×G, 10 min., 12000×G, 20 min.). This fraction was homogenized in Tris buffer [132 mM sodium chloride, 5 mM potassium chloride, 1.3 mM magnesium chloride, 1.2 mM sodium dihydrogen phosphate, 1.2 mM calcium chloride, 10 mM glucose; adjusted to pH 7.5 with 20 mM Tris base and saturated with mixed gas (95% oxygen and 5% carbon dioxide)]. To 900 μl of the homogenate was added a DMSO solution of the test drug (10 μl). The mixture was incubated at 37° C. for 10 minutes, followed by addition of 100 μl of a veratrine solution (containing 0.18 μci $^{45}Ca^{2+}$) at a final veratrine concentration of M. The mixture was incubated at 37° C. for 10 minutes, quenched with 4 ml of ice-cooled EGTA solution (120 mM sodium chloride, 5 mM potassium chloride, 5 mM EGTA, pH=7.5) and suction-filtered using a GF/B filter. The filter was washed twice with 4 ml each of a washing solution (132 mM sodium chloride, 5 mM potassium chloride, 1.3 mM magnesium chloride, 1.2 mM calcium chloride, 20 mM Tris base, pH 7.5) and the radioactivity of the pooled wash was measured by the liquid scintillation method. The results are shown in Table 44.

The $^{45}Ca^{2+}$ uptake inhibition rate was calculated by means of the following equation.

FORMULA 1

$$\text{Inhibition rate} = \frac{A - B}{C - D}$$

A: The $^{45}Ca^{2+}$ uptake after 10 minutes' stimulation with 30 μM veratrine in the presence of the test drug B: The $^{45}Ca^{2+}$ uptake in the absence of veratrine and in the presence of the test drug C: The $^{45}Ca^{2+}$ uptake after 10 minutes' stimulation with 30 μM veratrine in the absence of the test drug D: The $^{45}Ca^{2+}$ uptake in the absence of the test drug and in the absence of veratrine

TABLE 44

| Example No. of Compound | $^{45}Ca^{2+}$ uptake inhibitory activity (IC$_{50}$ μM) |
|---|---|
| I-6 | 0.32 |
| I-12 | 0.85 |
| I-15 | 1.25 |
| I-18 | 1.32 |
| I-19 | 1.05 |
| I-20 | 0.94 |
| I-23 | 0.50 |

TABLE 44-continued

| Example No. of Compound | $^{45}Ca^{2+}$ uptake inhibitory activity (IC$_{50}$ μM) |
|---|---|
| I-24 | 1.77 |
| I-25 | 1.19 |
| I-30 | 1.59 |
| I-33 | 0.69 |
| I-35 | 0.14 |
| I-36 | 0.76 |
| II-7 | 0.46 |
| II-8 | 1.84 |
| II-13 | 1.29 |
| III-7 | 1.77 |
| III-8 | 1.63 |
| III-9 | 1.44 |
| IV-7 | 1.71 |
| IV-13 | 0.32 |
| IV-19 | 0.95 |
| IV-20 | 0.17 |

It is apparent from Table 44 that the objective compound (I) or salt of this invention has excellent calcium ion uptake antagonizing activity.

What is claimed is:

1. A compound of the formula

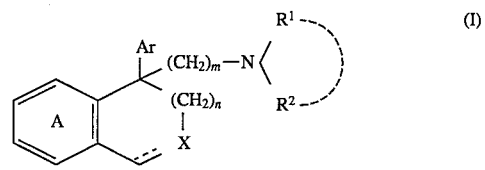

wherein ring A represents a benzene ring which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, hydroxy, amino, mono($C_{1-6}$)alkylamino, di($C_{1-6}$)alkylamino, carboxy, $C_{1-6}$ alkoxycarbonyl, $C_{1-7}$ acylamino and methylenedioxy;

Ar represents (i) a $C_{6-14}$ aryl or (ii) a 5- or 6-membered heteroaromatic group having 1 to 3 hetero-atoms selected from the group consisting of nitrogen, oxygen and sulfur, each of which groups (i) and (ii) may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxy-carbonyl, $C_{1-7}$ acylamino and methylenedioxy;

$R^1$ and $R^2$ independently represent (i) hydrogen atom, (ii) a group of the formula: —CO—R, —CONH—R, —SO$_2$—R or —CO—OR wherein R represents a $C_{1-6}$alkyl, $C_{2-6}$ alkenyl, C2-6 alkynyl, $C_{3-6}$ cycloalkyl, $C_{6-14}$ aryl or $C_{7-16}$ aralkyl group which may be substituted with 1 to 3 substituents selected from the group consisting of halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$) alkylamino, di($C_{1-6}$) alkylamino, carboxy, $C_{1-6}$ alkoxy-carbonyl, $C_{1-7}$ [acylamnio] acylamino, methylenedioxy, oxo, thioxo, phenyl, phenylamino, phenyloxy and methylenedioxyphenyloxy, or (iii) a $C_{1-6}$ alkyl, $C_{2-6}$ alkenyl, C2-6 alkynyl, $C_{3-6}$ cycloalkyl, $C_{6-14}$ aryl or $C_{7-16}$ aralkyl group which may be substituted with 1 to 3 substituents selected from the group consisting of halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxy-carbonyl and $C_{1-7}$ acylamino, methylenedioxy, oxo, thioxo, phenyl, phenylamino, phenyloxy and methylenedioxyphenyloxy;

or $R^1$ and $R^2$ taken together with the adjacent nitrogen atoms represent (i) a 5- or 6-membered nitrogen-containing hetero-aromatic group having 1 to 3 hetero-atoms selected from the group consisting of nitrogen, oxygen and sulfur, which hetero-aromatic group may be substituted with 1 to 3 substituents selected from the group consisting of halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$alkoxy-carbonyl and $C_{1-7}$ acylamino,

(ii)

wherein ring B may be substituted with 1 or 2 oxo groups and may be fused to one benzene ring which may be substituted with 1 to 3 substituents selected from the group consisting of halogen atoms, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxy-carbonyl and $C_{1-7}$ acylamino, p represents an integer of 4 to 7;

(iii)

wherein Z represents —O—, >CH—W or >N—W in which W represents (a) hydrogen atom, (b) a $C_{6-14}$ aryl or $C_{7-16}$ aralkyl group, which aryl or aralkyl group may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxy-carbonyl and $C_{1-7}$ acylamino or (c) a 5- to 11-membered aromatic or non-aromatic heterocyclic group containing 1 to 3 hetero atoms selected from the group consisting of nitrogen, sulfur and oxygen atoms in addition to carbon atoms, which may be substituted with 1 to 3 substituents selected from the group consisting of halogen, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$) alkylamino, carboxy, $C_{1-6}$ alkoxy-carbonyl and $C_{1-7}$ acylamino, methylenedioxy, oxo, thioxo, phenyl, phenylamino, phenyloxy and methylenedioxyphenyloxy,

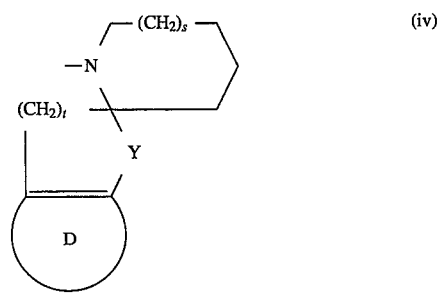

(iv)

wherein ring D represents (a) a benzene ring or (b) a 5- or 6-membered heteroaromatic ring having 1 to 3 hetero-atoms selected from nitrogen, oxygen and sulfur, each of which rings (a) and (b) may be substituted with 1 to 3 substituents selected from the group consisting of halogen atoms, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxy-carbonyl and $C_{1-7}$ acylamino, Y represents —$CH_2$—, —CO— or —CH(OH)—, s and t individually represent an integer of 1 to 3, or

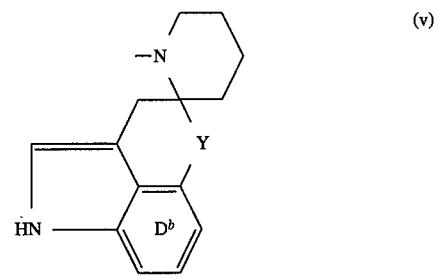

(v)

wherein ring $D^b$ represents a benzene ring which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxycarbonyl and $C_{1-7}$ acylamino, Y is —$CH_2$—, —CO— or —CH(OH)—;

m represents an integer of 1 to 6;

n represents 1;

---- represents a single bond;

X represents —O—;

or a pharmaceutically acceptable salt thereof.

2. A compound as claimed in claim 1, wherein Ar represents a phenyl group which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$) alkylamino, di($C_{1-6}$)alkylamino, carboxy, $C_{1-6}$ alkoxy-carbonyl and $C_{1-7}$ acylamino.

3. A compound as claimed in claim 1, wherein $R^1$ represents hydrogen atom and $R^2$ represents a aralkyl which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$alkoxy-carbonyl and $C_{1-7}$ acylamino.

4. A compound as claimed in claim 1, wherein $R^1$ and $R^2$ taken together with the adjacent nitrogen atom form

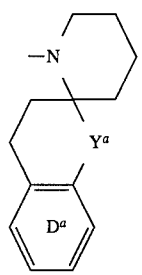

wherein ring $D^a$ represents a benzene ring which may be substituted with 1 to 3 substituents selected from the group consisting of halogen atom, $C_{1-6}$ alkyl which may be halogenated, $C_{1-6}$ alkoxy which may be halogenated, $C_{1-6}$ alkylthio which may be halogenated, nitro, cyano, sulfo, hydroxy, amino, mono($C_{1-6}$)alkylamino, di($C_{1-6}$)alkylamino, carboxy, $C_{1-6}$ alkoxy-carbonyl and $C_{1-7}$ acylamino, $Y^a$ represents —$CH_2$— or —CO—.

5. A process for producing the compound of claim 1, wherein X is —O— or a salt thereof, which comprises reacting a compound of the formula

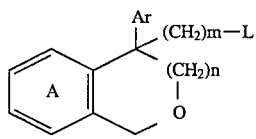

wherein L represents a leaving group and the other variables are as defined in claim 1, or a salt thereof, with a compound of the formula

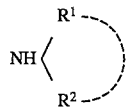

wherein the symbols are as defined in claim 1, or a salt thereof.

6. A method of administering a gonadotropin-releasing hormone antagonistic composition, which comprises the steps of:

selecting a composition comprising a compound as claimed in claim 1, or a salt thereof and a pharmaceutically acceptable carrier, excipient or diluent; and administering said composition to a patient.

7. A method as claimed in claim 6, wherein said composition is administered for preventing or treating a sex hormone-dependent disease.

8. A method as claimed in claim 7, wherein the sex hormone-dependent disease is prostatic cancer, uterus cancer, breast cancer or pituitary tumor.

9. A method as claimed in claim 7, wherein the sex hormone-dependent disease is prostatic hypertrophy, endometriosis, hysteromyoma or precocious puberty.

10. A method of inducing ovulation, comprising the steps of selecting a composition which comprises an effective amount of a compound as claimed in claim 1, or a salt thereof, and a pharmaceutically acceptable carrier, excipient or diluent; and administering said composition to a female human.

11. A method of achieving contraception comprising the steps of selecting a composition which comprises an effective amount of a compound as claimed in claim 1, or a salt thereof; and a pharmaceutically acceptable carrier, excipient or diluent; and administering said composition to a female human.

12. A method of regulating menstrual cycle, comprising the steps of selecting a composition which comprises an effective amount of a compound as claimed in claim 1, or a salt thereof, and a pharmaceutically acceptable carrier, excipient or diluent; and administering said composition to a female human.

13. A method for antagonizing a gonadotropin-releasing hormone in mammals which comprises administrating to a subject in need an effective amount of the compound as claimed in claim 1.

14. A method for treating a sex hormone-dependent disease in mammals which comprises administrating to a subject in need an effective amount of the compound as claimed in claim 1.

15. A method as claimed in claim 14, wherein the sex hormone-dependent disease is prostatic cancer, uterus cancer, breast cancer or pituitary tumor.

16. A method as claimed in claim 14, wherein the sex hormone-dependent disease is prostatic hypertrophy, endometriosis, hysteromyoma or precocious puberty.

17. A method for inducing ovulation in mammals which comprises administrating to a subject in need an effective amount of the compound as claimed in claim 1.

18. A method for achieving contraception in mammals which comprises administrating to a subject in need an effective amount of the compound as claimed in claim 1.

19. A method for regulating a menstrual cycle in mammals which comprises administrating to a subject in need an effective amount of the compound as claimed in claim 1.

20. 3,4-dihydro-6,7-dimethoxy-1'-[3-(4-phenylisochroman-4-yl)propyl]spiro[naphthalene-2(1H),2'-piperidine] or a salt thereof.

21. 4-phenyl-4-{3-[1-(1,2,3,4-tetrahydronaphthylamino)]propyl}isochroman or a salt thereof.

22. A compound as claimed in claim 1, wherein ring B fused to one benzene ring represents

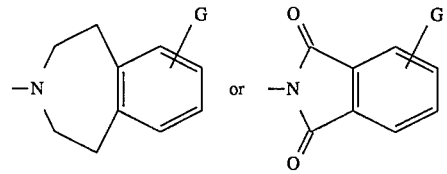

wherein G represents 1 to 3 substituents selected from the group consisting of halogen, $C_{1-6}$ alkyl and $C_{1-6}$ alkoxy.

23. A compound as claimed in claim 1, wherein $R^1$ and $R^2$ taken together with adjacent nitrogen atom form

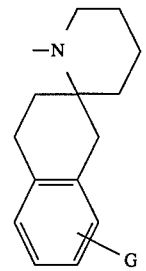

wherein G represents 1 to 3 substituents independently selected from the group consisting of halogen, $C_{1-6}$ alkyl and $C_{1-6}$ alkoxy.

* * * * *

UNITED STATES PATENT AND TRADEMARK OFFICE
CERTIFICATE OF CORRECTION

PATENT NO. : 5,607,939

DATED : March 4, 1997

INVENTOR(S) : KANEYOSHI KATO ET AL.　　　　　　　　Page 1 of 8

It is certified that error appears in the above-identified patent and that said Letters Patent is hereby corrected as shown below:

[57] ABSTRACT

Line 13, "and" (second occurrence) should be deleted.

COLUMN 1

Line 32, "testosteron" should read --testosterone--.
　　Line 45, "testis" should read --testes--.
　　Line 54, "agonist" should read --agonists--.

COLUMN 2

Line 40, "$R^4$" (first occurrence) should read --$R^3$--.

COLUMN 3

Line 62, "concentration" should read --concentration.--.

COLUMN 6

Line 55, "$C_{6-4}$aryl" should read --$C_{6-14}$aryl--.

COLUMN 7

Line 40, "preferred" should read --preferred.--.

COLUMN 13

Line 11, "8quinolyl," should read --8-quinolyl,--.

UNITED STATES PATENT AND TRADEMARK OFFICE
CERTIFICATE OF CORRECTION

PATENT NO. : 5,607,939

DATED : March 4, 1997

INVENTOR(S): KANEYOSHI KATO ET AL.

It is certified that error appears in the above-identified patent and that said Letters Patent is hereby corrected as shown below:

COLUMN 16

Line 25, "Specially," should read --Especially,--.

COLUMN 17

Line 38, "ofto" should read --of 1 to--.
Line 39, "is" (second occurrence) should be deleted.
Line 41, "preferable is" should read --preferably--.

COLUMN 18

Line 64, "N,N-Diphenyl" should read --(1) N,N-Diphenyl--.
Line 65, "N-(2-Phenoxyethyl) should read
--(2) N-(2-Phenoxyethyl)--.

COLUMN 19

Line 2, "[naphthalene(1" should read
--[naphthalene-(1--.
Line 8, "-4yl)" should read -- -4-yl)--.
Line 10, "-4yl)" should read -- -4-yl)--.
Line 21, "-4yl)" should read -- -4-yl)--.
Line 22, "hydrochloride" should read --hydrochloride;--.
Line 33, "this," should read --this--.
Line 45, "(4-phenylisochroman4-yl)" should read
--(4-Phenylisochroman-4-yl)--.
Line 54, "-4phenylisochro-" should read
---4-phenylisochro---.

UNITED STATES PATENT AND TRADEMARK OFFICE
CERTIFICATE OF CORRECTION

PATENT NO. : 5,607,939

DATED : March 4, 1997

INVENTOR(S): KANEYOSHI KATO ET AL.

It is certified that error appears in the above-identified patent and that said Letters Patent is hereby corrected as shown below:

COLUMN 20

Line 6, "1,2,3,4tetrahydroisoquinoline" should read --1,2,3,4-tetrahydroisoquinoline--.

COLUMN 21

Line 43, "earch" should read --earth--.

COLUMN 24

Line 31, "→" should be deleted.

COLUMN 25

Line 21, "hydroxyll" should read --hydroxyl--.
    Line 32, "Insoquinolene" should read --Isoquinoline--.
    Line 39, "stirriing" should read --stirring--.
    Line 45, "cab" should read --can--.

COLUMN 30

Line 52, "portionwiste" should read --portionwise--.

COLUMN 38

Line 51, "(3iodopropyl)" should read --(3-iodopropyl)--.

UNITED STATES PATENT AND TRADEMARK OFFICE
CERTIFICATE OF CORRECTION

PATENT NO. : 5,607,939

DATED : March 4, 1997

INVENTOR(S): KANEYOSHI KATO ET AL.

It is certified that error appears in the above-identified patent and that said Letters Patent is hereby corrected as shown below:

COLUMN 41

Line 48, "2piperidenecarbonitrile." should read
     --2-piperidenecarbonitrile.--.

COLUMN 71

Line 22, "4phenylisochroman" should read
     --4-phenylisochroman--.

COLUMN 72

Line 21, "4phenylisochro-" should read
     --4-phenylisochro---.
   Line 28, "4phenylisochro-" should read
     --4-phenylisochro---.
   Line 33, "4phenylisoch-" should read --4-phenylisoch---.
   Line 58, "4phe-" should read --4-phe---.

COLUMN 73

Line 22, "4phenylisochroman" should read
     --4-phenylisochroman--.

UNITED STATES PATENT AND TRADEMARK OFFICE
CERTIFICATE OF CORRECTION

PATENT NO. : 5,607,939

DATED : March 4, 1997

INVENTOR(S) : KANEYOSHI KATO ET AL.

It is certified that error appears in the above-identified patent and that said Letters Patent is hereby corrected as shown below:

COLUMN 75

Line 37, "(3,4methylenedioxyphenyloxy)" should read
      --(3,4-methylenedioxyphenyloxy)--.
    Line 38, "-4phenylisochroman" should read
      ---4-phenylisochroman--.

COLUMN 81

Table 18-continued, "7/5Hhd2O" should read --7/5H$_2$O--.

COLUMN 91

Table 21 Example I-25, "4.89(2H, s)" should read
      --4.85(2H, s)--.
    Table 21 Example I-26, "2.64" should read --2.65--.

COLUMN 93

Table 22 Example I-31, "2.93" should read --3.92--.

COLUMN 95

Table 23 Example I-36, "4.97" should read --4.87--.

UNITED STATES PATENT AND TRADEMARK OFFICE
CERTIFICATE OF CORRECTION

PATENT NO. : 5,607,939

DATED : March 4, 1997

INVENTOR(S): KANEYOSHI KATO ET AL.

It is certified that error appears in the above-identified patent and that said Letters Patent is hereby corrected as shown below:

COLUMN 101

Table 26 Example I-56, "2.34" should read --2.35--.
   Table 26 Example I-58, "3.34" should read --3.35-- and
     "7.43" should read --7.42--.

COLUMN 105

Table 27 Example I-64, "7.09" should read --7.08--.
   Table 27 Example I-66, "7.99" should read --7.88--.

COLUMN 106

Table 27 Example I-66, "$C_{26}H_{29}NO \cdot HCl \cdot {}^{5}/_{2}H_{2}O$" should read
     --$C_{29}H_{29}NO \cdot HCl \cdot H_{2}O$--.
   Table 28 Example I-70, " 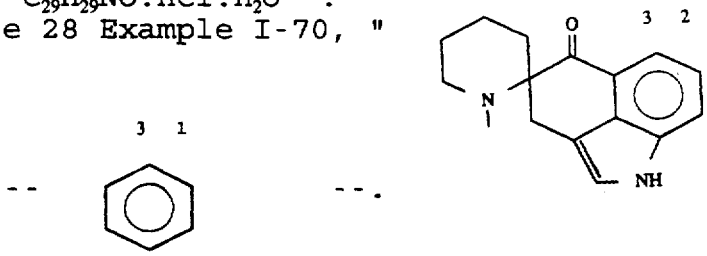 " should read

--  --.

UNITED STATES PATENT AND TRADEMARK OFFICE
CERTIFICATE OF CORRECTION

PATENT NO. : 5,607,939

DATED : March 4, 1997

INVENTOR(S) : KANEYOSHI KATO ET AL.

It is certified that error appears in the above-identified patent and that said Letters Patent is hereby corrected as shown below:

COLUMN 108

Table 29 Example II-4, "4" should read --3--.

COLUMN 123

Line 15, "non-crystakkube" should read
     --non-crystalline--.

COLUMN 140

Line 61, "(109 cells)" should read --($10^9$ cells)--.

COLUMN 143

Line 29, "M." should read --30$\mu$M.--.

COLUMN 144

Line 53, "$C_1$-" should read --$C_{1-6}$--.
   Line 54, "6alkyl," should read --alkyl,-- and
    "C2-6" should read --$C_{2-6}$--.
   Line 61, "[acylamnio] should be deleted.
   Line 64, "C2-6" should read --$C_{2-6}$--.

COLUMN 145

Line 20, "acylamino," should read --acylamino;--.
   Line 67, "loxy," should read --loxy;--.

UNITED STATES PATENT AND TRADEMARK OFFICE
CERTIFICATE OF CORRECTION

PATENT NO. : 5,607,939

DATED : March 4, 1997

INVENTOR(S) : KANEYOSHI KATO ET AL.

It is certified that error appears in the above-identified patent and that said Letters Patent is hereby corrected as shown below:

COLUMN 146

Line 24, "1 to 3," should read --1 to 3;--.
Line 59, "a aralkyl" should read --a $C_{7-16}$ aralkyl--.

COLUMN 147

Line 40, "symbols" should read --variables--.
Line 50, "preventing or" should be deleted.

COLUMN 148

Line 35, "propyl]isochroman" should read
--propyl}isochroman--.

Signed and Sealed this

Thirty-first Day of March, 1998

Attest:

BRUCE LEHMAN

*Attesting Officer*    *Commissioner of Patents and Trademarks*